US012781271B2

(12) United States Patent
Kim

(10) Patent No.: US 12,781,271 B2
(45) Date of Patent: Nov. 3, 2026

(54) METHOD FOR CALCULATING FIDELITY OF A SECONDARY CONTRIBUTOR COMPONENT SIGNAL AT POLYMORPHIC GENETIC LOCIUSING REGRESSION ANALYSIS ON COMPOSITE VARIABLES

(71) Applicant: seeDNA Inc., Tokyo (JP)

(72) Inventor: Kibom Kim, Tokyo (JP)

(73) Assignee: SEEDNA INC., Tokyo (JP)

( * ) Notice: Subject to any disclaimer, the term of this patent is extended or adjusted under 35 U.S.C. 154(b) by 862 days.

(21) Appl. No.: 18/001,544

(22) PCT Filed: Dec. 16, 2021

(86) PCT No.: PCT/JP2021/046513
§ 371 (c)(1),
(2) Date: Dec. 12, 2022

(87) PCT Pub. No.: WO2022/131328
PCT Pub. Date: Jun. 23, 2022

(65) Prior Publication Data
US 2023/0227897 A1 Jul. 20, 2023

(30) Foreign Application Priority Data
Dec. 16, 2020 (JP) ................................ 2020-208554

(51) Int. Cl.
*C12Q 1/6851* (2018.01)
*C12Q 1/686* (2018.01)
*C12Q 1/6886* (2018.01)
*G16B 20/20* (2019.01)
*G16B 40/10* (2019.01)

(52) U.S. Cl.
CPC ........... *C12Q 1/6851* (2013.01); *C12Q 1/686* (2013.01); *C12Q 1/6886* (2013.01); *G16B 20/20* (2019.02); *G16B 40/10* (2019.02); *C12Q 2600/156* (2013.01)

(58) Field of Classification Search
None
See application file for complete search history.

(56) References Cited

U.S. PATENT DOCUMENTS 9,447,453 B2 9/2016 Rava et al.

FOREIGN PATENT DOCUMENTS

| | | |
|---|---|---|
| JP | 2014-502845 | 2/2014 |
| JP | 2016-034282 | 3/2016 |
| JP | 2016-061514 | 4/2016 |
| JP | 2020-529648 | 10/2020 |
| WO | 2015/164432 | 10/2015 |
| WO | 2017/094805 | 6/2017 |
| WO | 2020/236941 | 11/2020 |

OTHER PUBLICATIONS

Extended European Search Report issued in corresponding European Patent Application No. 21906688.3, Oct. 17, 2024, 16 pages.
International Search Report issued in International Application No. PCT/JP2021/046513, Feb. 1, 2022, 5 pages w/translation.
Written Opinon issued in International Application No. PCT/JP2021/046513, Feb. 1, 2022, 3 pages.

*Primary Examiner* — G. Steven Vanni
(74) *Attorney, Agent, or Firm* — Merchant & Gould P.C.

(57) ABSTRACT

The present invention will provide a novel technique to evaluate the reliability of the signal indicating the presence of secondary contributor nucleic acids in the analytical data of nucleic acid mix samples containing a small ratio of secondary contributor nucleic acids, such as cffDNA, ctDNA, and ddcfDNA.
Regression analysis is performed on the composite variables and fidelity obtained from linear combination of a numerical group that includes at least the secondary contributor component signal intensity and the secondary contributor component mix rate in the analysis data, and a model function for calculating the fidelity is obtained.

13 Claims, 11 Drawing Sheets

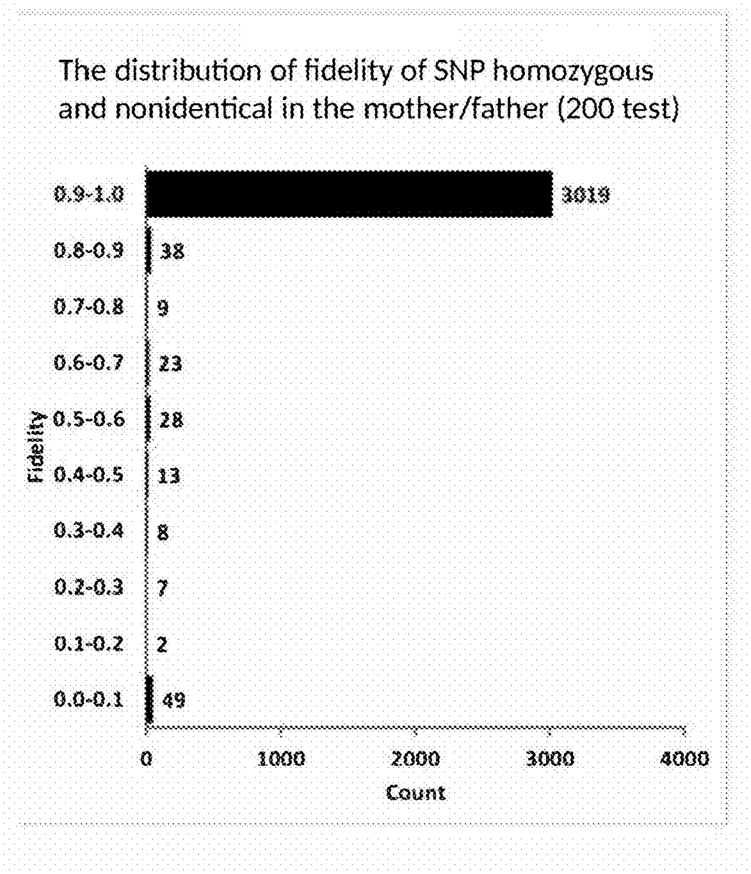
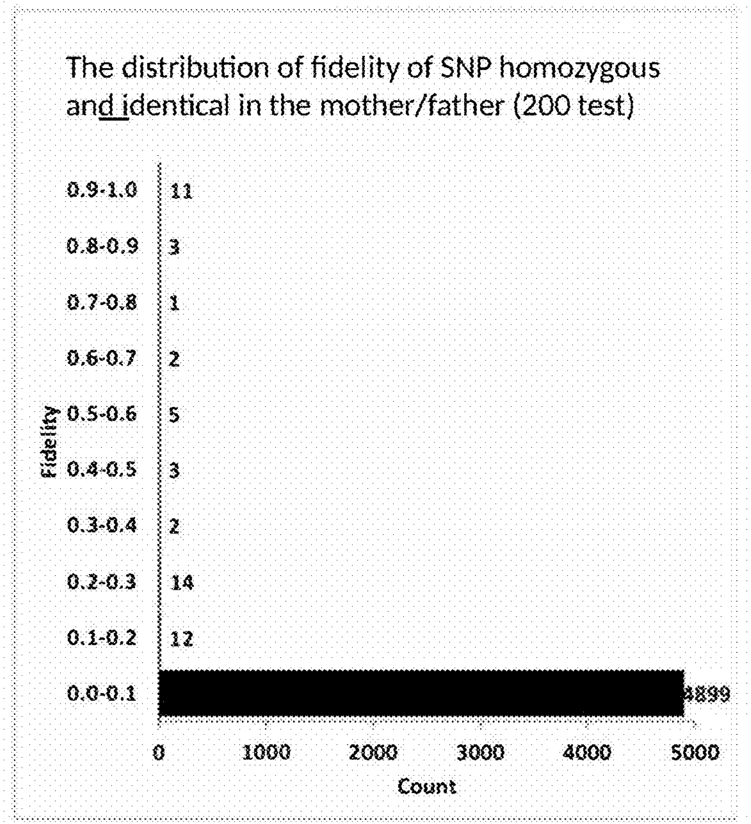
FIG. 4

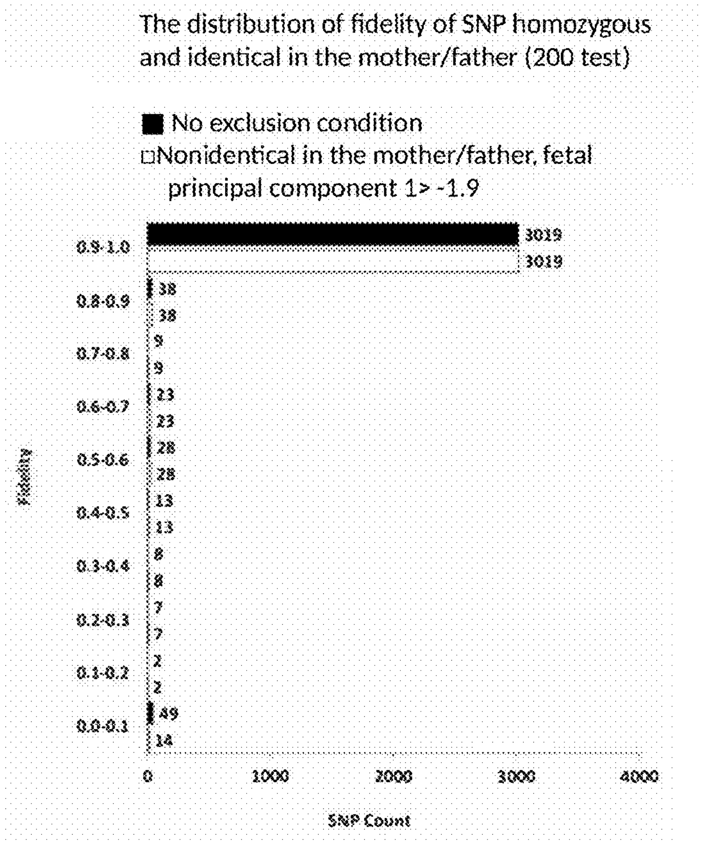
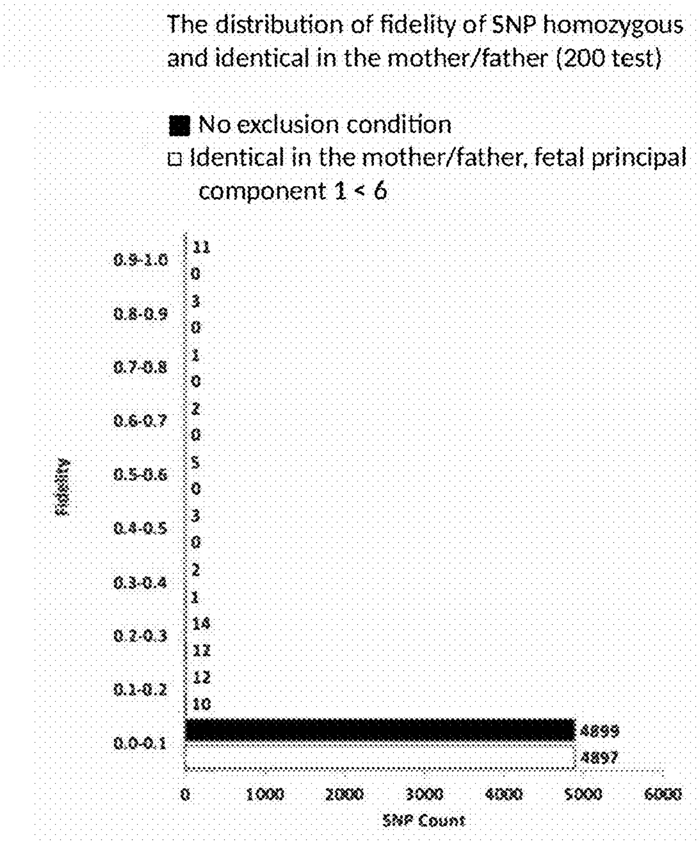
FIG. 7

METHOD FOR CALCULATING FIDELITY OF A SECONDARY CONTRIBUTOR COMPONENT SIGNAL AT POLYMORPHIC GENETIC LOCIUSING REGRESSION ANALYSIS ON COMPOSITE VARIABLES

TECHNICAL FIELD

The present invention is related to data processing of analytical data such as SNPs.

BACKGROUND ART

Uncertainty over the existence of a parent-child relationship has a great impact on legal and family relationships. If a pregnant woman is unsure of the identity of the biological father for her unborn child in her womb, there are several ways to determine the correct biological father.

One method is to wait until the birth of the child, then analyze the genomic DNA of the child and the alleged-father, and compare them after birth. However, there is a high demand for knowing the biological father before the birth of the child. There are several methods to determine the parent-child relationship before birth, such as chorionic diagnosis and the analysis of genetic material collected from amniocentesis. However, these methods are invasive and carry the risk of miscarriage.

Regarding the problems with the invasive diagnostic methods described above, the method of analyzing circulating cell-free DNA (cfDNA) mixed in blood has been applied to parent-child relationship identification. By analyzing cell-free fetal DNA (cffDNA), which is the genetic material of fetal origin mixed into the mother's blood circulation, the Non-Invasive Prenatal Paternity Test (NIPPT) can be realized (e.g., Patent Document 1).

However, there is an important problem to be resolved in the analysis of cffDNA. Maternal blood naturally contains the genetic material of maternal origin as well as that of fetal origin, and the former is far more abundant than the latter. Therefore, the signal indicating the presence of the fetal genetic material obtained by cfDNA analysis is weak. For this, it is extremely difficult to determine whether the signal indicating the presence of the fetal genetic material is really derived from the fetus or not.

In addition to the abovementioned prenatal genetic testing, other areas of application of cfDNA analysis technology include cancer testing ranging from cancer screening tests to anti-cancer treatment progress evaluation. Cancer cells can be destroyed by the immune system, undergo cell death on their own (apoptosis), and circulating tumor cells (CTCs) in the blood circulation can be destroyed under some kind of effect, leading to the leakage of the genomic DNA of cancer cells into the blood. This cfDNA derived from cancer cells is sometimes specifically referred to as ctDNA (circulating tumor DNA). On the other hand, it is known that specific single nucleotide mutations occur in the genomic DNA of cancer cells. Sequence analysis of the polymorphic genetic loci where cancer-associated mutations occur is expected to enable early detection of cancer (e.g., Patent Document 2).

Combining these findings, methods to test for cancer by extracting cfDNA circulating in the blood and analyzing the polymorphic genetic loci where cancer-associated mutations occur can be realized.

However, the majority of cfDNA is derived from the normal genomic DNA of the test subject, and the ratio of cfDNA derived from cancer cells is extremely small. Therefore, as with the prenatal genetic test described above, it is extremely difficult to determine whether the signal suggesting the presence of cancer-associated mutations obtained by cfDNA analysis is really from the genomic DNA of cancer cells, or is just noise.

In addition, the application of cfDNA analysis technology includes monitoring of transplant organ engraftment. Although improvements in immunosuppressive drugs have increased the success rate, rejection is still a major problem for the long-term engraftment of transplanted organs. When a transplanted organ is damaged or becomes necrotic due to rejection, genomic DNA from the cells of the transplanted organs leaks into the bloodstream. This cfDNA derived from the transplanted organ (sometimes specifically referred to as ddcfDNA) is expected to be a biomarker of transplant organ damage. Specifically, the method involves selecting single nucleotide substitutions (SNPs) that can be used to identify the donor and the recipient, and quantifying the extremely small amounts of ddcfDNA that has leaked into the recipient's bloodstream using a next-generation sequencer (e.g., Patent Document 3).

However, since the majority of cfDNA is derived from the recipient's genomic DNA and the ratio of ddcfDNA is minuscule, it is extremely difficult to determine whether the signal suggesting the presence of ddcfDNA obtained from the analysis of cfDNA is really from the genomic DNA of the transplanted organ, or is noise, as in the prenatal genetic test described above.

PRIOR ART DOCUMENT

Patent Documents

Patent Document 1: JP2014-502845A
Patent Document 2: WO2017-094805A
Patent Document 3: JP2020-529648A

DISCLOSURE OF INVENTION

Problems to be Solved by the Invention

The present invention will provide a novel technique to evaluate the fidelity of the signals that indicate the presence of secondary contributor nucleic acids in the analytical data of nucleic acid mix samples, which contain a small ratio of secondary contributor nucleic acids, such as cffDNA, ctDNA, and ddcfDNA.

Means for Solving the Problem

The present invention solves the abovementioned problem as follows.

[1] A method for creating a model function for calculating the fidelity of a secondary contributor component signal, comprising the following step A-1, step A-2, step A-3-1, and step A-4-1.

[Step A-1]

A step of preparing a data set obtained by measuring a nucleic acid mix sample, wherein the sample contains primary and secondary contributor nucleic acids with genetic information from the primary and secondary contributor, respectively, and the data set contains signals indicating the presence of each allele at multiple polymorphic genetic loci in the aforementioned primary and aforementioned secondary contributor nucleic acids (however, the authenticity of the aforementioned signal is known in prior).

[Step A-2]

A step of producing one or more composite variables by linearly combining a numerical group that includes at least the following (A1) and (A2), for the polymorphic genetic loci at which the signals indicating the presence of alleles derived from the aforementioned primary and aforementioned secondary contributor nucleic acids among the aforementioned multiple polymorphic genetic loci from the data of the aforementioned data set are detected separately.

(A1) Secondary contributor component signal intensity indicating the presence of alleles at specific polymorphic genetic loci derived from the aforementioned secondary contributor nucleic acids.

(A2) Secondary contributor component mix rate indicating the ratio of the aforementioned secondary contributor component signal intensity to the total signal intensity derived from alleles at the aforementioned specific polymorphic genetic loci.

[Step A-3-1]

A step of dividing the composite variables produced in aforementioned step A-2 into multiple categories, and assigning the ratio of true secondary contributor component signal intensities corresponding to the aforementioned composite variables in each category as the probability corresponding to the aforementioned composite variables in each category.

[Step A-4-1]

A step of performing regression analysis on the aforementioned composite variables in each aforementioned category and the probability corresponding to the aforementioned composite variables in each aforementioned category, to obtain a model function for calculating fidelity, wherein the aforementioned composite variables are the predictor variable and fidelity is the objective variable.

[2] The method according to [1], wherein the aforementioned composite variables are able to be produced by performing principal component analysis on a numerical group that includes at least aforementioned (A1) and aforementioned (A2).

[3] The method according to [2], wherein the aforementioned composite variables used to create the model function in aforementioned step A-3-1 and step A-4-1 have the highest contribution rate among the one or more composite variables produced in aforementioned step A-2.

[4] The method according to any one of [1] to [3], wherein aforementioned step A-2 is the step of performing principal component analysis on a numerical group that includes at least aforementioned (A1) and aforementioned (A2) to generate one or more principal components as composite variables.

[5] The method according to any one of [1] to [4], wherein aforementioned step A-2 produces one or more composite variables by linearly combining a numerical group that includes at least aforementioned (A1), aforementioned (A2) and more than 1 or 2 selected from the following (A3)~(A5), for the polymorphic genetic loci at which the signals indicating the presence of alleles derived from the aforementioned primary and aforementioned secondary contributor nucleic acids among the aforementioned multiple polymorphic genetic loci from the data in the aforementioned data set are detected separately.

(A3) Primary contributor component signal intensity indicating the presence of alleles at specific polymorphic genetic loci derived from the aforementioned primary contributor nucleic acids.

(A4) Primary contributor component mix rate indicating the ratio of the aforementioned primary contributor component signal intensity to the total signal intensity derived from alleles at the aforementioned specific polymorphic genetic loci.

(A5) Noise obtained by subtracting the aforementioned primary and aforementioned secondary contributor component signal intensities from the total signal intensity derived from alleles at the aforementioned specific polymorphic genetic loci.

[6] The method according to any one of [1] to [5], wherein aforementioned step A-2 produces one or more composite variables by linearly combining the numerical group that includes at least aforementioned (A1), aforementioned (A2) and the following (A3)~(A5), for the polymorphic genetic loci at which the signals indicating the presence of alleles derived from the aforementioned primary and aforementioned secondary contributor nucleic acids among the aforementioned multiple polymorphic genetic loci from the data in the aforementioned data set are detected separately.

(A3) Primary contributor component signal intensity indicating the presence of alleles at specific polymorphic genetic loci derived from the aforementioned primary contributor nucleic acids.

(A4) Primary contributor component mix rate indicating the ratio of the aforementioned primary contributor component signal intensity to the total signal intensity derived from alleles at the aforementioned specific polymorphic genetic loci.

(A5) Noise obtained by subtracting the aforementioned primary and aforementioned secondary contributor component signal intensities from the total signal intensity derived from alleles at the aforementioned specific polymorphic genetic loci.

[7] The method according to any one of [1] to [6], wherein the aforementioned regression analysis is least square method.

[8] The method according to any one of [1] to [7], wherein the secondary contributor component signal intensity or the secondary contributor component mix rate is weighted to the maximum in the first-order homogenous polynomial representing the aforementioned composite variable.

[9] The method according to any one of [1] to [8], wherein the numerical values in the numerical group that is linearly combined in aforementioned step A-2 are standardized.

[10] The method according to any one of [1] to [9], wherein two or more composite variables are produced in aforementioned step A-2, the fidelity is assigned to each of the aforementioned two or more composite variables in aforementioned step A-3-1, mutually independent two or more model functions wherein each of the aforementioned two or more composite variables are the predictor variable are created in aforementioned step A-4-1, and comprising a step of multiplying the aforementioned two or more model functions by each other to create a model function of multiplication is included.

[11] A method for creating a model function for calculating the fidelity of a secondary contributor component signal, comprising the following step A-1, step A-3-2, and step A-4-2.

[Step A-1]

A step of preparing a data set obtained by measuring a nucleic acid mix sample, wherein the sample contains primary and secondary contributor nucleic acids with genetic information from the primary and secondary contributor, respectively, and the data set contains signals indicating the presence of each allele at multiple polymorphic genetic loci in the aforementioned primary and aforementioned secondary contributor nucleic acids (however, the authenticity of the aforementioned signal is known in prior).

[Step A-3-2]

A step of dividing the secondary contributor component signal intensities indicating the presence of alleles at specific polymorphic genetic loci into multiple categories, for the polymorphic genetic loci wherein the signals indicating the presence of alleles derived from the aforementioned primary and aforementioned secondary contributor nucleic acids among the aforementioned multiple polymorphic genetic loci are detected separately, and assigning the ratio of that true from the aforementioned secondary contributor component signal intensities in each category as the probability corresponding to the aforementioned secondary contributor component signal intensities in each aforementioned category.

[Step A-4-2]

A step of performing regression analysis on the aforementioned secondary contributor component signal intensities in each aforementioned category and the probability corresponding to the aforementioned secondary contributor component signal intensities in each aforementioned category, to obtain a model function for calculating fidelity, wherein the aforementioned secondary contributor component signal intensities are the predictor variable and fidelity is the objective variable.

[12] A method for creating a model function for calculating the fidelity of a secondary contributor component signal, comprising the following step A-1, step A-3-3, and step A-4-3.

[Step A-1]

A step of preparing a data set obtained by measuring a nucleic acid mix sample, wherein the sample contains primary and secondary contributor nucleic acids with genetic information from the primary and secondary contributor, respectively, and the data set contains signals indicating the presence of each allele at multiple polymorphic genetic loci in the aforementioned primary and aforementioned secondary contributor nucleic acids (however, the authenticity of the aforementioned signal is known in prior).

[Step A-3-3]

A step of dividing the secondary contributor component mix rates indicating the ratio of secondary contributor component signal intensity to the total signal intensity derived from alleles at specific polymorphic genetic loci into multiple categories, for the polymorphic genetic loci wherein the signals indicating the presence of alleles derived from the aforementioned primary and aforementioned secondary contributor nucleic acids among the aforementioned multiple polymorphic genetic loci are detected separately, and assigning the ratio of that true from the aforementioned secondary contributor component mix rates in each category as the probability corresponding to the aforementioned secondary contributor component mix rates in each aforementioned category.

[Step A-4-3]

A step of performing a regression analysis on the aforementioned secondary contributor component mix rates in each aforementioned category and the probability corresponding to the aforementioned secondary contributor component mix rates in each aforementioned category, to obtain a model function for calculating fidelity, wherein the aforementioned secondary contributor component mix rates are the predictor variable and fidelity is the objective variable.

[13] The method according to any one of [1] to [12], wherein the aforementioned model function is a sigmoid function.

[14] The method according to any one of [1] to [13], wherein the aforementioned model function is a sigmoid function with two parameters.

[15] A method for creating a model function, comprising a step of creating a model function of multiplication by multiplying two or more model functions selected from the following model functions by each other:

a model function created by the method according to any one of [1] to [10], a model function created by the method according to [11], and a model function created by the method according to [12].

[16] A method for creating a model function, which comprises the step of creating a model function of multiplication by multiplying the following model functions by each other:

a model function created by the method according to any one of [1] to [10], and a model function created by the method according to [11], and/or a model function created by the method according to [12].

[17] A method for creating a model function, comprising the step of creating a model function of multiplication by multiplying the following model functions by each other:

a model function created by the method according to any one of [1] to[10], a model function created by the method according to [11], and a model function created by the method according to [12].

[18] The method according to any one of [1] to[17], wherein the aforementioned polymorphic genetic loci comprise of a single nucleotide polymorphism.

[19] The method according to any one of [1] to [18], wherein the aforementioned data set is obtained by sequence analysis, digital PCR, microarray, real-time PCR, or mass spectrometry.

[20] The method according to any one of [1] to [18], wherein the aforementioned data set is obtained by sequence analysis, and the aforementioned secondary contributor component signal intensity is the count number, read number, ionic concentration or electrical signal of the sequence tag.

[21] The method according to any one of [1] to [18], wherein the aforementioned data set is obtained by digital PCR, and the aforementioned secondary contributor component signal intensity is the number of wells in which fluorescence is observed.

[22] The method according to any one of [1] to [18,] wherein the aforementioned data set is obtained by microarray, and the aforementioned secondary contributor component signal intensity is the fluorescence intensity.

[23] The method according to any one of [1] to [11], wherein the aforementioned primary contributor is the mother, the aforementioned secondary contributor is the fetus in the womb of the aforementioned mother, and the aforementioned nucleic acid mix sample is circulating cell-free nucleic acid sample collected from the aforementioned mother, and wherein aforementioned step A-1, step A-2, step A-3-1 and step A-4-1 each correspond to step $A_1$-1, step $A_1$-2, step $A_1$-3-1, and step $A_1$-4-1, respectively.

[Step $A_1$-1]

A step of preparing a data set obtained by measuring a circulating cell-free nucleic acid sample, wherein the sample contains primary and secondary contributor nucleic acids with genetic information from the mother and the fetus, respectively, and the data set contains signals indicating the presence of each allele at multiple polymorphic genetic loci in the aforementioned primary and aforementioned secondary contributor nucleic acids (however, the authenticity of the aforementioned signal is known in prior).

[Step $A_1$-2]

A step of producing one or more composite variables by linearly combining a numerical group that includes at least aforementioned (A1) and aforementioned (A2), for the polymorphic genetic loci that are homozygous in the aforementioned mother and homozygous in the father, and the signals indicating the presence of alleles derived from the aforementioned primary and aforementioned secondary contributor nucleic acids among the aforementioned multiple polymorphic genetic loci from the data of the aforementioned data set are detected separately.

[Step $A_1$-3-1]

A step of dividing the composite variables produced in aforementioned step $A_1$-2 into multiple categories, and assigning the ratio of true secondary contributor component signal intensities corresponding to the aforementioned composite variables in each category as the probability corresponding to the aforementioned composite variables in each category.

(However, for an allele that is homozygous in the aforementioned mother and homozygous in the father, and the genotype is nonidentical in the aforementioned mother and the aforementioned father, the secondary contributor component signal is considered true if the aforementioned secondary contributor component signal and the primary contributor component signal are detected separately, where else the secondary contributor component signal is considered false if the aforementioned secondary contributor component signal and the primary contributor component signal are not detected separately.

For an allele that is homozygous in the aforementioned mother and homozygous in the father, and the genotype is identical in the aforementioned mother and the aforementioned father, the secondary contributor component signal is considered false if the aforementioned secondary contributor component signal and the primary contributor component signal are detected separately, where else the secondary contributor component signal is considered true if the aforementioned secondary contributor component signal and the primary contributor component signal are not detected separately.)

[Step $A_1$-4-1]

A step of performing regression analysis on the aforementioned composite variables in each aforementioned category and the probability corresponding to the aforementioned composite variables in each aforementioned category, to obtain a model function for calculating fidelity, wherein the aforementioned composite variables are the predictor variable and the fidelity is the objective variable.

[24] The method according to any one of [1] to [10], wherein the aforementioned primary contributor is a test subject with a healthy body and the aforementioned secondary contributor is cancer cells, and wherein aforementioned step A-1, step A-2, step A-3-1 and step A-4-1 each correspond to step $A_2$-1, step $A_2$-2, step $A_2$-3-1, and step $A_2$-4-1, respectively.

[Step $A_2$-1]

A step of preparing a data set obtained by measuring a nucleic acid mix sample, wherein the sample is artificially prepared by adding the secondary contributor nucleic acid consisting of multiple nucleic acid fragments with sequence information of the aforementioned polymorphic genetic loci where cancer-associated mutations have been introduced, to the nucleic acid sample collected from the aforementioned test subject that contains the primary contributor nucleic acid containing genetic information of the test subject, and the data set contains signals indicating the presence of normal type of alleles in the aforementioned primary contributor nucleic acid, and signals indicating the presence of alleles containing the aforementioned mutations in the aforementioned secondary contributor nucleic acid.

[Step $A_2$-2]

A step of producing one or more composite variables by linearly combining a numerical group that includes at least aforementioned (A1) and aforementioned (A2), for the polymorphic genetic loci at which the signals indicating the presence of alleles derived from the aforementioned primary and aforementioned secondary contributor nucleic acids among the aforementioned multiple polymorphic genetic loci from the data of the aforementioned data set are detected separately.

[Step $A_2$-3-1]

A step of dividing the composite variables produced in aforementioned step $A_2$-2 into multiple categories, and assigning the ratio of true secondary contributor component signal intensities corresponding to the aforementioned composite variables in each category as the probability corresponding to the aforementioned composite variables in each category.

(However, in cases where nucleic acid fragment containing the sequence information of the aforementioned polymorphic genetic loci, at which the aforementioned mutation was introduced, is added to the nucleic acid mix sample, the secondary contributor component signal is considered true if the secondary contributor component signal is detected for the nucleic acid fragment, where else the secondary contributor component signal is considered false if the secondary contributor component signal is not detected for the nucleic acid fragment.

In cases where nucleic acid fragment containing the sequence information of the aforementioned polymorphic genetic loci, at which the aforementioned mutation was introduced, is not added to the nucleic acid mix sample, the secondary contributor component signal is considered false if the secondary contributor component signal is detected for the nucleic acid fragment, where else the secondary contributor component signal is considered true if the secondary contributor component signal is not detected for the nucleic acid fragment.)

[Step $A_2$-4-1]

A step of performing regression analysis on the aforementioned composite variables in each aforementioned category and the probability corresponding to the aforementioned composite variables in each aforementioned category, to obtain a model function for calculating fidelity, wherein the aforementioned composite variables are the predictor variable and the fidelity is the objective variable.

[25] A method for creating a model function for calculating the fidelity of a secondary contributor component signal, comprising of the following step $A_{2'}$-1, step $A_{2'}$-2, step $A_{2'}$-3-1 and step $A_{2'}$-4-1.

[Step $A_{2'}$-1]

A step of preparing a data set obtained by measuring multiple nucleic acid mix sample, wherein the sample is artificially prepared by adding the secondary contributor nucleic acid consisting of multiple nucleic acid fragments with sequence information of the aforementioned single polymorphic genetic locus where cancer-associated mutations have been introduced, to the nucleic acid sample collected from a test subject with a healthy body that contains primary contributor nucleic acid containing genetic information of the test subject, and in which the ratios of the aforementioned secondary contributor nucleic acid are each different, and the data set contains signals indicating the presence of normal type of alleles in the aforementioned primary contributor nucleic acid, and signals indicating the presence of alleles containing the aforementioned mutations in the aforementioned secondary contributor nucleic acid.

[Step $A_{2'}$-2]

A step of producing one or more composite variables by linearly combining a numerical group that includes at least the following (A1') and (A2'), for the single polymorphic genetic locus at which the signals indicating the presence of alleles derived from the aforementioned primary and aforementioned secondary contributor nucleic acids from the data of the aforementioned data set are detected separately.

(A1') Secondary contributor component signal intensity indicating the presence of alleles at the aforementioned single polymorphic genetic locus derived from the aforementioned secondary contributor nucleic acids.

(A2') Secondary contributor component mix rate indicating the ratio of the aforementioned secondary contributor component signal intensity to the total signal intensity derived from alleles at the aforementioned single polymorphic genetic locus.

[Step $A_2$-3-1]

A step of dividing the composite variables produced in aforementioned step $A_{2'}$-2 into multiple categories, and assigning the ratio of true secondary contributor component signal intensities corresponding to the aforementioned composite variables in each category as the probability corresponding to the aforementioned composite variables in each category.

(However, in case where nucleic acid fragment containing the sequence information of the aforementioned polymorphic genetic loci, at which the aforementioned mutation was introduced, is added to the nucleic acid mix sample, the secondary contributor component signal is considered true if the secondary contributor component signal is detected for the nucleic acid fragment, where else the secondary contributor component signal is considered false if the secondary contributor component signal is not detected for the nucleic acid fragment.

In case where nucleic acid fragment containing the sequence information of the aforementioned polymorphic genetic loci, at which the aforementioned mutation was introduced, is not added to the nucleic acid mix sample, the secondary contributor component signal is considered false if the secondary contributor component signal is detected for the nucleic acid fragment, where else the secondary contributor component signal is considered true if the secondary contributor component signal is not detected for the nucleic acid fragment.)

[Step $A_2$-4-1]

A step of performing regression analysis on the aforementioned composite variables in each aforementioned category and the probability corresponding to the aforementioned composite variables in each aforementioned category, to obtain a model function for calculating fidelity, wherein the aforementioned composite variables are the predictor variable and the fidelity is the objective variable.

[26] The method according to any one of [1] to [10], wherein the aforementioned primary contributor is the recipient of the organ transplant and the aforementioned secondary contributor is the transplanted organ, and wherein aforementioned step A-1, step A-2, step A-3-1, and step A-4-1 each correspond to step $A_3$-1, step $A_3$-2, step $A_3$-3-1, and step $A_3$-4-1, respectively.

[Step $A_3$-1]

A step of preparing a data set obtained by measuring a nucleic acid mix sample, wherein the sample contains primary and secondary contributor nucleic acids with genetic information from the recipient of the organ transplant and the transplanted organ, respectively, and the data set contains signals indicating the presence of each allele at multiple polymorphic genetic loci in the aforementioned primary and aforementioned secondary contributor nucleic acids (however, the authenticity of the aforementioned signal is known in prior).

[Step $A_3$-2]

A step of producing one or more composite variables by linearly combining a numerical group that includes at least aforementioned (A1) and aforementioned (A2), for the polymorphic genetic loci at which the signals indicating the presence of alleles derived from the aforementioned primary and aforementioned secondary contributor nucleic acids among the aforementioned multiple polymorphic genetic loci from the data of the aforementioned data set are detected separately.

[Step $A_3$-3-1]

A step of dividing the composite variables produced in aforementioned step $A_3$-2 into multiple categories, and assigning the ratio of true secondary contributor component signal intensities corresponding to the aforementioned composite variables in each category as the probability corresponding to the aforementioned composite variables in each category.

(However, for an allele not present in the recipient, and homozygous or heterozygous in the donor, the secondary contributor component signal is considered true if the aforementioned secondary contributor component signal and the primary contributor component signal are detected separately, where else the secondary contributor component signal is considered false if the aforementioned secondary contributor component signal and the primary contributor component signal are not detected separately.

For an allele not present in both the recipient and the donor, the secondary contributor component signal is considered false if the aforementioned secondary contributor component signal and the primary contributor component signal are detected separately, where else the secondary contributor component signal is considered true if the aforementioned secondary contributor component signal and the primary contributor component signal are not detected separately.)

[Step $A_3$-4-1]

A step of performing regression analysis on the aforementioned composite variables in each aforementioned category and the probability corresponding to the aforementioned composite variables in each aforementioned category, to obtain a model function for calculating the fidelity, wherein the aforementioned composite variables are the predictor variable and the fidelity is the objective variable.

[27] A method for calculating the fidelity wherein the fidelity is calculated by inputting predictor variable into a model function, and the aforementioned model function is:

the aforementioned model function obtained by the method according to any one of [1] to [26], the model function in any one of the following equations 1 to 3, or the model function of multiplication that is created by multiplying two or more model functions selected from the group of model functions of the following equations 1 to 3, and the aforementioned predictor variable is a numerical value more than one or two selected from the following (B1) and (B2) in the data set obtained in the following step B-1, and the composite variables obtained in the following step B-2.

[Step B-1]

A step of preparing a data set obtained by measuring a nucleic acid mix sample, wherein the sample contains primary and secondary contributor nucleic acids with genetic information from the primary and secondary contributors, respectively, and the data set contains signals indicating the presence of each allele at multiple polymorphic genetic loci in the aforementioned primary and aforementioned secondary contributor nucleic acids.

[Step B-2]

A step of producing one or more composite variables by linearly combining a numerical group that includes at least the following (B1) and (B2), for the polymorphic genetic loci at which the signals indicating the presence of alleles derived from the aforementioned primary and aforementioned secondary contributor nucleic acids among the aforementioned multiple polymorphic genetic loci from the data of the aforementioned data set are detected separately.

(B1) Secondary contributor component signal intensity indicating the presence of alleles at specific polymorphic genetic loci derived from the aforementioned secondary contributor nucleic acids.

(B2) Secondary contributor component mix rate indicating the ratio of the aforementioned secondary contributor component signal intensity to the total signal intensity derived from alleles at the aforementioned specific polymorphic genetic loci.

$$f1(x1) = \frac{1}{1 + e^{-A1(x1 - x01)}} \quad \text{[Equation 1]}$$

(x1: the first principal component, A1: gradient of transition region, x01: half point) (However, in Equation 1, A1 is 15.4~15.6, and x01 is −0.8~−0.6)

$$f2(x2) = \frac{1}{1 + e^{-A2(x2 - x02)}} \quad \text{[Equation 2]}$$

(x2: secondary contributor component signal intensity, A2: gradient of transition region, x02: half point) (However, in Equation 2, A2 is 1.8~2.0, and x02 is 2.5~2.7)

$$f3(x3) = \frac{1}{1 + e^{-A3(x3 - x03)}} \quad \text{[Equation 3]}$$

(x3: secondary contributor component mix rate, A3: gradient of transition region, x03: half point) (However, in Equation 3, A3 is 9.3~9.5, and x03 is 0.5~0.7)

[28] The method according to [27], wherein the aforementioned primary contributor is the mother, the aforementioned secondary contributor is the fetus in the womb of the aforementioned mother, the aforementioned nucleic acid mix sample is circulating cell-free nucleic acid sample collected from the aforementioned mother, and wherein, aforementioned step B-1 and step B-2 each correspond to step $B_1$-1 and $B_1$-2, respectively.

[Step $B_1$-1]

A step of preparing a data set obtained by measuring a circulating cell-free nucleic acid sample, wherein the sample contains a primary and secondary contributor nucleic acid with genetic information from the mother and the fetus, respectively, and the data set contains signals indicating the presence of each allele at multiple polymorphic genetic loci in the aforementioned primary and aforementioned secondary contributor nucleic acids.

[Step $B_1$-2]

A step of producing one or more composite variables by linearly combining a numerical group that includes at least aforementioned (B1) and aforementioned (B2), for the polymorphic genetic loci that is homozygous in the aforementioned mother, and the signals indicating the presence of alleles derived from the aforementioned primary and aforementioned secondary contributor nucleic acids among the aforementioned multiple polymorphic genetic loci from the data of the aforementioned data set are detected separately.

[29] The method according to [28], wherein the multiple polymorphic genetic loci are utilized in the method for identifying human individuals, and which is a method for calculating fidelity for non-invasive prenatal paternity test.

[30] The method according to [27], wherein the aforementioned primary contributor is the cancer test subject, the aforementioned secondary contributor is cancer cells, the aforementioned nucleic acid mix sample is a circulating cell-free nucleic acid sample collected from the aforementioned cancer test subject, and wherein aforementioned step B-1 and step B-2 each correspond to step $B_2$-1 and step $B_2$-2, respectively.

[Step $B_2$-1]

A step of preparing a data set obtained by measuring a circulating cell-free nucleic acid sample, wherein the sample contains a primary and secondary contributor nucleic acid with genetic information from the cancer test subject and the cancer cells, respectively, and the data set containing signals indicating the presence of each allele at multiple polymorphic genetic loci associated with cancer in the aforementioned primary and aforementioned secondary contributor nucleic acids.

[Step $B_2$-2]

A step of producing one or more composite variables by linearly combining a numerical group that includes at least aforementioned (B1) and aforementioned (B2), for the polymorphic genetic loci at which signals indicating the presence of normal type alleles and signals indicating the presence of a mutant type allele among the aforementioned multiple polymorphic genetic loci from the data of the aforementioned data set are detected separately.

[31] The method according to [30] comprising:

removing the data related to the polymorphic genetic loci with a mutant allele homozygous or heterozygous in the test subject, among the aforementioned multiple polymorphic genetic loci from the data of the aforementioned data set at aforementioned step $B_2$-2, and producing one or more composite variable by linearly combining a numerical group that includes at least aforementioned (B1) and aforementioned (B2), for the polymorphic genetic loci at which the signals indicating the presence of normal type and mutant type of alleles among the aforementioned multiple polymorphic genetic loci from the remaining data of the aforementioned data set.

[32] The step according to [27], wherein the aforementioned primary contributor is the recipient of the organ transplant, the aforementioned secondary contributor is the transplanted organ, the aforementioned nucleic acid mix sample is the circulating cell-free nucleic acid sample collected from the aforementioned recipient, and wherein aforementioned step B-1 and step B-2 each correspond to step $B_3$-1 and step $B_3$-2, respectively.

[Step $B_3$-1]

A step of preparing a data set obtained by measuring a circulating cell-free nucleic acid sample wherein the sample contains primary contributor nucleic acid with genetic information from the recipient, and may contain secondary contributor nucleic acid with genetic information from the transplanted organ, and the data set contains signals indicating the presence of each allele at the multiple polymorphic genetic loci in the aforementioned primary and aforementioned secondary contributor nucleic acids.

[Step $B_3$-2]

A step of producing one or more composite variables by linearly combining a numerical group that includes at least aforementioned (B1) and aforementioned (B2), for the polymorphic genetic loci at which the signals indicating the presence of alleles derived from the aforementioned primary and aforementioned secondary contributor nucleic acids among the aforementioned multiple polymorphic genetic loci from the data of the aforementioned data set are detected separately.

[33] The method according to [32], wherein the aforementioned multiple polymorphic genetic loci are the polymorphic genetic loci used in the method for identifying human individuals, and which is a method for calculating fidelity for monitoring transplanted organ engraftment.

[34] A method for setting exclusion conditions to exclude data, wherein the data is unsuitable for calculating fidelity via the method according to any one of [27] to [33], and comprising the following step C-1-1, step C-2-1, step C-3-1, and step C-4-1.

[Step C-1-1]

A step of preparing a data set obtained by measuring a nucleic acid mix sample, wherein the sample contains primary and secondary contributor nucleic acids with genetic information from the primary and secondary contributor, respectively, and the data set contains signals indicating the presence of each allele at multiple polymorphic genetic loci in the aforementioned primary and aforementioned secondary contributor nucleic acids (however, the authenticity of the aforementioned signal is known in prior).

(However, the aforementioned primary contributor is the mother, the aforementioned secondary contributor is the fetus in the womb of the aforementioned mother, and the aforementioned nucleic acid mix sample is a circulating cell-free nucleic acid sample collected from the aforementioned mother, or the aforementioned primary contributor is the recipient, the aforementioned secondary contributor is the transplanted organ, and the aforementioned nucleic acid mix is a circulating cell-free nucleic acid sample collected from the aforementioned recipient.)

[Step C-2-1]

A step of producing the composite variable with the highest contribution rate among the composite variables obtained by linearly combining a numerical group that contains at least the following (C1), (C2) and (C3), for the polymorphic genetic loci with an allele wherein the allele is:

homozygous in the aforementioned mother and homozygous in the aforementioned father, and the genotype is nonidentical in the aforementioned mother and the aforementioned father, or homozygous in the aforementioned recipient and homozygous in the aforementioned donor of the organ transplant, and the genotype is nonidentical in the aforementioned recipient and the aforementioned donor.

(C1) Secondary contributor component signal intensity indicating the presence of alleles at specific polymorphic genetic loci derived from the aforementioned secondary contributor nucleic acids.

(C2) Secondary contributor component mix rate indicating the ratio of the aforementioned secondary contributor component signal intensity to the total signal intensity derived from alleles at the aforementioned specific polymorphic genetic loci.

(C3) Noise obtained by subtracting the aforementioned primary and aforementioned secondary contributor component signal intensities from the total signal intensity derived from alleles at the aforementioned specific polymorphic genetic loci.

[Step C-3-1]

A step of setting a threshold on the value of the aforementioned composite variable, to exclude some or all the outliers of the aforementioned composite variables obtained by the aforementioned linear combination in aforementioned step C-2-1.

[Step C-4-1]

A step of setting the following exclusion condition C1 as the condition to be excluded from the data set to be input to the model function for calculating fidelity.

(Exclusion Condition C1)

From the data set obtained by analyzing a nucleic acid mix sample that contains primary contributor nucleic acid with genetic information from the mother or the recipient, and secondary contributor nucleic acid with genetic information from the fetus or the transplanted organ, the composite variable with the highest contribution rate that is obtained by linearly combining a numerical group that includes at least aforementioned (C1), aforementioned (C2), and aforementioned (C3), for the polymorphic genetic loci with alleles that are homozygous in the mother and homozygous in the alleged-father, and the genotype is nonidentical in the aforementioned mother and the aforementioned alleged-father, or alleles that are homozygous in the aforementioned recipient and homozygous in the aforementioned donor of the transplanted organ, and the genotype is nonidentical in the aforementioned recipient and the aforementioned donor, corresponding to less than the aforementioned threshold set in aforementioned step C-3-1 are removed.

[35] A method for setting exclusion conditions to exclude data, wherein the data is unsuitable for calculating fidelity via the method according to any one of [27] to [33], and comprising the following step C-1-2, step C-2-2, step C-3-2, and step C-4-2.

[Step C-1-2]

A step of preparing a data set obtained by measuring a nucleic acid mix sample, wherein the sample contains primary and secondary contributor nucleic acids with genetic information from the primary and secondary contributor, respectively, and the data set contains signals indicating the presence of each allele at multiple polymorphic genetic loci in the aforementioned primary and the aforementioned secondary contributor nucleic acids (however, the authenticity of the aforementioned signal is known in prior).

(However, the aforementioned primary contributor is the mother, the aforementioned secondary contributor is the fetus in the womb of the aforementioned mother, and the aforementioned nucleic acid mix sample is a circulating cell-free nucleic acid sample collected from the aforementioned mother, or the aforementioned primary contributor is the recipient, the aforementioned secondary contributor is the transplanted organ, and the aforementioned nucleic acid mix is a circulating cell-free nucleic acid sample collected from the aforementioned recipient.)

[Step C-2-2]

A step of producing the composite variable with the highest or the second highest contribution rate among the composite variables obtained by linearly combining a numerical group that contains at least the following (C1), (C2) and (C3), for the polymorphic genetic loci with an allele that is homozygous in the aforementioned mother and homozygous in the aforementioned father, and the genotype is identical in the aforementioned mother and the aforementioned father, or an allele that is homozygous in the aforementioned recipient and homozygous in the aforementioned donor of the organ transplant, and the genotype is identical in the aforementioned recipient and the aforementioned donor.

(C1) Secondary contributor component signal intensity indicating the presence of alleles at specific polymorphic genetic loci derived from the aforementioned secondary contributor nucleic acids.

(C2) Secondary contributor component mix rate indicating the ratio of the aforementioned secondary contributor component signal intensity to the total signal intensity derived from alleles at the aforementioned specific polymorphic genetic loci.

(C3) Noise obtained by subtracting the aforementioned primary and aforementioned secondary contributor component signal intensities from the total signal intensity derived from alleles at the aforementioned specific polymorphic genetic loci.

[Step C-3-2]

A step of setting a threshold on the value of the aforementioned composite variable, to exclude some or all the outliers of the aforementioned composite variables obtained by the aforementioned linear combination in aforementioned step C-2-2.

[Step C-4-2]

A step of setting the following exclusion condition C2 as the condition to be excluded from the data set to be input to the model function for calculating fidelity.

(Exclusion Condition C2)

From the data set obtained by analyzing a nucleic acid mix sample that contains primary contributor nucleic acid with genetic information from the mother or the recipient, and secondary contributor nucleic acid with genetic information from the fetus or the transplanted organ, the composite variable with the highest or the second highest contribution rate that is obtained by linearly combining a numerical group that includes at least aforementioned (C1), aforementioned (C2) and aforementioned (C3), for the polymorphic genetic loci with alleles that are homozygous in the mother and homozygous in the alleged-father, and the genotype is identical in the aforementioned mother and the aforementioned alleged-father, or alleles that are homozygous in the aforementioned recipient and homozygous in the aforementioned donor of the transplanted organ, and the genotype is identical in the aforementioned recipient and the aforementioned donor, corresponding to less than the aforementioned threshold set in aforementioned step C-3-2 are removed.

[36] The method according to [34] or [35], wherein the aforementioned polymorphic genetic locus is the single nucleotide polymorphic genetic locus used in the method for identifying human individuals.

[37] The method according to any one of [34] to [36], which is the method for monitoring of transplant organ engraftment.

[38] The method according to any one of [34] to [37], wherein the aforementioned outlier is the numerical value for the allele in cases where the fidelity of the signal indicating the presence of the specific allele derived from the aforementioned secondary contributor nucleic acid is calculated to be less than 0.8, regardless of the fact that the allele is included in the aforementioned nucleic acid mix sample, and/or the numerical value for the allele in cases where the fidelity of the signal indicating the presence of the specific allele derived from the aforementioned secondary contributor nucleic acid is calculated as 0.2 or above, regardless of the fact that the allele is not included in the nucleic acid mix sample, when the fidelity is calculated via the method according to any of [27]~[33].

[39] The method according to any one of [34] to [38], wherein the aforementioned outlier is a number that is more than twice as far from the mean of the aforementioned composite variable as its standard deviation.

[40] The method according to [32] or [33], for obtaining the data remaining after removing the data set that corresponds to the exclusion condition C1 identified in the method according to [34], and/or the exclusion condition C2 identified in [35], in aforementioned step B-1.

[41] The method for calculating fidelity wherein the fidelity is calculated by inputting predictor variable into a model function, and the model function is:

the aforementioned model function obtained by the method according to any one of [1] to [26], the model function in any one of the following equations 1~3, or the model function of multiplication that is created by multiplying two or more model functions selected from the model functions in the following equations 1~3, and the aforementioned predictor variable is a numerical value more than 1 or 2, selected from the composite variables that are obtained via the following (B1) and (B2), and step $B_4$-2 below, which are included in the data set obtained in following step $B_4$-1.

[Step $B_4$-1]

A step of preparing a data set obtained by measuring a circulating cell-free nucleic acid sample, wherein the sample containing primary contributor nucleic acids with genetic information from the mother, and secondary contributor nucleic acids with genetic information from the fetus in the womb of the aforementioned mother, and the data set contains signals indicating the presence of each allele at the multiple polymorphic genetic loci associated with disease in the aforementioned primary and aforementioned secondary contributor nucleic acids.

[Step $B_4$-2]

A step of removing data related to the polymorphic genetic loci with a mutant allele heterozygous in the mother, from the data in the aforementioned data set, and producing one or more composite variables by linearly combining a numerical group that includes at least the following (B1) and (B2), for the polymorphic genetic loci at which the signals indicating the presence of alleles derived from the aforementioned primary and aforementioned secondary contributor nucleic acids, among the aforementioned multiple polymorphic genetic loci from the data in the aforementioned data set remaining after removing, are detected separately.

(B1) Secondary contributor component signal intensity indicating the presence of alleles at specific polymorphic genetic loci derived from the aforementioned secondary contributor nucleic acids.

(B2) Secondary contributor component mix rate indicating the ratio of the aforementioned secondary contributor component signal intensity to the total signal intensity derived from alleles at the aforementioned specific polymorphic genetic loci.

$$f1(x1) = \frac{1}{1+e^{-A1(x1-x01)}} \quad \text{[Equation 1]}$$

(x1: the first principal component, A1: gradient of transition region, x01: half point) (However, in Equation 1, A1 is 15.4~15.6, and x01 is −0.8~−0.6)

$$f2(x2) = \frac{1}{1+e^{-A2(x2-x02)}} \quad \text{[Equation 2]}$$

(x2: secondary contributor component signal intensity, A2: gradient of transition region, x02: half point)

(However, in Equation 2, A2 is 1.8~2.0, and x02 is 2.5~2.7)

$$f3(x3) = \frac{1}{1+e^{-A3(x3-x03)}} \quad \text{[Equation 3]}$$

(x3: secondary contributor component mix rate, A3: gradient of transition region, x03: half point) (However, in Equation 3, A3 is 9.3~9.5, and x03 is 0.5~0.7)

[42] The method according to [41], which is the method for calculating fidelity for non-invasive prenatal testing to assess the risk of disease.

[43] A program for executing a computer to perform the method according to any one of [1] to [42].

[44] A recording medium on which the program according to [43] is recorded.

[45] A memory unit with the following model functions recorded:

the model function created by the method according to any one of [1] to [26], the model function in any of the following equations 1~3, or the model function of multiplication that is created by multiplying two or more model functions selected from the model functions in the following equations 1~3.

$$f1(x1) = \frac{1}{1+e^{-A1(x1-x01)}} \quad \text{[Equation 1]}$$

(x1: the first principal component, A1: gradient of transition region, x01: half point) (However, in Equation 1, A1 is 15.4~15.6, and x01 is −0.8~−0.6)

$$f2(x2) = \frac{1}{1+e^{-A2(x2-x02)}} \quad \text{[Equation 2]}$$

(x2: secondary contributor component signal intensity, A2: gradient of transition region, x02: half point)

(However, in Equation 2, A2 is 1.8~2.0, and x02 is 2.5~2.7)

$$f3(x3) = \frac{1}{1 + e^{-A3(x3-x03)}} \quad \text{[Equation 3]}$$

(x3: secondary contributor component mix rate, A3: gradient of transition region, x03: half point) (However, in Equation 3, A3 is 9.3~9.5, and x03 is 0.5~0.7)

[46] A fidelity calculation system for preparing the processing unit that executes the method according to any one of [27] to [33] and [40] to [42], and the storage unit with the following model functions recorded:

the model function created by the method according to any one of [1] to [26], the model function in any of the following equations 1~3, or the model function of multiplication that is created by multiplying two or more model functions selected from the model functions in the following equations 1~3, $$f1(x1) = \frac{1}{1 + e^{-A1(x1-x01)}} \quad \text{[Equation 1]}$$

(x1: the first principal component, A1: gradient of transition region, x01: half point) (However, in Equation 1, A1 is 15.4·15.6, and x01 is −0.8—0.6)

$$f2(x2) = \frac{1}{1 + e^{-A2(x2-x02)}} \quad \text{[Equation 2]}$$

(x2: secondary contributor component signal intensity, A2: gradient of transition region, x02: half point) (However, in Equation 2, A2 is 1.8~2.0, and x02 is 2.5~2.7)

$$f3(x3) = \frac{1}{1 + e^{-A3(x3-x03)}} \quad \text{[Equation 3]}$$

(x3: secondary contributor component mix rate, A3: gradient of transition region, x03: half point) (However, in Equation 3, A3 is 9.3~9.5, and x03 is 0.5~0.7)

[47] The fidelity calculation system according to [46], wherein the exclusion condition C1 created by the method according to [34] and/or the exclusion condition C2 created by the method according to [35] are recorded in the aforementioned storage section, and the aforementioned processing section executes the method according to [40].

THE EFFECTS OF THE INVENTION

According to the method for creating a model function in the present invention, a model function for calculating the fidelity of the secondary contributor component signal in the analysis data of a nucleic acid mix sample containing a small ratio of secondary contributor nucleic acids, such as cffDNA, ctDNA, and ddcfDNA, can be created.

According to the method for calculating the fidelity in the present invention, the fidelity of the secondary contributor component signal in the analysis data of a nucleic acid mix sample containing a small ratio of secondary contributor nucleic acids, such as cffDNA, ctDNA, and ddcfDNA, can be calculated.

In addition, according to the method for setting the exclusion conditions in the present method, exclusion conditions for determining which of the data sets should be excluded can be set, in order to narrow down the data of predictor variables to be input to the aforementioned model function.

BRIEF DESCRIPTION OF THE FIGURES

FIG. 4 The distribution diagram of the fidelity calculated in Test Example 2. The left panel shows the aggregated fidelity for SNPs of mutually nonidentical genotypes that are homozygous for each parent. The right panel shows the aggregated fidelity for mutually identical SNPs that are homozygous for each parent.

FIG. 7 The distribution diagram of fidelity calculated in Test Example 4. The upper left panel shows the aggregated fidelity for SNPs of mutually nonidentical genotypes that are homozygous for each parent. The upper right panel shows the aggregated fidelity for mutually identical SNPs that are homozygous for each parent. The lower left shows the aggregated fidelity for SNPs of mutually nonidentical genotypes that are homozygous for each parent, and the absolute value of the secondary contributor component signal intensity is zero. The lower right panel shows the aggregated fidelity for mutually identical SNPs that are homozygous for each parent, and the absolute value of the secondary contributor component signal intensity is zero.

The distribution diagrams of fidelity corresponding to SNPs homozygous to mother are aggregated, regardless of father's genotype and true/false of the presence of the secondary contributor component signal.

Figure 10:
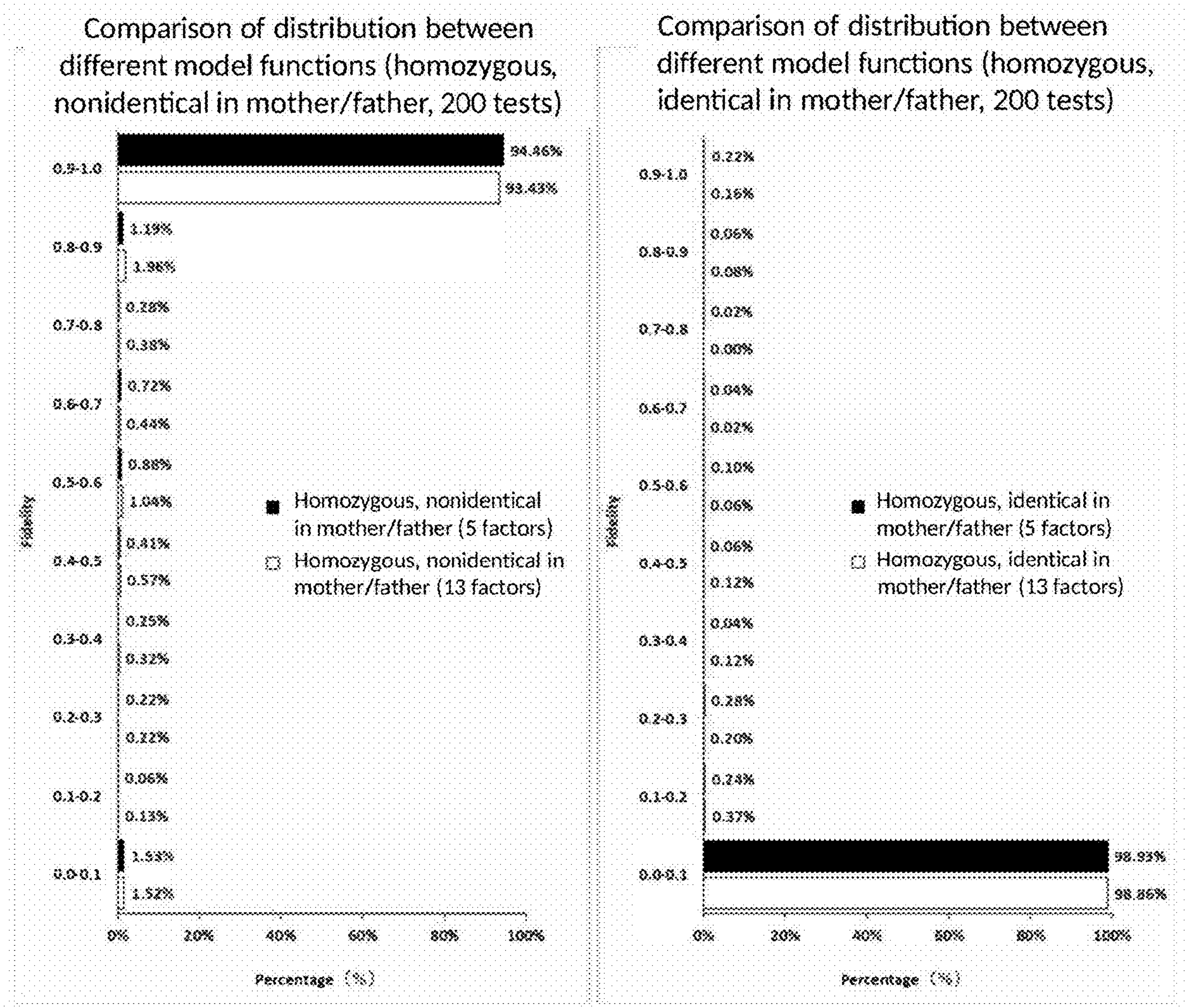

FIG. 10 The distribution diagram of fidelity calculated in Test Example 2 and Test Example 8. The left shows the aggregated fidelity for SNPs of mutually nonidentical genotypes that are homozygous for each parent (the fetal genotype is heterozygous). The right shows the aggregated fidelity for mutually homozygous SNPs that are homozygous for each parent.

Figure 11:
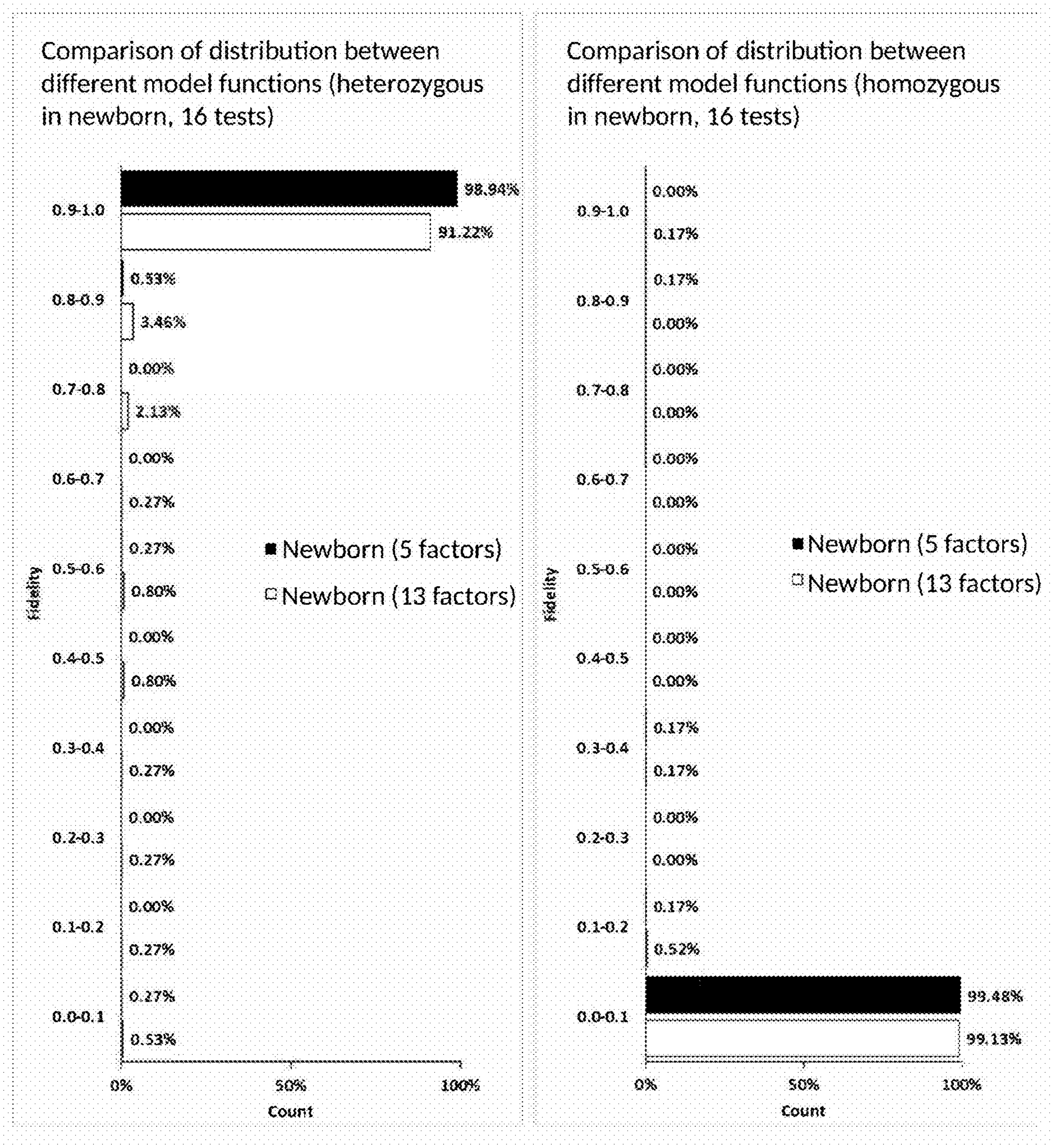

FIG. 11 The distribution diagram of fidelity calculated in Test Example 6 and Test Example 9. The right shows the aggregated fidelity for heterozygous SNPs of the new born, which are homozygous for the mother. The right shows the aggregated fidelity for homozygous SNPs of the newborn, which are homozygous for the mother.

THE FORM OF IMPLEMENTING THE INVENTION

In the following, the description on the specific implementation form of the present invention will be explained, in the order of the method for creating model functions, the method for calculating fidelity, and the method for setting exclusion conditions in the present invention. In addition, the scope of the present invention is not limited to the specific implementation forms according to the following.

<1> Method for Creating Model Functions

The following is a detailed description on the implementation form of the method for creating model functions in the present invention. In the "<1-1> Overview" section, an overview of the method for creating model functions in the present invention is described. In the "<1-2> Prenatal Genetic Testing" section, prenatal genetic testing and its applications are explained in detail; in the "<1-3> Cancer Testing" section, cancer testing and its applications are explained in detail; in the "<1-4> Transplant Organ engraftment Monitoring" section, transplant organ engraftment monitoring and its applications are explained in detail.

<1-1> Overview

The method for creating model functions in the present invention comprises step A-1, step A-2, step A-3-1, and step A-4-1 as essential steps. The steps are described below one by one.

[Step A-1]

Step A-1 is the step of preparing a data set obtained by measuring a nucleic acid mix sample.

"The nucleic acid mix sample" is a sample that contains genetic information of multiple contributors. The genetic information includes that encoded in DNA as well as RNA.

Nucleic acid mix sample includes samples that contain cfDNA and cfRNA, specifically whole blood, plasma, serum, and urine. It is more preferable to use whole blood, plasma, and serum.

The nucleic acid mix sample contains primary and secondary contributor nucleic acids with genetic information from the primary and secondary contributor, respectively. In addition, the ratio of the primary and secondary nucleic acids in the nucleic acid mix sample can vary depending on the status of the primary and secondary contributors.

The "primary contributor" here refers to the mother in the case of prenatal genetic testing, the test subject in the case of cancer testing, and the recipient in the case of transplant organ engraftment monitoring. In other words, "primary contributor" refers to the individual from whom the nucleic acid mix sample was obtained.

The "primary contributor nucleic acid" refers to the nucleic acids with genetic information from the aforementioned primary contributor. Primary contributor nucleic acids include maternal genomic DNA, or the fragment or transcripts the maternal genomic DNA (cfDNA or cfRNA of the mother's origin) in the case of prenatal genetic testing; genomic DNA of the test subject, or the fragment or transcripts of the genomic DNA of the test subject (cfDNA or cfRNA of the test subject's origin) in the case of cancer testing; genomic DNA of the recipient of organ transplant, or the fragment or RNA transcripts from the genomic DNA of the recipient (cfDNA or cfRNA of the recipient's origin) in the case of transplant engraftment monitoring.

The "secondary contributor" refers to the fetus in the case of prenatal genetic testing, cancer cells in the case of cancer testing, and the transplanted organ in the case of transplant organ engraftment monitoring. In other words, "secondary contributor" refers to the individual, tissue, or cell that exists within the body of the primary contributor and has different genetic information from the primary contributor.

The "secondary contributor nucleic acid" refers to the nucleic acids with genetic information from the aforementioned secondary contributor. Secondary contributor nucleic acids include genomic DNA of the fetus, or the fragments or transcripts of the genomic DNA of the fetus (cfDNA or cfRNA of the fetus' origin) in the case of prenatal genetic testing; genomic DNA of the cancer cells, or the fragments or transcripts of the genomic DNA of the cancer cells (cfDNA or cfRNA of the cancer cell's origin) in the case of cancer testing; genomic DNA of the transplanted organ, or the fragment or transcripts of the genomic DNA of the transplanted organ (cfDNA or cfRNA of the transplanted organ's origin) in the case of transplant organ engraftment monitoring.

Moreover, since the method for creating model function in the present invention simply aims to just create a model function, the nucleic acid mix sample containing the primary and secondary contributor nucleic acids can be artificial made. For example, nucleic acid mix sample can be made by adding nucleic acids imitating the secondary contributor nucleic acids to the blood that contains the primary contributor nucleic acids.

The data set obtained in step A-1 includes the data sets containing signals that indicate the presence of each allele at multiple polymorphic genetic loci in the primary and secondary contributor nucleic acids. Here, the number of polymorphic genetic loci included in the data set is not particularly limited, but is preferably 5 or above, more preferably 10 or above, even more preferably 15 or above, and even more preferably 18 or above.

This data set is not particularly limited as long as it is obtained by an analytical method that can detect each allele at polymorphic genetic loci separately. Such analytical method is preferably the method that can detect single nucleotide substitutions (SNPs) at polymorphic genetic loci separately.

For example, the analytical method of nucleotide sequencing analysis in any of it's forms, digital PCR, microarrays, and real-time PCR, which are used for the detection of SNPs.

Nucleotide sequencing can be next-generation sequencing (NGS). Next-generation sequencing is the sequencing method that allows parallel sequencing of a large number of clonally amplified molecules and single nucleic acid molecules. In the present invention, any NGS system can be used. For example, the following can be used: pyrosequencing (e.g. GS Junior (Roche)), sequencing by synthesis using reversible dye terminators (e.g. MiSeq (Illumina)), ligation sequencing (e.g. SegStudio Genetic Analyzer (Thermo Fisher SCENTIFIC)), ion semiconductor sequencing (e.g. Ion Proton System (Thermo Fisher SCENTIFIC)), sequencing by CMOS (complementary metal oxide semiconductor) chip (e.g. iSeq 100 System (Illumina)).

The sequence data read by next-generation sequencing can be analyzed, and the number of reads of the allele with specific sequences (specific SNPs) at polymorphic genetic loci can be interpreted as the signal indicating the presence of the allele of concern.

In addition, in the stage of synthesizing the library for next generation sequencing, the number of unique molecular tag (UMT) identifying an allele as having a specific sequence (specific SNPs) at a polymorphic genetic locus can be interpreted as a signal indicating the presence of the allele of concern, when barcode sequences (Unique Molecular Identifiers (UMI), Unique Molecular Tag (UMT)) that enable individual identification of nucleic acid molecules are added to the nucleic acid fragment to be analyzed.

When employing next generation sequence as the analysis method in the present invention, it is preferable to employ a target sequencing method that specifically amplifies polymorphic genetic loci that are known in advance.

Digital PCR is the method in which the sample is distributed to multiple wells so that each well contained about one nucleic acid molecule, and PCR is performed individually for each well. In a well that contains the target sequence, PCR amplification proceeds and a fluorescent signal is detected, but in a well that does not contain the target sequence, PCR amplification does not proceed and a fluorescent signal is not detected. After PCR, whether there is the amplifications signal "with (+)/without (−)" in each well or not can be determined and the number of wells with the signal "with (+)" is calculated as the copy number of the target.

In the case where probes that can accurately identify mutations such as SNPs (TaqMan®> probes, cycling probes, etc.) is used in digital PCR, fluorescence is observed only in wells where alleles with specific sequences (specific SNPs) are amplified. By designing fluorescently labeled probes with different emission wavelengths for each allele, different alleles at a single polymorphic genetic locus can be detected separately by distinguishing each with fluorescent colors. The number of wells with the fluorescence signal "with (+)", corresponding to a certain allele, can be interpreted as the signal indicating the presence of the allele.

Microarray is the method of having DNA, DNA fragments, cDNA, oligonucleotides, RNA, or RNA fragments with known sequences as probes, solidifying hundreds~hundreds of thousands of probes, and detecting fluorescent labeling that is detected when nucleic acids with complementary sequences are hybridized to the probes.

If more than one allele is at one locus, each allele can be solidified individually to detect them separately. The fluorescence intensity at the point, at which a specific allele is solidified, can be interpreted as the signal indicating the presence of the allele. SNP array indicate micro array for genotyping of SNP.

Real-time PCR is the method to monitor and analyze the fluorescence produced by the PCR amplification of nucleic acids in real time using a spectrophotometer. It is preferable to combine real-time PCR with probes that can accurately determine mutations, such as SNPs (TaqMan® probes, cycling probes, etc.). By designing fluorescent-labeled probes with different emission wavelengths for each allele, different alleles at a single polymorphic genetic locus can be distinguished by their fluorescent colors.

When trying to obtain a data set by a real-time PCR method, it is preferable to employ multiplex PCR to improve the efficiency. Multiplex PCR is the method that uses multiple sets of primers to amplify multiple target sequences at once in a single reaction system.

In real-time PCR, the intensity of the fluorescent signal corresponding to a specific allele can be interested as the signal indicating the presence of the allele.

Mass spectrometry is an analytic method that measures the mass of an ion or a molecule, by ionizing the molecule and measuring its mass-to-charge ratio (m/z). Although it is essentially a method to measure the mass of a molecule, if the mass of a nucleic acid molecule prepared under specific conditions (e.g., PCR using specific primers or cleavage of a nucleic acid molecule with specific restriction enzymes) can be measured, the mass of the molecule can be checked against the database and the sequence of the detected nucleic acid molecule can be identified. For this reason, mass spectrometry is widely applied to genotyping.

In mass spectrometry, the ion intensity at m/z specific to the sequence containing a specific allele can be interpreted as a signal indicating the presence of the allele.

The data set obtained in step A-1 requires the authenticity of the signal indicating the presence of the allele described above to be known in prior. In other words, when a signal indicating the presence of a specific allele is detected, whether the nucleic acid mix sample contains the primary acid or secondary contributor nucleic acid with the sequence of the allele or not, needs to be known in prior.

In addition, step A-1 is the step for preparing the data set. Therefore, the nucleic acid analysis process for obtaining the primary data set is not essential in the present invention. In other words, the specific implementation of step A-1 includes the form in which the experimenter of the present invention himself prepares the abovementioned data set by acquiring primary data through nucleic acid analysis, but is not limited to it. The specific implementation of step A-1 includes the form in which the person other than the implementer of the present invention prepares the abovementioned data set by secondarily acquiring the data set that was primarily acquired by nucleic acid analysis.

[Step A-2]

Step A-2 is the step of performing principal component analysis on the data in the data set described above. Specifically, one or more composite variables are produced by linearly combining a numerical group that includes the following (A1) and (A2), for the polymorphic genetic loci at which the signals indicating the presence of alleles derived from the aforementioned primary and aforementioned secondary contributor nucleic acids among the multiple polymorphic genetic loci from the data of the aforementioned data set are detected separately.

(A1) is secondary contributor component signal intensity. Secondary contributor component signal intensity is the intensity of the signal derived from the secondary contributor nucleic acid, which indicates the presence of alleles at specific polymorphic genetic loci.

It is convenient to confirm which of the signal indicating the presence of two different alleles detected separately in the analysis of a nucleic acid mix sample is derived from the primary nucleic acid, and which is derived from the secondary nucleic acid.

In most cases, circulating cell-free nucleic acid samples contain more primary nucleic acids than secondary nucleic acids that the intensity of the secondary contributor component signal is weaker than the intensity of the primary contributor component signal described above. Hence, in such case, the signal with weaker intensity can be regarded as the secondary contributor component signal.

On the other hand, for example, the ratio of maternal nucleic acids to fetal nucleic acids in late pregnancy, or the ratio of nucleic acids from a cancer patient to nucleic acids from cancer cells in advanced stage of cancer, can be the opposite of a normal case. In other words, the amount of secondary nucleic acids in a circulating cell-free nucleic acid sample may be equal to or greater than the amount of primary nucleic acids. In such a cases, the genotype of the primary contributor can be identified by genotyping the samples in advance, and then comparing it with the analysis result of the nucleic acid mix sample. This enables to determine which of the signals indicating the presence of the two alleles, which are detected separately from the nucleic acid mix sample analysis, is derived from the primary nucleic acid and which is derived from the secondary nucleic acid.

Depending on the type of measurement method used to obtain the primary data set and software used to process the obtained data, there can be a wide range of units and expressions to refer to the secondary contributor component signal intensity. In the present invention, the term "secondary contributor component signal intensity" encompasses all of the numerical values that reflect the signal intensity indicating the presence of alleles at specific polymorphic genetic loci derived from the secondary contributor nucleic acid. In other words, in addition to numerical values that directly represent the signal intensity, all numerical values that reflect the signal intensity, such as the numerical value multiplied by a constant, or the power value and power root of the numerical value, are included in the term "secondary contributor component signal intensity".

For example, the standardized value of the original data of the secondary contributor component signal intensity can also be referred to as "secondary contributor component signal intensity". The details of the standardization will be described later.

In addition, "secondary contributor component signal intensity" can also refer to the numerical value that is obtained by processing the original data of the secondary contributor component signal intensity based on the other detected parameters. Noise is one of the "other detected parameters" that are used to process the original data of the secondary contributor component signal intensity. The definition of noise will be described later.

For example, the numerical value obtained by subtracting the noise intensity or its average value at the multiple polymorphic loci analyzed from the original data of the secondary contributor component signal intensity, can also be referred to as the "secondary contributor component signal intensity". The denominator for calculating the average value of the noise intensity can be the number of polymorphic loci from which the noise is detected, or the number of all polymorphic loci that are analyzed.

In specific, the average value of the aforementioned noise intensity may be uniformly subtracted from the original data of the secondary contributor component signal intensity without distinguishing the polymorphic loci, from which the noise is detected and those from which the noise is not detected.

It is also possible to subtract the average value of the aforementioned noise intensity from the original data of the secondary contributor component signal intensity, only for the specific polymorphic loci at which the noise is detected.

The noise intensity detected from the specific polymorphic locus may also be subtracted from the secondary contributor component signal intensity of the specific polymorphic loci from which the noise is detected.

Also, the secondary contributor component signal intensity indicating the presence of alleles at the aforementioned specific polymorphic loci, may also be divided by the average value of the noise intensities at the polymorphic genetic loci among the aforementioned multiple polymorphic loci.

In other words, the following equation may be used as the "secondary contributor component signal intensity".

(Secondary contributor component signal intensity)/(Average noise intensity)

Hence, when referring to "secondary contributor component signal intensity," it is referring to not only one type of value, but multiple types of values. Therefore, the numerical group, which is the subject of linear combination in step A-2, can include only one type of "secondary contributor component signal intensity", or two or more types of "secondary contributor component signal intensities".

(A2) is secondary contributor component mix rate. Secondary contributor component mix rate is the ratio of the secondary contributor component signal intensity to the total signal intensity derived from alleles at specific polymorphic genetic loci. In other words, it can be expressed by the formula: "Secondary contributor component mix rate=Secondary contributor component signal intensity/Total signal intensity."

For the equivalent reason as explained in (A1) above, secondary contributor component mix rate can have a wide range of units and expressions. In the present invention, the term "secondary contributor component mix rate" encompasses all of the numerical values that reflect the signal intensity indicating the presence of alleles at specific polymorphic genetic loci derived from the secondary contributor nucleic acid. In other words, in addition to numerical values that directly represent the signal intensity, all numerical values that reflect the signal intensity, such as the numerical value multiplied by a constant, or the power value and power root of the numerical value, are included in the term "secondary contributor component mix rate".

For example, the standardized value of the original data of the secondary contributor component mix rate can also be referred to as "secondary contributor component mix rate." The details of the standardization will be described later.

In addition, "secondary contributor component mix rate" can also refer to the numerical value that is obtained by processing the original data of the secondary contributor component mix rate based on the other detected parameter. Noise is one of the "other detected parameters" that are used to process the original data of the secondary contributor component mix rate. The definition of noise will be described later.

For example, the numerical value obtained by subtracting the ratio of the noise intensity (noise mix rate) or its average value at the multiple polymorphic loci analyzed from the original data of the secondary contributor component mix rate, can also be referred to as the "secondary contributor component mix rate". The denominator for calculating the average value of the noise mix rate can be the number of polymorphic loci from which the noise is detected, or the number of all polymorphic loci that are analyzed.

In specific, the average value of the aforementioned noise mix rate may be uniformly subtracted from the original data of the secondary contributor component mix rate without distinguishing the polymorphic loci, from which noise is detected and those from which noise is not detected.

It is also possible to subtract the average value of the aforementioned noise mix rate from the original data of the secondary contributor component mix rate, only for the specific polymorphic loci where the noise is detected.

The noise mix rate of the noise intensity detected from the specific polymorphic loci may also be subtracted from the secondary contributor component noise intensity of the specific polymorphic locus from which the noise is detected.

Also, the secondary contributor component mix rate indicating the presence of alleles at the aforementioned specific polymorphic loci, may also be divided by the average value of the noise intensities at the polymorphic genetic loci among the aforementioned multiple polymorphic loci.

In other words, the following equation may be used as the "secondary contributor component mix rate".

(Secondary contributor component mix rate)/(Average noise intensity)

Hence, when referring to "secondary contributor component mix rate," it is referring to not only one type of value, but multiple types of values. Therefore, the numerical group, which is the subject of linear combination in step A-2, can include only one type of "secondary contributor component mix rate", or two or more types of "secondary contributor component mix rate."

The numerical group that is the subject of linear combination in step A-2 can include numerical values other than those in (A1) and (A2) described above. In other words, other than (A1) and (A2) that are related to specific polymorphic genetic loci, linear combination can be performed on a numerical group that contains various measured or calculated values for the specific polymorphic genetic loci.

The following explains numerical values (A3)~(A5) that can be included in the numerical group subject to linear combination. Furthermore, only one type selected from (A3)~(A5) below can be included in the aforementioned numerical group, or two or more types arbitrarily selected can be included in the aforementioned numerical group. All of (A3)~(A5) can be included in the aforementioned numerical group as well.

(A3) is primary contributor component signal intensity. Primary contributor component signal intensity is the intensity of the signal derived from the primary contributor nucleic acid, which indicates the presence of the allele at specific polymorphic genetic loci.

As mentioned above, since circulating cell-free nucleic acid samples contain more primary contributor nucleic acids than the secondary contributor nucleic acids in most cases, the intensity of the primary contributor component signal is stronger than the intensity of the secondary contributor component signa. Hence, in such case, the signal with stronger intensity can be considered as the primary contributor component signa.

On the other hand, for example, the ratio of maternal nucleic acids to fetal nucleic acids in late pregnancy, or the ratio of nucleic acids from a cancer patient to nucleic acids from cancer cells in advanced stage of cancer, can be the opposite of a normal case. In other words, the amount of secondary nucleic acids in a circulating cell-free nucleic acid sample may be equal to or greater than the amount of primary nucleic acids. In such a cases, the genotype of the primary contributor can be identified by genotyping the samples in advance, and then comparing it with the analysis result of the nucleic acid mix sample. This enables to determine which of the signals indicating the presence of the two alleles, which are detected separately from the nucleic acid mix sample analysis, is derived from the primary nucleic acid and which is derived from the secondary nucleic acid.

For the equivalent reason as explained in (A1) above, in addition to the numerical value that directly represent the signal intensity, all numerical values that reflect the signal intensity, such as the numerical value multiplied by a constant, or the power value and power root of the numerical value, are included in the term "primary contributor component signal intensity". The numerical group, which is the subject of linear combination in step A-2, can include only one type of "primary contributor component signal intensity", or two or more types of "primary contributor component signal intensities".

(A4) is primary contributor component mix rate. Primary contributor component mix rate is the ratio of the primary contributor component signal intensity to the total signal intensity derived from alleles at specific polymorphic genetic loci. In other words, it can be expressed by the formula: "Primary contributor component mix rate=Primary contributor component signal intensity/Total signal intensity."

For the equivalent reason as according to (A2) above, in addition to the numerical values that directly express the ratio, all numerical values that reflect the ratio, such as the numerical value multiplied by a constant, or the power value and power root of the numerical value, are included in the term "primary contributor component mix rate". The numerical group, which is the subject of linear combination step A-2, can include only one type of "primary contributor component mix rate", or two or more types of "primary contributor component mix rates".

(A5) is the Noise.

Consider a situation where, for biological, genetic, or test system reasons, the signal indicating base "A" or base "G" can be observed at a specific single nucleotide polymorphism locus, but a signal indicating base "T" and base "C" cannot be observed. An example of such a situation is the situation, at which the aforementioned specific single nucleotide polymorphism in a fetus with the father homozygous for "A" and the mother homozygous for "G" at a single nucleotide polymorphism locus is observed (it is not usual for a fetus to have "T" and "C" at the specific single nucleotide polymorphism locus). In such a situation, if signals indicating "T" and "C", which are bases that cannot be observed normally, are observed, the signals are defined as "noise" in the present invention.

In other words, noise can be obtained by subtracting the aforementioned primary contributor component signal intensity and the aforementioned secondary contributor component signal intensity, from the sum of the signal intensities derived from the allele at specific polymorphic genetic loci. Therefore, noise can be expressed by the following formula: "Sum of signal intensities−(Primary contributor component signal intensity+Secondary contributor component signal intensity)".

As mentioned above, the data set prepared in step A-1 is a set of data on multiple polymorphic genetic loci. Therefore, the data set obtained in step A-1 can of contain multiple sets of data consisting (A1) and (A2) above, and other numerical data for specific polymorphic genetic loci as one set.

Also, it is preferable that the numerical data in the numerical group to be linearly combined is standardized. The standardized data can be obtained using the following formula.

Standardized data=[(Original data)−(Mean value)]/(Sample standard deviation)

"Polymorphic genetic loci at which the signals indicating the presence of alleles derived from the primary and secondary contributor nucleic acids are detected separately" refers to polymorphic genetic loci at which the signal indicating the presence of alleles derived from the primary contributor nucleic acid and the signal indicating the presence of alleles derived from the secondary contributor nucleic acid are not mixed.

For example, in the case of prenatal genetic testing, if the mother is heterozygous for allele A and allele B at specific polymorphic genetic loci, the analysis of cfDNA always detects the signals of allele A and allele B that are derived from the mother's genomic DNA, regardless of the father's genotype. Either of the signals of allele A and allele B is mixed with the signal derived from the cffDNA, but it cannot be distinguished from the signal derived from the mother's genomic DNA. If such data is added to the basis of the analysis, the accuracy of the model function is degraded.

In addition, in the case of cancer testing, if the test subject is homozygous or heterozygous for a congenital cancer-associated mutation, the mutation is always in the ctDNA. Therefore, the signal derived from the test subject is mixed with the signal derived from cancer cells. If such data are added to the basis of the analysis, the accuracy of the model function is degraded.

In the case of the transplant organ engraftment monitoring, if the recipient is heterozygous for allele A and allele B at specific polymorphic genetic loci, the analysis of cfDNA always detects the signals of allele A and allele B derived from the recipient's genomic DNA, regardless of the donor's genotype. Either of the signals of allele A and allele B is mixed with the signal derived from donor cfDNA, but it cannot be distinguished from the signal derived from the recipient's genomic DNA. If such data is added to the basis of the analysis, the accuracy of the model function is degraded.

Therefore, in step A-2, the polymorphic genetic loci to be analyzed are limited to "polymorphic genetic loci at which the signals indicating the presence of alleles derived from the primary and secondary contributor nucleic acids are detected separately". In other words, the polymorphic genetic loci analyzed in step A-2 should be polymorphic genetic loci at which the signal indicating the presence of alleles derived from the secondary contributor nucleic acid cannot be mixed with the signal indicating the presence of alleles derived from the primary contributor nucleic acid.

In step A-2, one or more composite variables are produced by linearly combining the numerical group described above. The principal component analysis is a good example of a linear combination method. In addition, the composite variables can be produced by other methods. Even if the composite variables are produced by other method, it is preferable that they are composite variables that can be produced by principal component analysis.

The composite variables produced by linear combination can be presented as the following first-degree polynomial. Here, n is an integer greater than or equal to 2 that represents the number of types of numerical values in the data set, which are included in the numerical group that is the subject of linear combination. $X_n$ is the numerical value in the numerical group that is the subject of linear combination, and au, is the coefficient that weights the numerical values to be linearly combined.

$$Z1=a11X1+a12X2+\ldots+a1nXn$$

In the preferable implementation form of the present invention, the secondary contributor component signal intensity or secondary contributor component mix rate is weighted to the maximum in the first-degree polynomial representing the composite variables.

The number of composite variables that can be produced increases with the number of types of numerical values included in the numerical that is the subject of linear combination. The number of composite variables produced in step A-2 is not particularly limited.

The implementation form in which the composite variables are produced by linear combination of a numerical group including at least (A1) and (A2) was explained above, but the composite variables can be produced by nonlinear combination of the aforementioned numerical group. Here, nonlinear combination refers to the power of each numerical value, the product of each numerical value, and functions with these kinds of numerical values as exponents.

The composite variable obtained by linear combination in step A-2 has a correlation with fidelity. The correlation is used to create a model function. The specific process in the present invention is as according to the following step A-3-1 and step A-4-1.

[Step A-3-1]

Step A-3-1 is the step of assigning the fidelity to the composite variables produced by linear combination.

The composite variables used in step A-3-1 are not particularly limited, but the composite variables that best reflect the numerical group that is the subject of the linear combination are preferable. In other words, it is preferable to use a composite variable with the highest contribution to the numerical group that is the subject of linear combination. This corresponds to the first principal component in the principal component analysis.

In step A-3-1, the composite variables produced by linear combination is first divided into multiple categories. In other words, the composite variables are divided into multiple categories according to the size of their numerical values.

The method of categorization is not particularly limited. Although the composite variables can be divided at equal intervals according to size, it is preferable to divide the composite variables in a way that the produced composite variables are included in all categories. Furthermore, it is more preferable to divide the composite variables exponentially according to size instead of linearly. This is because the produced composite variables and probabilities become a sigmoid curve when regressed on a curve.

The number of categories is not limited, but it is preferable to divide into 3 or above, more preferably 5 or above, even more preferable 7 or above, even more preferable 10 or above, even more preferable 12 or above, even more preferable 15 or above, or even more preferable 18 or above categories.

The next step is to determine the ratio of true secondary contributor component signal intensities corresponding to the composite variables in each category. In other words, the ratio of composite variables corresponding to the true secondary contributor component signal intensities among all the composite variables in each category is obtained. In this patent application, this ratio is referred to as "probability".

In addition, secondary contributor component signal intensity indicates the presence of a specific allele at a polymorphic genetic locus in the secondary contributor nucleic acid. If the specific allele is actually present in the secondary contributor nucleic acid as indicated by the secondary contributor component signal intensity, it is considered "true".

After obtaining the probability of each category of the composite variables, it is assigned as the probabilty corresponding to the composite variables in each category. Specifically, the probability of each category is assigned to the value of one composite variable that represents the category. This step enables to create a scatter plot of the composite variables and the probability.

[Step A-4-1]

In step A-4-1, regression analysis is performed on the composite variables in each category, and the fidelity corresponding to the composite variables in each category described above. By doing so, a model function with the composite variable as the predictor variable and the fidelity as the objective variable, for calculating the fidelity is obtained.

"Probability" and "fidelity" values are in a corresponding relationship. In this patent application, the parameter used to create a model function is referred to as "probability", and the parameter calculated by inputting predictor variables into the model function is referred to as "fidelity".

The method of regression analysis in step A-4-1 is not particularly limited, but the least-squares method is preferable.

The model function is a sigmoid function. If the composite variable is the first principal component in the principal component analysis, the model function can be expressed by Equation 1 below.

$$f1(x1) = \frac{1}{1 + e^{-A1(x1 - x01)}} \quad \text{[Equation 1]}$$

(x1: the first principal component, A1: gradient of transition region, x01: half point)

The present invention is not limited to Equation 1 above, and it is preferable to create a model function in the form of a sigmoid function with two parameters, for calculating the fidelity. A1 and x01 in Equation 1 corresponds to the parameters.

In equation1, A1 is preferably between 15.4 and 15.6, and more preferably 15.5. Also, x01 is preferably between −0.8 and −0.6, and more preferably −0.9. Note that the specified ranges above include the values that are rounded to the second decimal place.

The model functions obtained by the method described above have high versatility. It can be applied to the analysis of data sets that have been primarily obtained under conditions different, from the condition in which the data set was obtained in step A-1. For example, the model function can be applied to calculate the fidelity of the data set that was primarily obtained under the condition that is different in terms of sample volume and concentration, the analysis of polymorphic genetic loci, and the type of signal (number of reads or UMT count), etc, from the condition in which the data set was obtained in step A-1.

In other words, there is no need to create a new model function to calculate the fidelity of a data set obtained under a different condition. Once the model function is created using the method according to the present invention, it can be used for the analysis of data sets obtained under different conditions.

In addition, the data sets used as the basis of creating the model function can be applied to the analysis of a data set that was obtained by a different type of test. For example, a model function created based on a data set that was obtained from a prenatal genetic test, can also be used for the analysis of a data set that was obtained from a cancer test or transplant organ engraftment monitoring.

It is preferable that the type and the number of numerical values in the numerical group used for the linear combination to create the model function, are equivalent to the type and the number of numerical values in the numerical group used for the linear combination to produce composite variables input to the model function.

The method for creating a model function based on the correlation between composite variables and fidelity was described above, but the present invention further provides a model function for calculating fidelity that has other parameters as the predictor variable. The present invention also relates to the method for creating the following model functions f2(x2) and f3(x3). The methods for creating the respective model functions are described below in detail.

First, the method for creating the model function f2(x2) is explained. This method comprises step A-1, step A-3-2, and step A-4-2. The explanation on step A-1 is as described above. Step A-3-2 and step A-4-2 are described below.

[Step A-3-2]

In step A-3-2, (A1) secondary contributor component signal intensity described above is first divided into multiple categories. In other words, (A1) secondary contributor component signal intensity is divided into multiple categories according to the size of the numerical values.

The method of categorization is not particularly limited. Although the secondary contributor component signal intensities can be divided at equal intervals according to size, it is preferable to divide the secondary contributor component signal intensities in a way that the secondary contributor component signal intensities are included in all categories. Furthermore, it is more preferable to divide the secondary contributor component signal intensities exponentially according to size instead of linearly. This is because the secondary contributor component signal intensities and probabilities become a sigmoid curve when regressed on a curve.

The number of categories is not limited, but it is preferable to divide into 3 or above, more preferably 5 or above, even more preferable 7 or above, even more preferable 10 or above, even more preferable 12 or above, even more preferable 15 or above, or even more preferable 18 or above categories.

The next step is to determine the ratio of true secondary contributor component signal intensities corresponding to the secondary contributor component signal intensities in each category. In other words, the ratio of true secondary contributor component signal intensities among all the secondary contributor component intensities in each category is obtained. In this patent application, this ratio is referred to as "probability".

In addition, secondary contributor component signal intensity indicates the presence of a specific allele at a polymorphic genetic locus in the secondary contributor nucleic acid. If the specific allele is actually present in the secondary contributor nucleic acid as indicated by the secondary contributor component signal intensity, it is considered "true".

After obtaining the probability of each category of the secondary contributor component signal intensities, it is assigned as the fidelity corresponding to the secondary contributor component signal intensities in each category. Specifically, the probability of each category is assigned to the value of one secondary contributor component signal intensity that represents the category. This step enables to create a scatter plot of the secondary contributor component signal intensities and the fidelity.

[Step A-4-2]

In step A-4-2, regression analysis is performed on the secondary contributor component signal intensities in each category described above, and the probabilities corresponding to the secondary contributor component signal intensities in each category. By doing so, the model function f2(x2) with the secondary contributor component signal intensity as the predictor variable x2 and the fidelity as the objective variable, for calculating the fidelity is obtained. The method of regression analysis in step A-4-2 is not particularly limited, but the least-squares method is preferable.

The model function f2(x2) is a sigmoid function, and it can be expressed by Equation 2 below.

$$f2(x2) = \frac{1}{1 + e^{-A2(x2 - x02)}} \quad \text{[Equation 2]}$$

(x2: secondary contributor component signal intensity, A2: gradient of transition region, x02: half point)

The model function f2(x2) obtained by the method described above has a high versatility, and once the model function f2(x2) is created using the method in the present invention, it can be used to analyze a data set obtained a under different condition. It can also be applied to the analysis of a data set obtained by a type of test that different from the test in which the data set to create the model function f2(x2) was obtained.

In equation 2, A2 is preferably between 1.8 and 2.0, and more preferably 1.9. Also, x02 is preferable between 2.5 and 2.7, and more preferably 2.6. Note that the specified ranges above include the values that are rounded to the second decimal place.

Next, the method for creating the model function f3(x3) is explained. This method comprises step A-3-3 and step A-4-3.

[Step A-3-3]

In step A-3-3, (A2) secondary contributor component mix rate described above is first divided into multiple categories. In other words, (A2) secondary contributor component mix rate is divided into multiple categories according to the size of the numerical values.

The method of categorization is not particularly limited. Although the secondary contributor component mix rates can be divided at equal intervals according to size, it is preferable to divide the secondary contributor component mix rates in a way that the secondary contributor component mix rates are included in all categories. Furthermore, it is more preferable to divide the secondary contributor component mix rates exponentially according to size instead of linearly. This is because the secondary contributor component mix rates and probabilities become a sigmoid curve when regressed on a curve.

The number of categories is not limited, but it is preferable to divide into 3 or above, more preferably 5 or above, even more preferable 7 or above, even more preferable 10 or above, even more preferable 12 or above, even more preferable 15 or above, or even more preferable 18 or above categories.

The next step is to determine the ratio of true secondary contributor component signal intensities corresponding to the secondary contributor component mix rates in each category. In other words, the ratio of true secondary contributor component signal intensities among all the secondary contributor mix rates in each category is obtained. In this patent application, this ratio is referred to as "probability".

In addition, secondary contributor component mix rate indicates the presence of a specific allele at a polymorphic genetic locus in the secondary contributor nucleic acid. If the specific allele is actually present in the secondary contributor nucleic acid as indicated by the secondary contributor component mix rate, it is considered "true".

After obtaining the probability of each category of the secondary contributor component mix rates, it is assigned as the fidelity corresponding to the secondary contributor component mix rates in each category. Specifically, the probability of each category is assigned to the value of one secondary contributor component mix rate that represents the category. This step enables to create a scatter plot of the secondary contributor component mix rates and the probability.

[Step A-4-3]

In step A-4-3, regression analysis is performed on the secondary contributor component mix rates in each category described above, and the probabilities corresponding to the secondary contributor component mix rates in each category. By doing so, the model function f3(x3) with the secondary contributor component mix rate as the predictor variable x3 and the fidelity as the objective variable, for calculating the fidelity is obtained. The method of regression analysis in step A-4-3 is not particularly limited, but the least-squares method is preferable.

The model function f3(x3) is a sigmoid function, and it can be expressed by Equation 3 below.

$$f3(x3) = \frac{1}{1 + e^{-A3(x3 - x03)}} \quad \text{[Equation 3]}$$

(x3: secondary contributor component mix rate, A3: gradient of transition region, x03: half point)

In equation 3, A3 is preferably between 9.3 and 9.5, and more preferably 9.4. Also, x03 is preferable between 0.5 and 0.7, and more preferably 0.6. Note that the specified ranges above include the values that are rounded to the second decimal place.

The multiple model functions described above are each useful for evaluating the fidelity of secondary contributor component signal intensities in a data set. However, even more useful model functions can be created by multiplying the model function created above by each other.

For example, two or more composite variables are produced in step A-2, and fidelity is assigned to each of the two or more composite variables in step A-3-1. Then, the two or more model functions that are independent to each other, with each of the two or more composite variables as the predictor variable, are created in step A-4-1. It is also possible to create a model function of multiplication by multiplying these model functions by each other.

In addition, two or more model functions selected from the following three model functions can be multiplied by each other to create a model function of multiplication. For the present invention, it is preferable to multiply all of the following three model functions by each other to create a model function of multiplication.

The model function created by step A-1, step A-2, step A-3-1, and step A-4-1.

The model function created by step A-1, step A-3-2, and step A-4-2.

The model function created by step A-1, step A-3-3, and step A-4-3.

In the present invention, it is preferable to use the model function created by multiplying the model functions f1(x1), f2(x2), and f3(x3) described above by each other, as shown in Equation 4 below.

$$f(x1,x2,x3)=f1(x1)*f2(x2)*\beta(x3) \quad \text{[Formula 4]}$$

<1-2> Prenatal Genetic Testing

Next, the implementation form of creating a model function from the data set obtained in prenatal genetic test will be explained. The explanations in "<1-1> Overview" section is also applicable to this implementation form. For this reason, any redundant explanation will be omitted to an appropriate degree.

In the present implementation form, the primary contributor is the mother, the secondary contributor is the fetus in the womb of the mother, and the nucleic acid mix sample is circulating cell-free nucleic acid sample collected from the mother.

Step A-1, step A-2, step A-3-1, and step A-4-1 according to "<1-1> Overview" section each correspond to step $A_1$-1, step $A_1$-2, step $A_1$-3-1, and step $A_1$-4-1, respectively, in the present implementation form. Each step is explained below.

[Step $A_1$-1]

Step $A_1$-1 is the step of preparing a data set obtained by measuring a circulating cell-free nucleic acid sample. A circulating cell-free nucleic acid sample contains primary contributor nucleic acids with genetic information from the mother and secondary contributor nucleic acids with genetic information from the fetus. Usually, a circulating cell-free nucleic acid sample contains more primary contributor nucleic acids than secondary contributor nucleic acids. On the other hand, the mix rate can be reversed in late pregnancy.

This data set contains signals indicating the presence of each allele at multiple polymorphic genetic loci in the primary and secondary contributor nucleic acids. It is preferable that the polymorphic genetic loci here are loci with single nucleotide polymorphisms (SNPs), which are used in Human Identification (HID). The known SNPs used in HID are in a database that the polymorphic genetic loci with these SNPs can be arbitrarily selected from the data base.

In addition, the authenticity of the signal indicating the presence of each allele must be known in prior. One method to identify the authenticity of the signal is to perform a definitive genetic test on the child after birth. Also, if the result of the definitive genetic testing on the biological father and mother shows that an allele is homozygous, and the genotype is identical or non-identical in the mother and the father, the genotype of the allele at the polymorphic genetic locus in the fetus can be correctly identified.

[Step $A_1$-2]

Step $A_1$-2 is the step of performing linear combination on a numerical group that includes at least aforementioned (A1) and aforementioned (A2), for the polymorphic genetic loci that are homozygous in the mother and homozygous in the father, and at which the signals indicating the presence of alleles derived from the primary contributor nucleic acids and the signals indicating the presence of alleles derived from the aforementioned secondary contributor nucleic acids are detected separately.

The signals from the maternal genomic DNA cannot contribute to both the primary and secondary contributor component signal intensities because the polymorphic genetic loci are limited to that are homozygous in the mother and the father.

[Step $A_1$-3-1]

Step $A_1$-3-1 is the step of assigning fidelity to the composite variables produced by linear combination, and all explanations in step A-3-1 above are applicable. The authenticity of the secondary contributor component signal intensity is determined as follows.

For an allele that is homozygous in the mother and homozygous in the father (biological father), and the genotype is nonidentical between the mother and the father, the secondary contributor component signal derived from the paternal allele and the allele that is homozygous in the mother should be detected separately.

Therefore, the secondary contributor component signal is considered true if the aforementioned secondary contributor component signal and the primary contributor component signal are detected separately, where else On opposite, the secondary contributor component signal is considered false if the aforementioned secondary contributor component signal and the primary contributor component signal are not detected separately.

On the other hand, for an allele that is homozygous in the mother and homozygous in the father (biological father), and the genotype is identical between the mother and the father, the secondary contributor component signal derived from the paternal allele and the allele that is homozygous in the mother cannot be detected separately.

Therefore, the secondary contributor component signal is considered false if the aforementioned secondary contributor component signal and the primary contributor component signal are detected separately, where else On opposite, the secondary contributor component signal is considered true if the aforementioned secondary contributor component signal and the primary contributor component signal are not detected separately.

[Step $A_1$-4-1]

Step $A_1$-4-1 is the step of obtaining a model function, and all explanations in step A-4-1 above are applicable.

In the present implementation as well, it is preferable to obtain the model function f2(x2) with secondary contributor component signal intensity as the predictor variable x2, and the model function f3(x3) with secondary contributor component mix rate as the predictor variable x3. For the specific method of obtaining the model functions in the present implementation, the explanations in step A-4-2 and step A-4-3 above are applicable.

In addition, in the present invention as well, the model functions created above can be multiplied by each other to create a model function of multiplication. The specific form of implementation is as described above.

<1-3> Cancer Testing

Next, the implementation form of creating a model function from the data set obtained in cancer test will be explained. The explanations in "<1-1> Overview" section is also applicable to this implementation form. For this reason, any redundant explanation will be omitted to an appropriate degree.

In the present implementation form, the primary contributor is the test subject with a health body with a normal type of allele at the polymorphic genetic locus where cancer-associated mutation is observed, and the secondary contributor is a cancer cells.

In the present invention, the nucleic acid mix sample is artificially prepared by adding the secondary contributor nucleic acid consisting of multiple nucleic acid fragments with sequence information of the polymorphic genetic loci where cancer-associated mutations have been introduced, to the nucleic acid sample collected from a test subject with a healthy body that contains the primary contributor nucleic acid with genetic information of the test subject.

More specifically, the nucleic acid mix sample artificially prepared by adding multiple nucleic acid fragments with the sequence of cancer-associated mutant allele, to the circulating cell-free nucleic acid sample collected from the test subject.

The nucleic acid mix sample can also be prepared by adding artificially synthesized nucleic acid fragments into the nucleic acid sample collected from the test subject.

Or, the nucleic acid mix sample can also be prepared by adding cancer cell lines, cancer tissues or their nucleic acid fragments, to the nucleic acid sample collected from the test subject.

The nucleic acid mix sample used in the present implementation form imitates the circulating cell-free nucleic acid sample of a cancer test subject. The mix ratio of primary contributor nucleic acid and secondary contributor nucleic acid in the nucleic acid mix sample is not particularly limited, but it is preferable to adjust it so that the primary contributor nucleic acid is more abundant than the secondary contributor nucleic acid. In other words, it is preferred to add the secondary contributor nucleic acid in the way that the signal derived from a specific locus in the secondary contributor nucleic acids is smaller than the signal derived from the locus in the primary contributor nucleic acids.

Therefore, the copy number of the secondary contributor nucleic acid added to the nucleic acid mix sample should be less than 50%, more preferably 40% or less, even more preferably 30% or less, even more preferably 20% or less, and even more preferably 10% or less of the copy number of the primary contributor nucleic acid.

Although the length of the nucleic acid fragment added to the nucleic acid mix sample is not particularly limited, as long as it contains cancer-associated mutation, it is preferable that the length is 50~500 bp, more preferably 100~300 bp, and even more preferably 120~200 bp.

Many polymorphic genetic loci with cancer-associated mutations, especially single nucleotide substitution mutations, are already known and compiled in a database. Multiple cancer-associated single nucleotide substitution mutations can be arbitrarily selected from the data base and used as the nucleic acid fragments added to the secondary contributor nucleic acid.

Step A-1, step A-2, step A-3-1, and step A-4-1 according to the "<1-1> Overview" section each correspond to step $A_2$-1, step $A_2$-2, step $A_2$-3-1, and step $A_2$-4-1, respectively, in the present implementation form. Each step is explained below.

[Step $A_2$-1]

Step $A_2$-1 is the step of preparing the data set obtained by measuring the nucleic acid mix sample added with the secondary contributor nucleic acid as described above.

In addition, the data sets prepared in step $A_2$-1 can also be the data set obtained by measuring the nucleic acid mix sample that is not added with secondary contributor nucleic acid and consists only of primary contributor nucleic acid.

This data set contains signals indicating the presence of each allele at multiple polymorphic genetic loci in the primary and secondary contributor nucleic acids. It is preferable that the polymorphic genetic loci here are loci with single nucleotide polymorphisms (SNPs) that are known to be associated with cancer. The known SNPs associated with cancer are in a data that the polymorphic genetic loci with these SNPs can be arbitrarily selected from the data base.

[Step $A_2$-2]

Step $A_2$-2 is the step of performing a linear combination on a numerical group that includes at least aforementioned (A1) and aforementioned (A2), for the polymorphic genetic loci at which the signals indicating the presence of alleles derived from the aforementioned primary and aforementioned secondary contributor nucleic acids among the aforementioned multiple polymorphic genetic loci from the data of the aforementioned data set are detected separately.

[Step $A_2$-3-1]

Step $A_2$-3-1 is the step of assigning fidelity to the composite variables produced by linear combination, and all explanations in step A-3-1 above are applicable. The authenticity of the secondary contributor component signal intensity is determined as follows.

If a nucleic acid fragment containing the sequence information of the aforementioned polymorphic genetic locus at which the aforementioned mutation was introduced is added to a nucleic acid mix sample, the secondary contributor component signal should be detected for the nucleic acid fragment.

Therefore, in such case, the secondary contributor component signal is considered true if the secondary contributor component signal is detected for the nucleic acid fragment.

On opposite, the secondary contributor component signal is considered false if the secondary contributor component signal is not detected for the nucleic acid fragment. This indicates that the result in which the secondary contributor component signal is not detected is true.

On the other hand, if a nucleic acid fragment containing the sequence information of the aforementioned polymorphic genetic locus at which the aforementioned mutation was introduced is not added to a nucleic acid mix sample, the secondary contributor component signal cannot be detected for the nucleic acid fragment.

Therefore, in such case, the secondary contributor component signal is considered false if the secondary contributor component signal is detected for the nucleic acid fragment.

On opposite, the secondary contributor component signal is considered true if the secondary contributor component signal is not detected for the nucleic acid fragment. This indicates that the result in which the secondary contributor component is not detected is true.

[Step $A_2$-4-1]

Step $A_2$-4-1 is the step of obtaining a model function, and all explanations in step A-4-1 described above are applicable.

In the present implementation as well, it is preferable to obtain the model function f2(x2) with secondary contributor component signal intensity as the predictor variable x2, and the model function f3(x3) with secondary contributor component mix rate as the predictor variable x3. For the specific method of obtaining the model functions in the present implementation, the explanations in step A-4-2 and step A-4-3 above are applicable.

In addition, in the present invention as well, the model functions created above can be multiplied by each other to create a model function of multiplication. The specific form of implementation is as described above.

Another implementation form of creating a model function from the data set obtained in cancer test will be explained. The model function created in the present implementation form is based on the data of a single polymorphic genetic locus.

Specifically, the following step $A_{2'}$-1, step $A_{2'}$-2, and aforementioned step $A_2$-3-1 and $A_2$-4-1 are included. Although according to detail below, explanations overlapping with other implementation forms described above are omitted.

[Step $A_{2'}$-1]

Step $A_{2'}$-1 is the step of preparing the data set obtained by measuring multiple nucleic acid mix samples that are each added with the aforementioned secondary contributor nucleic acids in different ratios. The difference from step $A_2$-1 is that this step prepares multiple nucleic acid mix samples in which the secondary contributor nucleic acids are each added in different ratios.

It also differs in that while step $A_2$-1 described above includes data from multiple polymorphic genetic loci, the data set for step $A_{2'}$-1 includes signals indicating the presence of each allele at a single polymorphic genetic locus in the primary and secondary contributor nucleic acids.

In other words, step $A_{2'}$-1 is unique in that it only requires the preparation of data from a single polymorphic genetic locus, while it also requires the preparation of data from multiple nucleic acid mix samples in which the secondary contributor nucleic acids are each added in different ratios.

[Step $A_{2'}$-2]

Step A2'-2 is the step of producing one or more composite variables by linearly combining a numerical group that includes at least the following (A1') and (A2'), for the single polymorphic genetic locus at which the signals indicating the presence of alleles derived from the primary and secondary contributor nucleic acids from the data of the data set are detected separately.

(A1') Secondary contributor component signal intensity indicating the presence of alleles at the aforementioned single polymorphic genetic locus derived from the aforementioned secondary contributor nucleic acids.

(A2') Secondary contributor component mix rate indicating the ratio of the aforementioned secondary contributor component signal intensity to the total signal intensity derived from alleles at the aforementioned single polymorphic genetic locus.

The essence of (A1') and (A2') is identical to that of (A1) and (A2) describe above, only being different in expression because the data to prepared in step A2'-1 is for a single polymorphic genetic locus.

Since the subsequent step $A_2$-3-1 and step $A_2$-4-1 are as described above, detailed explanation is omitted.

The implementation form that includes step $A_{2'}$-1, step $A_{2'}$-2, and the abovementioned step $A_2$-3-1 and step $A_2$-4-1, is useful for creating a model function from data obtained by microarrays, digital PCR, and nucleotide sequencing (especially next-generation sequencing), for which there is no general method for creating calibration curves.

<1-4> Transplant Organ Engraftment Monitoring

Next, the implementation form of creating a model function from the data set obtained in transplant organ engraftment monitoring will be explained. The explanations in "<1-1> Overview" section is also applicable to this implementation form. For this reason, any redundant explanation will be omitted to an appropriate degree.

In the present implementation form, the primary contributor is the recipient of the organ transplant and the secondary contributor is the organ transplanted from the donor.

In the present implementation form, the nucleic acid mix sample in the present implementation contains primary and secondary contributor nucleic acids with genetic information from the recipient of the organ transplant and the transplanted organ, respectively. The nucleic acid mix sample contains more primary contributor nucleic acid than the secondary contributor nucleic acid. Of course, the genetic information from the transplanted organ is equivalent to the genetic information from the donor.

The nucleic acid mix sample in the present implementation form can be a sample obtained from the recipient after transplantation, specifically a circulating cell-free nucleic acid.

Alternatively, the sample can be prepared by artificially mixing recipient-derived primary contributor nucleic acid obtained from the recipient, and donor-derived secondary contributor nucleic acid obtained from the donor of transplanted organ. In this case, the secondary contributor nucleic acid is preferably mixed in a ratio at which its copy number is less than 50%, more preferably 40% or less, even more preferably 30% or less, even more preferably 20% or less, and even more preferably 10% or less, of the copy number of the primary contributor nucleic acid, so that the signal derived from the primary contributor nucleic acid is detected stronger than the signal derived from the secondary contributor nucleic acid.

Step A-1, step A-2, step A-3-1, and step A-4-1 according to "<1-1> Overview" section each correspond to step $A_3$-1, step $A_3$-2, step $A_3$-3-1, and step $A_3$-4-1, respectively, in the present implementation form. Each step is explained below.

[Step $A_3$-1]

Step $A_3$-1 is the step of preparing a data set obtained by measuring the nucleic acid mix sample described above.

This data set contains signals indicating the presence of each allele at multiple polymorphic genetic loci in the primary and secondary contributor nucleic acids. It is preferable that the polymorphic genetic loci here are loci with single nucleotide polymorphisms (SNPs), which are used in Human Identification (HID). The known SNPs used in HID are in a database that the polymorphic genetic loci with these SNPs can be arbitrarily selected from the data base.

In addition, the authenticity of the signal indicating the presence of each allele must be known in prior. One method to identify the authenticity of the signal is to identify the genotypes of the recipient and the donor of the organ transplant by analyzing each of their genomic DNA. If the results contain a signal indicating the presence of an allele that both the recipient and donor do not have, the signal can be determined as false.

A signal, indicating the presence of an allele that is not present in the recipient, and homozygous or heterozygous in the donor, can be determined as true if data set of the nucleic acid mix sample that is prepared by artificially mixing recipient-derived primary contributor nucleic acid obtained from the recipient and donor-derived secondary contributor nucleic acid obtained from the donor of the transplanted organ.

The data obtained in step $A_3$-1 can include data on the nucleic acid sample that only contains the primary contributor nucleic acid. Since the nucleic acid only contains primary contributor nucleic acid derived from the recipient of the organ transplant and does not contain any secondary contributor nucleic acid derived from the donor, if a signal indicating the presence of an allele that is not present in the recipient and only present in the donor is detected, the detected signal can be determined as false.

[Step $A_3$-2]

Step $A_3$-2 is the step of performing linear combination on a numerical group that includes at least aforementioned (A1) and (A2) for the polymorphic genetic loci, at which the signals indicating the presence of alleles derived from the aforementioned primary and aforementioned secondary contributor nucleic acids among the aforementioned multiple polymorphic genetic loci from the data of the aforementioned data set are detected separately.

Specifically, if a specific allele at a specific polymorphic genetic locus is homozygous in the recipient of the organ transplant, the signals indicating the presence of alleles derived from the primary and secondary contributor nucleic acids should be detected separately. In other words, the signals indicating the presence of alleles derived from the primary and secondary contributor nucleic acids cannot be mixed.

[Step $A_3$-3-1]

Step $A_3$-3-1 the step of assigning fidelity to the composite variables produced by linear combination, and all the explanations in step A-3-1 above are applicable. The authenticity of the secondary contributor component signal intensity is determined as follows.

For an allele that is not present in the recipient, and homozygous or heterozygous in the donor, the primary and secondary contributor component signals should be detected separately.

Therefore, the secondary contributor component signal is considered true if the primary and secondary contributor component signals are detected separately for the aforementioned allele.

On opposite, the secondary contributor component signal is considered false if the primary and secondary contributor component signals are not detected separately for the aforementioned allele. This indicates that the result in which the secondary contributor component signal is not detected is false.

On the other hand, for an allele that is not present in both the recipient and the donor, the primary and secondary contributor component signals cannot be detected separately.

Therefore, the secondary contributor component signal is considered false if the primary and secondary contributor component signals are detected separately for the aforementioned allele.

On opposite, the secondary contributor component signal is considered true if the primary and secondary contributor component signals are not detected separately for the aforementioned allele. This indicates that the result in which the secondary contributor component signal is detected is true.

[Step $A_3$-4-1]

Step $A_3$-4-1 is the step of obtaining a model function, and all explanations in step A-4-1 above are applicable.

In the present implementation as well, it is preferable to obtain the model function f2(x2) with secondary contributor component signal intensity as the predictor variable x2, and the model function f3(x3) with secondary contributor component mix rate as the predictor variable x3. For the specific method of obtaining the model functions in the present implementation, the explanations in step A-4-2 and step A-4-3 above are applicable.

In addition, in the present invention as well, the model functions created above can be multiplied by each other to create a model function of multiplication. The specific form of implementation is as described above.

<2> Method for Calculating Fidelity

The present invention is about the method for calculating fidelity. The specific implementation form of the method for calculating fidelity in the present invention is explained below. The explanation on the method for calculating fidelity in the present intention that overlaps with the method for creating model functions described above is omitted to an appropriate degree.

In the present invention, fidelity is calculated by inputting predictor variable into a model function. Here, the model function is the model function obtained by the method described above, the model function in any of the following equations 1~3, or the model function of multiplication that is created by multiplying two or more model functions selected from the group of model functions of the following equations 1~3.

In the present implementation form, the numerical values that are predictor variables in each model function is input to the model functions. Specifically, more than one or two numerical values selected from the following (B1) and (B2) in the data set obtained in the following step B-1, and the composite variables obtained in the following step B-2.

The method for calculating the fidelity in the present invention includes step B-1 below. If the numerical values input to the model functions are composite variables, the composite variables are generated by step B-2 below.

The implementation form comprising step B-1, step B-2, and step B-3-1 are described below.

[Step B-1]

Step B-1 is the step of preparing a data set obtained by measuring a nucleic acid mix sample containing primary and secondary contributor nucleic acids with genetic information from the primary and secondary contributors, respectively. The nucleic acid mix sample contains more primary contributor nucleic acids than secondary contributor nucleic acids. Also, the data set contains signals indicating the presence of each allele at multiple polymorphic genetic loci in the primary contributor nucleic acids and the aforementioned secondary contributor nucleic acids.

The method of obtaining the aforementioned data set is not particularly limited. The data set can be primarily obtained using the analysis method described below, or secondarily obtained from a data set that was primarily obtained by a third person.

The data set is not particularly limited, as long as it can be obtained using analytical methods that can detect each allele at a polymorphic genetic locus separately. The analytical methods are preferably the methods that can detect signal nucleotide substitutions (SNPs) at a polymorphic genetic locus separately.

For example, the analytical methods can be next-generation sequencing, digital PCR, microarrays, multiplexing PCR, and mass spectrometry that are used for detecting SNPs. Detailed explanation on these methods is as according to "<1> Method for creating model functions" section above.

The type of nucleic acid mix sample is also not particularly limited. For example, the following types of samples are preferable: circulating cell-free nucleic acid samples (cfDNA, cfRNA) obtained from the blood of a pregnant woman obtained in prenatal genetic testing, circulating cell-free nucleic acid samples (cfDNA, cfRNA) obtained from the blood of a test subject in cancer testing, and circulating cell-free nucleic acid samples (cfDNA, cfRNA) obtained from the blood of a recipient in transplant organ engraftment monitoring.

The data set in the method for calculating fidelity includes signals indicating the presence of each allele at multiple polymorphic genetic loci, but these "multiple polymorphic genetic loci" do not need to be the same as the "multiple polymorphic genetic loci" that were used for creating the model function, and the degree the overlap is also not particularly limited.

The overlap with the "multiple polymorphic genetic loci" that were used for creating the model function is preferably 80% or less, more preferably 70% or less, even more preferably 60% or less, and even more preferably 50% or less.

Also, the overlap with the "multiple polymorphic genetic loci" that were used for creating the model function can be 0%, more preferably 10% or above, even more preferably 20% or above, even more preferably 30% or above, and even more preferably 40% or above.

[Step B-2]

Step B-2 is the step of producing one or more composite variables by linearly combining a numerical group that includes at least the following (B1) and (B2), for the polymorphic genetic loci at which the signals indicating the presence of alleles derived from the primary and secondary contributor nucleic acids among the multiple polymorphic genetic loci from the data of the aforementioned data set are detected separately.

(B1) is secondary contributor component signal intensity. Secondary contributor component signal intensity is the intensity of the signal indicating the presence of alleles at specific polymorphic genetic loci derived from the secondary contributor nucleic acid. For its definition and specific form, the explanation about (A1) above is applicable.

(B2) is secondary contributor component mix rate. Secondary contributor component mix rate is the ratio of the secondary contributor component signal intensity to the total signal intensity derived from alleles at specific polymorphic genetic loci. Therefore, it can be expressed by the formular "Secondary contributor component mix rate=Secondary contributor signal intensity/Total signal intensity". For its definition and specific form, the explanation about (A2) above is applicable.

The numerical group subject to linear combination in step B-2 can include numerical values other than (B1) and (B2) described above. In other words, linear combination is performed on a numerical group that includes (B1) and (B2) for specific polymorphic genetic loci, as well as various measurements and calculated values for the specific polymorphic genetic loci.

The following is an explanation on the numerical values (B3)~(B5) that can be included in the numerical group subject to linear combination. Only one type of numerical values selected from (B3)~(B5) listed below can be included in the aforementioned numerical group, or two or more numerical values arbitrarily selected can be included in the aforementioned numerical group. Also, all of (B3)~(B5) can be included in the aforementioned numerical group.

(B3) is primary contributor component signal intensity. Primary contributor component signal intensity is the intensity of the signal indicating the presence of one allele at specific polymorphic genetic loci derived from the primary contributor nucleic acid. For its definition and specific form, the explanation about ($A_3$) above is applicable.

(B4) is primary contributor component mix rate. Primary contributor component mix rate is the ratio of the primary contributor component signal intensity to the total signal intensity derived from alleles at specific polymorphic genetic loci. Therefore, it can be expressed by the formular "Primary contributor component mix rate=Primary contributor component signal intensity/Total signal intensity". For its definition and specific form, the explanation about (A1) above is applicable.

(B5) is noise. For its definition and specific form, the explanation about (A1) above is applicable.

As described above, the data set obtained in step B-1 is a set of data on multiple polymorphic genetic loci. Therefore, the data set prepared in step B-1 contains multiple sets of data, each set with (B1) and (B2) above, and other numerical data for specific polymorphic genetic loci.

In addition, it is preferable that the numerical data included in the numerical group that is the subject of linearly combination is standardized. As already known, "standardization" is the step of transforming multiple sets of data so that the mean is 0 and the variance is 1, and it is sometimes referred to as "normalization" as well. Standardized data can be obtained by the following equation.

Standardized data=[(Original data)−(Mean value)]/(Sample standard deviation)

"Polymorphic genetic loci at which the signals indicating the presence of alleles derived from the primary and secondary contributor nucleic acids are detected separately" refers to polymorphic genetic loci at which the signal indicating the presence of alleles derived from the primary contributor nucleic acid and the signal indicating the presence of alleles derived from the secondary contributor nucleic acid are not mixed.

For example, in the case of prenatal genetic testing, if the mother is heterozygous for allele A and allele B at specific polymorphic genetic loci, the analysis of cfDNA always detects the signals of allele A and allele B that are derived from the mother's genomic DNA, regardless of the father's genotype. Either of the signals of allele A and allele B is mixed with the signal derived from the fetal cffDNA, but it cannot be distinguished from the signal derived from the mother's genomic DNA. Such data is excluded from the analysis of the present invention.

In addition, in the case of cancer testing, if the test subject is homozygous or heterozygous for a congenital cancer-associated mutation, the mutation is always in the ctDNA. Therefore, the signal derived from the test subject is mixed with the signal derived from cancer cells. Such data is excluded from the analysis of the present invention.

In the case of the transplant organ engraftment monitoring, if the recipient is heterozygous for allele A and allele B at specific polymorphic genetic loci, the analysis of cfDNA always detects the signals of allele A and allele B derived from the recipient's genomic DNA, regardless of the donor's genotype. Either of the signals of allele A and allele B is mixed with the signal derived from donor cffDNA, but it cannot be distinguished from the signal derived from the recipient's genomic DNA. Such data is excluded from the analysis of the present invention.

Therefore, in step B-2, the polymorphic genetic loci to be analyzed are limited to "polymorphic genetic loci at which the signals indicating the presence of alleles derived from the primary and secondary contributor nucleic acids are detected separately". In other words, the polymorphic genetic loci analyzed in step B-2 should be polymorphic genetic loci at which the signal indicating the presence of alleles derived from the secondary contributor nucleic acid cannot be mixed with the signal indicating the presence of alleles derived from the primary contributor nucleic acid.

In step B-2, one or more composite variables are produced by linearly combining the numerical group described above. Principal component analysis is a good example of a linear combination method. In addition, the composite variables can be produced by other methods. Even if the composite variables are produced by other method, it is preferable that they are composite variables that can be produced by principal component analysis.

The number of composite variables that can be produced increases as the number of types of numerical values included in the numerical group to be linearly combined increases. The number of composite variables produced in step B-2 is not particularly limited.

Step B-3-1~B-3-4 below are the steps of calculating fidelity by inputting the numerical values obtained by the method as above into a model function.

[Step B-3-1]

Step B-3-1 is the step of calculating fidelity by inputting the composite variables produced from linear combination in step B-2 into the model function, which has the composite variables as the predictor variable and the fidelity as the objective variable. It is preferrable to have the type and the number of numerical values in the numerical group used for the linear combination to create the model function to be equivalent to that used as the input value to the model function.

The present invention is also about the method for calculating fidelity, which comprises step B-1 described above and the following step B-3-2.

[Step B-3-2]

Step B-3-2 is the step of calculating fidelity by inputting the aforementioned (B1) secondary contributor component signal intensity into the model function f2(x2) described above. The fidelity of the data can be easily calculated by inputting the secondary contributor component signal intensity primarily included in the data set into the model function f2(x2).

The present invention is also about the method for calculating fidelity, which comprises step B-1 described above and the following step B-3-3.

[Step B-3-3]

Step B-3-3 is the step of calculating fidelity by inputting the aforementioned (B2) secondary contributor component mix rate into the model function f3(x3) described above. The fidelity of the data can be easily calculated by inputting the secondary contributor component mix rate into the model function f3(x3).

The present invention also about the method for calculating fidelity, which comprises step B-1 described above and the following step B-3'.

[Step B-3']

Step B-3' is the step of calculating fidelity by inputting variables selected from the following three types of numerical values into a model function of multiplication, which has the selected variables as the predictor variable and fidelity as the objective variable.

(i) The composite variables produced in step B-2 above.

(ii) The secondary contributor component signal intensity indicating the presence of the alleles at specific polymorphic genetic loci derived from the aforementioned secondary contributor nucleic acid, for the polymorphic genetic loci at which the signals indicating the alleles derived from the aforementioned primary and aforementioned secondary contributor nucleic acids among the aforementioned multiple polymorphic genetic loci are detected separately.

(iii) The secondary contributor component mix rate, which is the ratio of the aforementioned secondary contributor component signal intensity to the total signal intensity for the alleles at specific polymorphic genetic loci derived from the aforementioned secondary contributor nucleic acid, for polymorphic genetic loci at which the signals indicating the alleles derived from the aforementioned primary and aforementioned secondary contributor nucleic acids among the aforementioned multiple polymorphic genetic loci are detected separately.

The model function of multiplication described here is the model function expressed by multiplying two or more model functions selected from the following three model functions by each other, as described above.

The model function created by step A-1, step A-2, step A-3-1 and step A-4-1

The model function created by step A-1, step A-3-2 and step A-4-2

The model function created by step A-1, step A-3-3 and step A-4-3

In the preferable implementation form of the present invention, fidelity is calculator by inputting the variables corresponding to each of the predictor variables of f1(x1), f2(x2), and f3(x3) above to the model function Equation 4.

A more detailed implementation form of the method for calculating fidelity in the present invention is explained below. Specifically, non-invasive prenatal genetic test analysis, cancer testing, transplant organ engraftment monitoring, and non-invasive prenatal testing to assess disease risk are described respectively.

<2-1> Method for Calculating Fidelity for Non-Invasive Prenatal Paternity Test

Fist, the method for calculating fidelity for non-invasive prenatal paternity test will be explained. Since the explanations in <2> above are also applicable in this section, any redundant explanations are omitted to an appropriate degree.

In the present implementation, the primary contributor is the mother, the secondary contributor is the fetus in the womb of the mother, and the nucleic acid mix sample is circulating cell-free nucleic acid sample collected from the mother.

In addition, aforementioned step B-1, step B-2, and step B-3-1 each correspond to the following step $B_1$-1, step $B_1$-2, and step $B_1$-3-1, respectively.

[Step $B_1$-1]

Step $B_1$-1 is the step of preparing a data set obtained by measuring a circulating cell-free nucleic acid containing primary and secondary contributor nucleic acids with genetic information from the mother and the fetus, respectively. The data set contains signals indicating the presence of each allele at multiple polymorphic genetic loci in the primary and secondary contributor nucleic acids.

It is preferable that the aforementioned multiple polymorphic genetic loci here are the polymorphic genetic loci used in Human Identification (HID).

[Step $B_1$-2]

Step $B_1$-2 is the step of producing one or more composite variables by linearly combining a numerical group that includes at least aforementioned (B1) and aforementioned (B2), for the polymorphic genetic loci that are homozygous in the mother, and wherein the signals indicating the presence of alleles derived from the primary and secondary contributor nucleic acids among multiple polymorphic genetic loci from the data in the data set are detected separately. In addition, the genotype of the aforementioned polymorphic genetic loci in the alleged-father can be homozygous or heterozygous.

[Step $B_1$-3-1]

Step $B_1$-3-1 is the step of calculating fidelity by inputting the composite variables produced in step $B_1$-2 into the model function, which has the composite variables as the predictor variable.

<2-2> Method for Calculating Fidelity for Cancer Testing

Next, the method for calculating fidelity for cancer testing will be explained. Since explanations in <2> above are also applicable in this section, any redundant explanations are omitted to an appropriate degree.

In the present implementation, the primary contributor is the cancer test subject, the secondary contributor is cancer cells, and the nucleic acid mix sample is circulating cell-free nucleic acid samples collected from the test subject.

In addition, step B-1, step B-2, and step B-3-1 above each correspond to the following step $B_2$-1, step $B_2$-2, step and $B_2$-3-1, respectively.

[Step $B_2$-1]

Step $B_2$-1 is the step of preparing a data set obtained by measuring a circulating cell-free nucleic acid sample containing primary contributor nucleic acids with genetic information from the test subject and secondary contributor nucleic acids that may contain genetic information from the cancer cells, and also a data set that contains signals indicating the presence of each allele at multiple polymorphic genetic loci associated with cancer in the aforementioned primary and aforementioned secondary contributor nucleic acids.

Here, "may contain secondary contributor nucleic acid" refers to a situation in which the possibility the circulating cell-free nucleic acid sample may contain secondary contributor nucleic acids cannot be completely rejected.

[Step $B_2$-2]

Step $B_2$-2 is the step of producing one or more composite variables by linearly combining a numerical group that includes at least aforementioned (B1) and aforementioned (B2) for the polymorphic genetic loci wherein the signals indicating the presence of normal type allele and a mutant type allele among the multiple polymorphic genetic loci from the data in the data set are detected separately.

Normal allele is the allele found in a test subject with a healthy body who does not have cancer, and mutant allele is the allele with mutations that are known to be associated with cancer.

In step $B_2$-2, it is preferable to exclude data related to polymorphic genetic loci with a mutant allele homozygous or heterozygous in the test subject, among the aforementioned multiple polymorphic genetic loci from the data in the aforementioned data set. By excluding data related to the polymorphic genetic loci with congenital mutant alleles in the test subject, data in which the secondary contributor component signal is detected mixed with the primary contributor component signal derived from the test subject is excluded. This improves the accuracy of the calculated fidelity.

[Step $B_2$-3-1]

Step $B_2$-3-1 is the step of calculating fidelity by inputting the composite variables produced in step $B_2$-2 into the model function, which has the composite variables as the predictor variable.

<2-3> Method for Calculating Fidelity for Transplant Organ Engraftment Monitoring The method for calculating fidelity for transplant organ engraftment monitoring will be explained below. Since explanations in <2> above are also applicable in this section, any redundant explanations are omitted to an appropriate degree.

In the present implementation, the primary contributor is the recipient of the organ transplant, the secondary contributor is the transplanted organ, and the nucleic acid mix sample is circulating cell-free nucleic acid sample collected from the recipient.

In addition, aforementioned B-1, step B-2, and step B-3-1 each correspond to the following step $B_3$-1, step $B_3$-2, and step $B_3$-3-1, respectively.

[Step $B_3$-1]

Step $B_3$-1 is the step of preparing a data set obtained by measuring a circulating cell-free nucleic acid sample containing primary contributor nucleic acids with genetic information from the recipient, and secondary contributor nucleic acids that may contain genetic information from the transplanted organ. The data set contains signals indicating the presence of each allele at multiple polymorphic genetic loci in the primary and secondary contributor nucleic acids. It is preferable that the aforementioned multiple polymorphic genetic loci here are the polymorphic genetic loci used in Human Identification (HID).

[Step $B_3$-2]

Step $B_3$-2 is the step of producing one or more composite variables by linearly combining a numerical group that includes at least aforementioned (B1) and aforementioned (B2), for the polymorphic genetic loci, wherein the signals indicating the presence of alleles derived from the aforementioned primary and aforementioned secondary contributor nucleic acids among the aforementioned multiple polymorphic genetic loci from the data in the data set are detected separately.

[Step $B_3$-3-1]

Step $B_3$-3-1 is the step of calculating fidelity by inputting the composite variables produced in step $B_3$-2 into the model function, which has the composite variables as the predictor variable.

<2-4> Method for Calculating Fidelity for Non-Invasive Prenatal Testing to Assess Disease Risk The method for calculating fidelity for non-invasive prenatal testing to assess disease risk will be explained below. Since explanations in <2> above are also applicable in this section, any redundant explanations are omitted to an appropriate degree.

In the present implementation, the primary contributor is the mother, the secondary contributor is the fetus in the womb of the mother, and the nucleic acid mix sample is circulating cell-free nucleic acid sample collected from the mother.

In addition, aforementioned step B-1, step B-2, and step B-3-1 each correspond to the following step $B_4$-1, step $B_4$-2, and step $B_4$-3-1, respectively.

[Step $B_4$-1]

Step $B_4$-1 is the step of preparing a data set obtained by measuring a circulating cell-free nucleic acid obtained from the mother, which contains primary and secondary contributor nucleic acids with genetic information form the mother and the fetus in the womb of the mother, respectively. The data set contains signals indicating the presence of each allele at multiple polymorphic genetic loci associated with disease, in the primary and secondary contributor nucleic acids.

[Step $B_4$-2]

In step $B_4$-2, the data related to the polymorphic genetic loci with mutant alleles heterozygous in the mother among the aforementioned multiple polymorphic genetic loci mentioned, is first excluded from the data in the data set.

Then, one or more composite variables are produced by linearly combining a numerical group that includes at least aforementioned (B1) and aforementioned (B2) for the polymorphic genetic loci, wherein the signals indicating the presence of alleles derived from the aforementioned primary and aforementioned secondary contributor nucleic acids among the aforementioned multiple polymorphic genetic loci from the data in the data set remaining after the exclusion described above.

[Step $B_4$-3-1]

Step $B_4$-3-1 is the step of calculating fidelity by inputting the aforementioned composite variables produced in aforementioned step B-2 into a model function, which has the composite variables as the predictor variable.

<3> Method to Set Exclusion Condition

According to the method for calculating the fidelity described above, fidelity of the signals indicating the presence of a specific alle at specific polymorphic genetic loci in secondary contributor nucleic acids in the data set can be evaluated.

However, the method for calculating the fidelity described above may result in cases where the fidelity of the signal indicating the presence of the allele is calculated to be low, even when the specific allele derived from the secondary contributor nucleic acid is included in the nucleic acid mix sample. On the contrary, in some cases, the fidelity of the signal indicating the presence of the allele is calculated to be high, even when the specific allele derived from the secondary contributor nucleic acid is not included in the nucleic acid mix sample. Such aberrant results are caused due to inclusion of outliers in the data set to be analyzed. If these aberrant results can be excluded, fidelity can be calculated with higher accuracy.

The method of setting exclusion conditions in the present invention determines which data set should be excluded in order to narrow down the data of predictor variables to be input to a model function. This method of setting exclusion conditions particularly relates to prenatal genetic testing.

Specifically, it is preferable to set exclusion conditions which exclude locus if it mutually nonidentical and the parents are homozygous with the fidelity of the secondary contributor component signal intensity is preferably less than 0.8, more preferably less than 0.9, even more preferably less than 0.99, and even more preferably less than 0.999.

In addition, it is preferable to set exclusion conditions which exclude locus if it mutually identical and the parents are homozygous with the fidelity of the secondary contributor component signal is preferably 0.2 or above, more preferably 0.1 or above, even more preferably 0.01 or above, and even more preferably 0.001 or above, is excluded.

The implementation form of the method for setting exclusion conditions is explained below.

<3-1> Method for Setting Exclusion Condition (Implementation 1)

One implementation form of the method for setting exclusion conditions in the present invention comprises the following step C-1-1, step C-2-1, step C-3-1, and step C-4-1. The exclusion conditions set from this implementation form can be applied to the method for calculating fidelity for transplant organ engraftment monitoring described above.

[Step C-1-1]

Step C-1-1 is the step of preparing a data set obtained by measuring a nucleic acid mix sample containing primary and secondary contributor nucleic acids with genetic information from the primary and secondary contributors, respectively. The data set includes signals indicating the presence of each allele at multiple polymorphic genetic loci in the aforementioned primary and aforementioned secondary contributor nucleic acids. In addition, the authenticity of the aforementioned signals is known in prior.

The aforementioned polymorphic genetic loci is preferably the single nucleotide polymorphic genetic loci used in Human Identification (HID).

The primary contributor, the secondary contributor, and the nucleic acid mix sample corresponds to any of the following.

(i) The aforementioned primary contributor is the mother, the aforementioned secondary contributor is the fetus in the womb of the aforementioned mother, and the aforementioned nucleic acid mix sample is a circulating cell-free nucleic acid sample obtained from the aforementioned mother.

(ii) The aforementioned primary contributor is the recipient, the aforementioned secondary contributor is the transplanted organ, and the aforementioned nucleic acid mix sample is a circulating cell-free nucleic acid sample collected from the aforementioned recipient.

[Step C-2-1]

Step C-2-1 is the step of producing the composite variable with the highest contribution rate among the composite variables obtained by linearly combining a numerical group that contains the numerical values for the polymorphic genetic loci that meet specific condition, among the data set prepared in step C-1-1. The composite variable with the highest contribution rate is the first principal component in the case of principal component analysis.

In step C-2-1, linear combination is performed on a numerical group that contains at least the following (C1), (C2), and (C3) for the polymorphic genetic loci with an allele that is homozygous in the mother and homozygous in the father, and nonidentical genotype in the mother and the father, or homozygous in the recipient and homozygous in the donor of the transplanted organ, and nonidentical genotype in the recipient and the donor.

(C1) is secondary contributor component signal intensity. Secondary contributor component signal intensity is the intensity of the signal indicating the presence of alleles at specific polymorphic genetic loci derived from the secondary contributor nucleic acids. For its definition and specific implementation form, the explanation about (A1) above is applicable.

(C2) is secondary contributor component mix rate. Secondary contributor component mix rate is the ratio of the secondary contributor component signal intensity to the total signal intensity derived from alleles at specific polymorphic genetic loci. In other words, it can be expressed by the equation: "Secondary contributor component mix rate=Secondary contributor component signal intensity/Total signal intensity". For its definition and specific implementation form, the explanation about (A2) above is applicable.

(C3) is noise. Noise is a numerical value obtained by subtracting the primary and secondary contributor component signal intensities from the sum of the signal intensities derived from alleles at specific polymorphic loci. For its definition and specific implementation form, the explanation about (A5) above is applicable.

The numerical group subject to linear combination in step C-2-1 may include numerical values other than (C1), (C2), and (C3) described above. In other words, linear combination is performed on a numerical group that includes (C1), (C2), and (C3) for specific polymorphic genetic loci, as well as various measurements and calculated values for the specific polymorphic genetic loci.

The following is an explanation on the numerical values (C4)~(C5) that can be included in the numerical group subject to linear combination. Only one type of numerical values selected from (C4)~(C5) listed below can be included in the aforementioned numerical group, or two or more numerical values arbitrarily selected can be included in the aforementioned numerical group. Also, all of (C4)~(C5) can be included in the aforementioned numerical group.

(C4) is primary contributor component signal intensity. Primary contributor component signal intensity is the intensity of the signal indicating the presence of one allele at specific polymorphic genetic loci derived from the primary contributor nucleic acid. For its definition and specific form, the explanation about (A3) above is applicable.

(C5) is primary contributor component mix rate. Primary contributor component mix rate is the ratio of the primary contributor component signal intensity to the total signal intensity derived from alleles at specific polymorphic genetic loci. Therefore, it can be expressed by the equation "Primary contributor component mix rate=Primary contributor component signal intensity/Total signal intensity". For its definition and specific form, the explanation about (A1) above is applicable.

The data set here is a set of data for multiple polymorphic genetic loci. Therefore, the data set contains multiple sets of data, with the numerical data of (C1-1)~(C5-1) above for the specific polymorphic genetic loci as one set.

It is preferable the numerical data in the numerical group that is the subject of linear combination is standardized.

Furthermore, it is preferable the type and the number of values in the group of numerical values used for the linear combination, and the type and number of values in the group of numerical used for the linear combination to generate the composite variable in step C-2-1, are equivalent.

[Step C-3-1]

Step C-3-1 is a step of setting a threshold value for the composite variable so as to exclude some or all of the outliers of the aforementioned composite variable obtained by the linear combination in step C-2-1. Its specific mode is not particularly limited.

The aforementioned outliers are abnormal values calculated when fidelity is produced using the model function created by the method in the present invention.

For example, when a specific allele derived from the secondary contributor nucleic acid is included in the nucleic acid mix sample, but the fidelity of the signal indicating the presence of the allele is preferably less than 0.6, more preferably less than 0.7, and even more preferably less than 0.8, the numerical value for the allele can be considered as an outlier.

Or, when a specific allele derived from the secondary contributor nucleic acid is not included in the nucleic acid mix sample, but the fidelity of the signal indicating the presence of the allele is preferably 0.4 or above, more preferably 0.3 or above, and even more preferably 0.2 or above, the numerical value for the allele can be considered as an outlier.

Numerical values that are more than two times as far from the mean of the composite variable as its standard deviation, more preferably at least three times, even more preferably at least four times, and even more preferably at least five times of the standard deviation, can be considered as outliers.

The following method can be a specific form of step C-3-1.

First, a tentative threshold value for the aforementioned composite variable is set, and the following tentative exclusion condition C1 is set.

(Tentative Exclusion Condition C1)

From the data set obtained by analyzing a nucleic acid mix sample that contains primary contributor nucleic acid with genetic information from the mother or the recipient, and secondary contributor nucleic acid with genetic information from the fetus or the transplanted organ the composite variable with the highest contribution rate that is obtained by linearly combining a numerical group that includes at least aforementioned (C1), aforementioned (C2), and aforementioned (C3), for the polymorphic genetic loci with alleles that are homozygous in the mother and homozygous in the alleged-father, and the genotype is nonidentical in the aforementioned mother and the aforementioned alleged-father, or alleles that are homozygous in the aforementioned recipient and homozygous in the aforementioned donor of the transplanted organ, and the genotype is nonidentical in the aforementioned recipient and the aforementioned donor, corresponding to less than the tentative threshold are removed.

Then, this tentative exclusion condition C1 is applied to the data set to be analyzed, and then the method for calculating fidelity described above is applied to the remaining data set that is not excluded to calculate the fidelity. Whether aberrant results are excluded from the result of fidelity calculated here is excluded or not, is tested. If aberrant results are not excluded, or if results with fidelity that accurately reflect the facts are over-excluded, the tentative exclusion conditions are re-set and the test equivalent to the processes described above is repeated to identify the optimal conditions.

Step C-3-1 can be a form that comprises step C-3-1-1 and step C-3-1-2 described below.

[Step C-3-1-1]

Step C-3-1-1 is the step of calculating fidelity by inputting the required numerical values into the model function created by the method of the present invention described above, which has either of the composite variables, (C1) secondary contributor component signal intensity, (C2) secondary contributor component mix rate, and (C3) noise that are produced by the linear combination in step C-2-1, as predictor variables.

The model function used to calculate fidelity is not particularly limited as long as it is the model function according to "<1> Method of creating model functions" section. It is preferable that fidelity is calculated by inputting predictor variables into the model function represented by any of the equations 1~4 described.

[Step C-3-1-2]

Next, in step C-3-1-2, a scatter plot is created by plotting the composite variables produced by the linear combination in step C-2-1 and the fidelity calculated in step C-3-1-1. For example, in a scatter plot where the composite variables are plotted on the vertical axis and the fidelity is plotted on the horizontal axis, a set of data points that are distributed in the horizontal (the direction in which the fidelity spread) direction (in other words, the variance of the value of the composite variables are small and the variance of the value of the fidelity is large), and a set of data points that are distributed in the vertical (the direction in which the composite variables spread) direction (in other words, the variance of the value of the composite variables are large and the variance of the fidelity is small) are observed.

Of these, the set of data points that is spread in the direction the fidelity is distributed (the data set extending horizontally) is identified as the exclusion candidate.

On the other hand, the set of data points that is spread in the direction the composite variables are distributed (the data set extending vertically) is identified as the non-exclusion candidate.

Then, a threshold is set for the value of the aforementioned composite variables to exclude some or all of the exclusion candidates.

A threshold value is set for the composite variables, so that the ratio of that data points to be excluded is preferably 50% or above, more preferably 60% or above, even more preferably 70% or above, even more preferably 80% or above, even more preferably 90% or above, even more preferably 95% or above of all data points of the exclusion candidate (that overlapping with non-exclusion candidates is also included in the exclusion candidate).

[Step C-4-1]

Step C-4-1 is the step of setting the following exclusion condition C1 as the condition that should be excluded from the data set to be input to the model function for calculating fidelity.

(Exclusion Condition C1)

From the data set obtained by analyzing a nucleic acid mix sample that contains primary contributor nucleic acid with genetic information from the mother or the recipient, and secondary contributor nucleic acid with genetic information from the fetus or the transplanted organ,

- the composite variable with the highest contribution rate that is obtained by linearly combining a numerical group that includes at least aforementioned (C1), aforementioned (C2), and aforementioned (C3), for the polymorphic genetic loci with alleles that are homozygous in the mother and homozygous in the alleged-father, and the genotype is nonidentical in the aforementioned mother and the aforementioned alleged-father, or
- alleles that are homozygous in the aforementioned recipient and homozygous in the aforementioned donor of the transplanted organ, and the genotype is nonidentical in the aforementioned recipient and the aforementioned donor, corresponding to less than the aforementioned threshold set in aforementioned step C-3-1 are removed.

By applying the method for calculating fidelity described above to the data set remaining after the exclusion, highly accurate fidelity calculation results with aberrant results removed can be obtained.

<3-2> Method to Set Exclusion Condition (Implementation 2)

One implementation of the method for setting exclusion conditions in the present invention comprises the following step C-1-2, step C-2-2, step C-3-2, and step C-4-2.

[Step C-1-2]

Step C-1-2 is the step of preparing a data set obtained by measuring a nucleic acid mix sample containing primary and secondary contributor nucleic acids with genetic information from the primary and secondary contributors, respectively. The data set includes signals indicating the presence of each allele at multiple polymorphic genetic loci in the aforementioned primary and aforementioned secondary contributor nucleic acids. In addition, the authenticity of the aforementioned signals is known in prior.

The aforementioned polymorphic genetic loci is preferably the single nucleotide polymorphic genetic loci used in Human Identification (HID).

The primary contributor, the secondary contributor, and the nucleic acid mix sample corresponds to any of the following.

(i) The aforementioned primary contributor is the mother, the aforementioned secondary contributor is the fetus in the womb of the aforementioned mother, and the aforementioned nucleic acid mix sample is a circulating cell-free nucleic acid sample obtained from the aforementioned mother.

(ii) The aforementioned primary contributor is the recipient, the aforementioned secondary contributor is the transplanted organ, and the aforementioned nucleic acid mix sample is a circulating cell-free nucleic acid sample collected from the aforementioned recipient.

[Step C-2-2]

Step C-2-2 is the step of producing the composite variable with the highest or the second highest contribution rate among the composite variables obtained by linearly combining a numerical group that contains the numerical values for the polymorphic genetic loci that meet specific condition among the data set prepared in step C-1-2. The composite variable with the highest contribution rate is the first principal component in the case of principal component analysis. The composite variable with the second highest contribution rate is the second principal component in the case of principal component analysis.

In step C-2-2, linear combination is performed on a numerical group that includes at least (C1), (C2), and (C3) described above for the polymorphic genetic loci, which has an allele that is homozygous in the mother and homozygous in the father, and identical genotype in the mother and the aforementioned father, or homozygous in the recipient and homozygous in the donor of the transplanted organ, and identical genotype in the recipient and the donor. The numerical group subject to linear combination can include numerical values other than (C1), (C2), and (C3). For example, (C4)~(C5) described above can be included. For other specific form of step C-2-2, the explanation on step C-2-1 described above is applicable.

Furthermore, it is preferable is the type and the number of numerical values in the group of numerical values used for the linear combination to create the model function, and the type and the number of numerical values in the group of numerical values used for the linear combination to produce the composite variable in step C-2-2, are equivalent.

[Step C-3-2]

Step C-3-2 is the step of setting a threshold on the value of the aforementioned composite variables, to exclude some of all of the outliers of the composite variables obtained by the linear combination in step C-2-2. Its detailed form is not particularly limited. For the definition of the outliers, the explanation on step C-3-1 described above is applicable.

The following method can be a specific form of step C-3-2.

First, a tentative threshold value for the aforementioned composite variable is set, and the following tentative exclusion condition C2 is set.

(Tentative Exclusion Condition C2)

From the data set obtained by analyzing a nucleic acid mix sample that contains primary contributor nucleic acid with genetic information from the mother or the recipient, and secondary contributor nucleic acid with genetic information from the fetus or the transplanted organ, the composite variable with the highest or the second highest contribution rate that is obtained by linearly combining a numerical group that includes at least aforementioned (C1), aforementioned (C2) and aforementioned (C3), for the polymorphic genetic loci with alleles that are homozygous in the mother and homozygous in the alleged-father, and the genotype is identical in the aforementioned mother and the aforementioned alleged-father, or alleles that are homozygous in the aforementioned recipient and homozygous in the aforementioned donor of the transplanted organ, and the genotype is identical in the aforementioned recipient and the aforementioned donor, corresponding to less than the tentative threshold set are removed.

Then, this tentative exclusion condition C2 is applied to the data set to be analyzed, and then the method for calculating fidelity described above is applied to the remaining data set that is not excluded to calculate the fidelity. Whether aberrant results are excluded from the result of fidelity calculated here is excluded or not, is tested. If aberrant results are not excluded, or if results with fidelity that accurately reflect the facts are over-excluded, the tentative exclusion conditions are re-set and the test equivalent to the processes described above is repeated to identify the optimal conditions.

Step C-3-2 can be a form that comprises step C-3-2-1 and step C-3-2-2 described below.

[Step C-3-2-1]

Step C-3-2-1 is the step of calculating fidelity by inputting the required numerical values into the model function created by the method of the present invention described above, which has either of the composite variables, (C1) secondary contributor component signal intensity, (C2) secondary contributor component mix rate, and (C3) noise that are produced by the linear combination in step C-2-2, as predictor variables.

The model function used to calculate fidelity is not particularly limited as long as it is the model function according to "<1> Method of creating model functions" section. It is preferable that fidelity is calculated by inputting predictor variables into the model function represented by any of the equations 1~4 described.

[Step C-3-2-2]

Next, in step C-3-2-2, a scatter plot is created by plotting the composite variables produced by the linear combination in step C-2-2 and the fidelity calculated in step C-3-2-1. For example, in a scatter plot where the composite variables are plotted on the vertical axis and the fidelity is plotted on the horizontal axis, a set of data points that are distributed in the horizontal (the direction in which the fidelity spread) direction (in other words, the variance of the value of the composite variables are small and the variance of the value of the fidelity is large), and a set of data points that are distributed in the vertical (the direction in which the composite variables spread) direction (in other words, the variance of the value of the composite variables are large and the variance of the fidelity is small) are observed.

Of these, the set of data points that is spread in the direction the fidelity is distributed (the data set extending horizontally) is identified as the exclusion candidate.

On the other hand, the set of data points that is spread in the direction the composite variables are distributed (the data set extending vertically) is identified as the non-exclusion candidate.

Then, a threshold is set for the value of the aforementioned composite variables to exclude some or all of the exclusion candidates.

A threshold value is set for the composite variables, so that the ratio of that data points to be excluded is preferably 50% or above, more preferably 60% or above, even more preferably 70% or above, even more preferably 80% or above, even more preferably 90% or above, even more preferably 95% or above of all data points of the exclusion candidate (that overlapping with non-exclusion candidates is also included in the exclusion candidate).

[Step C-4-2]

Step C-4-2 is the step of setting the following exclusion condition C2 as the condition that should be excluded from the data set to be input to the model function for calculating fidelity.

(Exclusion Condition C2)

From the data set obtained by analyzing a nucleic acid mix sample that contains primary contributor nucleic acid with genetic information from the mother or the recipient, and secondary contributor nucleic acid with genetic information from the fetus or the transplanted organ, the composite variable with the highest or the second highest contribution rate that is obtained by linearly combining a numerical group that includes at least aforementioned (C1), aforementioned (C2) and aforementioned (C3), for the polymorphic genetic loci with alleles that are homozygous in the mother and homozygous in the alleged-father, and the genotype is identical in the aforementioned mother and the aforementioned alleged-father, or alleles that are homozygous in the aforementioned recipient and homozygous in the aforementioned donor of the transplanted organ, and the genotype is identical in the aforementioned recipient and the aforementioned donor, corresponding to less than the aforementioned threshold set in aforementioned step C-3-2 are removed.

By applying the method for calculating fidelity described above to the data set remaining after the exclusion, highly accurate fidelity calculation results with aberrant results removed can be obtained.

<4> Method for Calculating Fidelity by Applying Exclusion Condition

The present invention is about the method for calculating fidelity by applying exclusion condition C1 and/or exclusion condition C2 set by the method for setting exclusion conditions described above, to the data set prepared in step B2-1 of the "<2-3> Method of calculating fidelity for monitoring of transplant organ engraftment" above, and applying the method for calculating fidelity in the present invention for the remaining data sets that are not excluded.

The exclusion conditions to be applied can be either or both of exclusion condition C1 and exclusion condition C2. If the types of numerical values included in the numerical group linearly combined in step $B_1$-2 or step $B_3$-2 are 10 types or above, more preferably 20 types or above, and even more preferably 30 types or above, fidelity can be calculated with high accuracy by simply applying exclusion condition C1 only.

Other than applying exclusion condition C1 and/or exclusion condition C2, the explanation in "<2-3> Method for calculating fidelity for transplant organ engraftment monitoring" described above can be applied to the implementation form of the present invention.

Since the exclusion conditions are applied to the data set, outliers are excluded from the input values. This greatly reduces the problems with aberrant results being output as the fidelity calculated by the model function.

<5> Program

The present invention is also about the program for executing a computer to perform more than one or two methods selected from the method to create model functions, the method to calculate fidelity, and the method to set exclusion conditions described above. A processor in a computer can be configured to operate according to the program of the invention stored in an internal storage device, such as a hard disk drive, to perform more than one or two methods selected from the method to calculate model functions, the method to calculate fidelity, and the method to set exclusion conditions described above.

<6> Memory Unit

The present invention also relates to the memory unit in which the program described above is recorded. The present invention also relates to the memory unit in which model functions created by the methods described above is recorded. The memory unit is not limited and it may include semiconductor memory, hard disk magnetic memory unit, optical storage medium, and other memory unit that can be read by a computer.

<7> Fidelity Calculation System

The present invention also relates to the system for calculating fidelity that comprises a storage unit in which the model functions described above, and a processing unit that executes the method for calculating fidelity described above. A preferable implementation of the fidelity calculation system in the present invention is described below.

The processing unit is a unit for processing the data set that is obtained by the analyzer and to be evaluated. The processing unit may be, for example, an arithmetic device (which may be referred to as calculator) that implements the data processing necessary for the calculation of fidelity, by reading and executing a program (which executes the method described above for calculating fidelity) stored in a storage unit. The processing unit consists of attributes of a data processing unit. For example, it may be CPU (Central Processing Unit), MPU (Micro Processing Unit), DSP (Digital Signal Processor), and FPGA (Field Programmable Gate Array), etc. The processing unit may be a multi-core processor containing two or more cores.

The memory unit is a circuit configured to store data and programs for various data processing executed by the processing unit. The memory unit consists of both or at least one of a non-volatile memory and a volatile memory. For example, it may be RAM (Random Access Memory), ROM (Read Only Memory), SSD (Solid State Drive), and HDD (Hard Disk Drive), etc. The memory unit is a general term for various memory such as the main memory and auxiliary memory. The program may be stored in the memory unit in advance, or downloaded from a device that is connected via a communication circuit (such as a server) and stored in the memory unit.

The fidelity calculation system of this implementation consists of an input section for inputting the data set prepared in step B-1 above. The aforementioned data set that is input to the input section is provided to the aforementioned processing section. The aforementioned processing section reads the program stored in the memory unit for calculating fidelity, and calculates fidelity according to the program, by inputting predictor variables included in or produced from the aforementioned data set into the model function that is also stored in the memory unit.

Also, in the preferred implementation form of the present invention, exclusion condition C1 and/or exclusion condition C2 created by the method for setting exclusion condition are recorded in the aforementioned memory unit. It is more preferable to have this fidelity calculation system to consist of an input section for inputting the data set prepared in step B-1 above.

In this implementation form, the aforementioned data set that is input to the input section is provided to the aforementioned processing section. The processing unit reads exclusion condition C1 and/or exclusion condition C2 stored in the memory unit, and applies the exclusion conditions to the data set to exclude any data that is not suitable for calculating fidelity. The processing unit reads the program for executing the method described above for calculating fidelity, and calculates fidelity according to the program, by inputting explanatory variables included in or produced from the aforementioned data set remaining after applying the exclusion conditions, to the model function also stored in the storage unit.

EXAMPLES OF IMPLEMENTATION

<Example Test 1> Creating a Model Function

A total of 200 data sets were prepared, with each set comprising genetic sequencing data that is obtained by analyzing the oral mucosa sample from the mother (with only maternal genetic information), the oral mucosa sample from the father (with only paternal genetic information), and the maternal plasma sample (with small amount of genetic information from the mother and the fetus), via next generation sequencing (NGS). NGS was executed with the polymorphic genetic loci consisting 184 known SNPs as the target sequence. The data set contains data for 36,800 SNPs (200 trios×184 SNPs).

Among the analysis data included in the data set for the whole blood sample from the mother, only data for the polymorphic genetic loci homozygous in both the mother and the father were extracted. Through this, the data set was narrowed down to 10,415 SNPs. Then, principal component analysis was performed on the following five factors in the extracted data set.

(1) Absolute value of primary contributor component signal intensity [Fetus Count Major]

(2) Absolute value of secondary contributor component signal intensity [Fetus Count minor]

(3) Primary contributor component mix rate (=(1)/Total signal intensity) [Fetus Freq. Major]

(4) Secondary contributor component mix rate (=(2)/Total signal intensity) [Fetus Freq. minor]

(5) Noise (=Total signal intensity−[(1)+(2)]) [Fetus error]

Also, the data in (1)~(5) above were standardized and principal component analysis was performed.

*(Standardized data)=[(Raw data)−(Mean)]/(Sample standard deviation)

The results clearly show that the first principal component is an indicator that is highly correlated with fidelity.

Each model function was created using the method described below. Since the authenticity of the secondary contributor component signal needs to be determined for creating model functions, the authenticity was determined based on the standard for the true/false, which was set according to the following rules.

If the genotype of the mother and the father is homozygous and identical, the genotype of the fetus is homozygous (the secondary contributor component signal intensity is false)

If the genotype of the mother and the father is homozygous and nonidentical, the genotype of the fetus is heterozygous (the secondary contributor component signal intensity is true)

Creating the Model Function f1(x1)

The first principal component obtained by the principal component analysis was divided into 20 categories according to its size. Next, the ratio of true secondary contributor component signal intensity corresponding to the first principal component in each category (probability) was calculated. Then, the probability for the category was assigned to the representative value of the first principal component in each category. Using least-squares method, regression analysis was performed on the first principal component and the fidelity that were obtained this way, and the model function f1(x1) with the first principal component as the predictor variable and fidelity as the objective variable was obtained. The contribution ratio ($R^2$) of the regression analysis was extremely good, more than 0.99.

Figure 1:
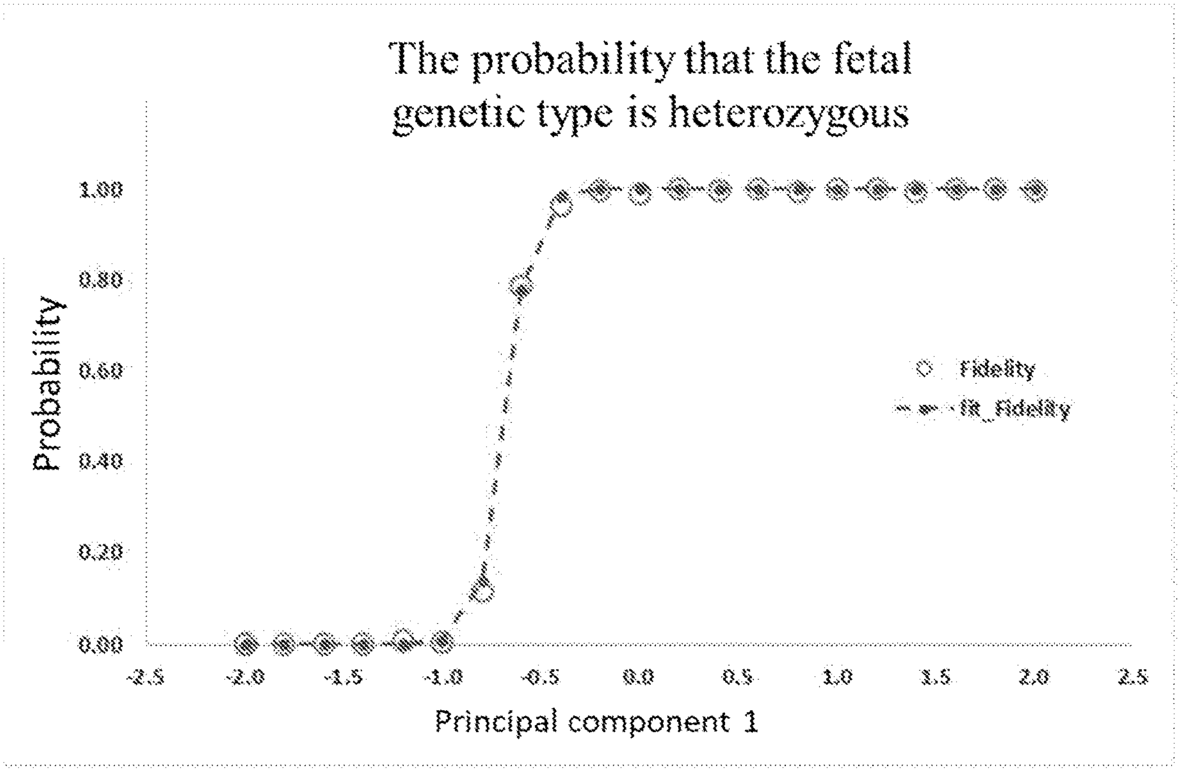
FIG. 1 The sigmoid curve showing the model function f1(x1). The "probability" on the vertical axis is the fidelity, and the "principal component 1" on the horizontal axis is the "first principal component" obtained by principal component analysis. The white data points in the figure indicate the fidelity and the first principal component used in the regression analysis.

FIG. 1 shows the sigmoid curve for the model function f1 (x1). Equation 5 below also represents the model function f1(x1).

$$f1(x1) = \frac{1}{1 + e^{-A1(x1-x01)}} \quad \text{[Equation 5]}$$

(x1: the first principal component, A1=15.5, x01=−0.7)

Creating the Model Function f2(x2)

The absolute value of the secondary contributor component signal intensity was divided into 20 categories according to its size. Next, the ratio of true absolute values of the secondary contributor component signal intensity in each category (probability) was calculated. Then, the probability for the category was assigned to the representative value of the absolute values of secondary contributor component signal intensity in each category. In this way, the model function f2(x2) with the absolute value of the secondary contributor component signal intensity as the predictor variable and fidelity as the objective variable was obtained. The contribution ratio ($R^2$) of the regression analysis was extremely good, more than 0.99.

Figure 2:
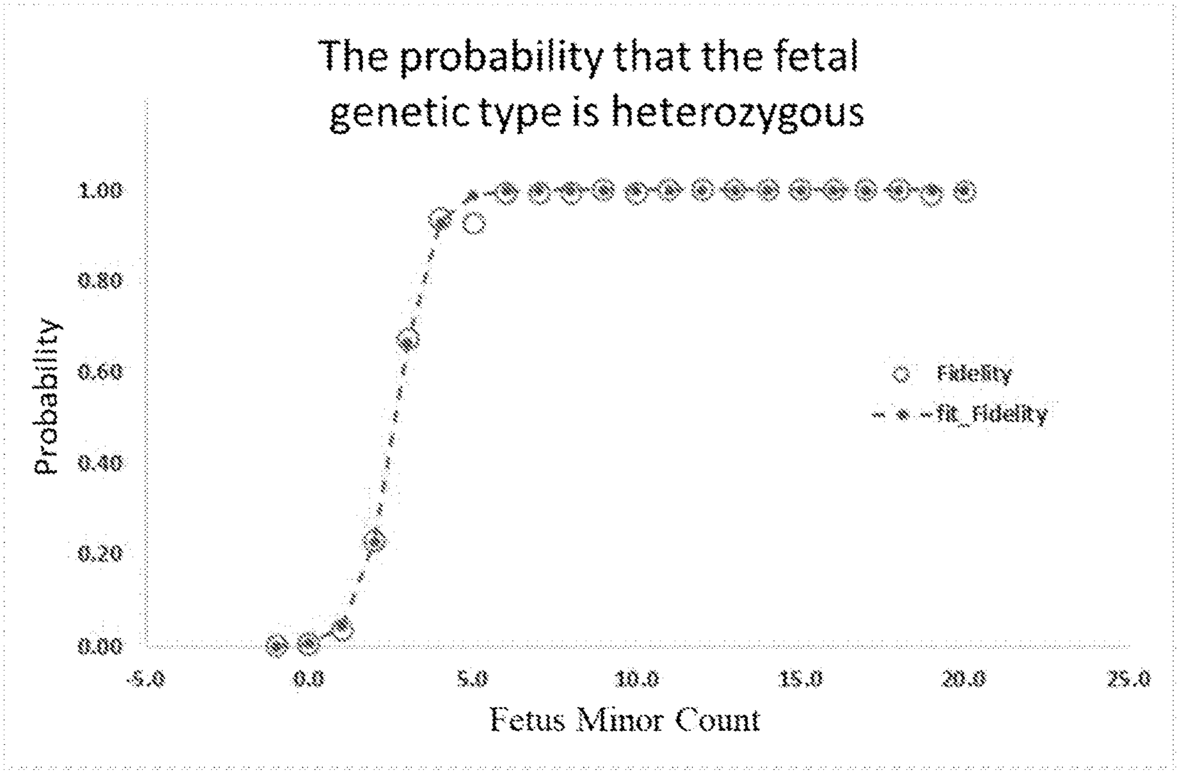
FIG. 2 The sigmoid curve showing the model function f2(x2). The "probability" on the vertical axis is the fidelity, and the "fetal minor count" on the horizontal axis is the absolute value of the secondary contributor component signal intensity. The white points in the figure indicate the fidelity and the absolute value of the secondary contributor component signal intensity used in the regression analysis.

FIG. 2 shows the sigmoid curve for the model function f2(x2). Equation 6 below also represents the model function f2(x2).

$$f2(x2) = \frac{1}{1 + e^{-A2(x2-x02)}} \quad \text{[Equation 6]}$$

(x2: secondary contributor component signal intensity, A2=1.9, x02=2.6)

Creating the Model Function f3(x3)

The absolute value of the secondary contributor component mix rate was divided into 20 categories according to its size. Next, the ratio of true secondary contributor component mix rate in each category (probability) was calculated. Then, the probability for the category was assigned to the representative value of the secondary contributor component mix rate in each category. In this way, the model function f3(x3) with the secondary contributor component mix rate as the predictor variable and fidelity as the objective variable was obtained. The contribution ratio ($R^2$) of the regression analysis was extremely good, more than 0.99.

Figure 3:
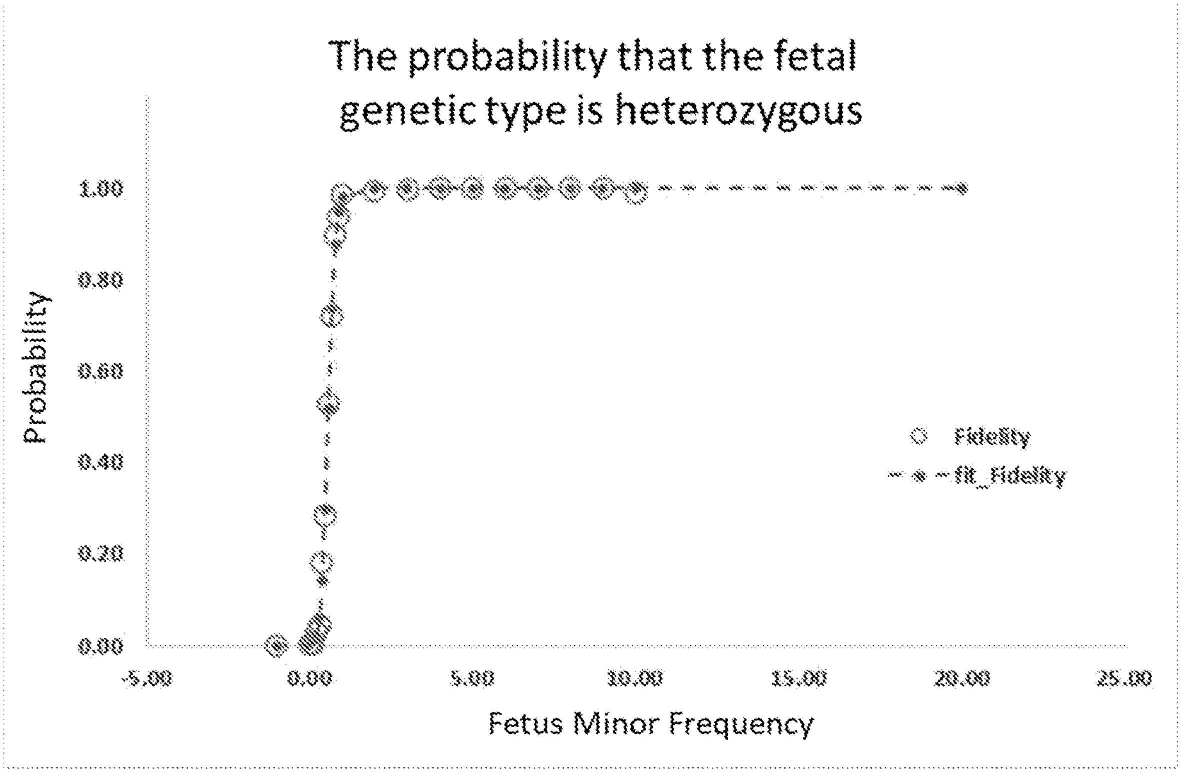
FIG. 3 The sigmoid curve showing the model function f3(x3). The "probability" on the vertical axis is the fidelity, and the "fetal minor frequency" on the horizontal axis is the secondary contributor component mix rate. The white data points in the figure indicate the fidelity and the secondary contributor component mix rate used in the regression analysis.

FIG. 3 shows the sigmoid curve for the model function f3(x3). Equation 7 below also represents the model function f3(x3).

$$f3(x3) = \frac{1}{1 + e^{-A3(x3-x03)}} \quad \text{[Equation 7]}$$

(x3: secondary contributor component mix rate, A3=9.4, x03=0.6)

Creating the Model Function f(x1, x2, x3)

By multiplying f1(x1), f2(x2), and f3(x3) by each other, the model function f(x1, x2, x3) represented by the following equation 4 was obtained.

$$f(x1,x2,x3)=f1(x1)*f2(x2)*f3(x3) \quad \text{[Equation 4]}$$

<Example Test 2> Calculating Fidelity

Using the model function f(x1, x2, x3) in Equation 4, the fidelity of the 200 data sets used to create the model function was calculated and the results were verified. That is, the first principal component, the absolute value of the secondary contributor component signal intensity, and the secondary contributor component mix rate for the loci pertaining to the SNPs in the nucleic acid mix sample were input to the model function f(x1, x2, x3), and the fidelity was calculated. When calculating fidelity, that with a total value less than 300 for (1) and (2) combined was excluded, and the fidelity of the 8,148 SNPs was calculated.

FIG. 4 shows the distribution diagram of the calculated fidelity.

The left panel shows the aggregated fidelity for SNPs that are homozygous and the genotype is nonidentical in each parent (the fetal genotype is heterozygous).

The right panel shows the aggregated fidelity for SNPs that are homozygous and the genotype is identical in each parent (the fetal genotype is homozygous).

As shown in FIG. 4, the method in the present invention can evaluate the fidelity of the signals for SNPs with high accuracy.

<Example Test 3> Evaluating Exclusion Conditions

At the upper left of FIG. 4 (SNPs homozygous and the genotype is nonidentical in each of the parent), values with the calculated fidelity less than 0.19 are distributed, and a certain number of exception cases can be found. Also, at the upper right of FIG. 4. (SNPs homozygous and the genotype is identical in each of the parent) as well, values greater than or equal to 0.9 are distributed, and a certain number of aberrant cases were found.

In cases where the genotype of the fetus is heterozygous, but the calculated fidelity is low (for example less than 0.1), on in cases where the genotype of the fetus is homozygous, but the calculated fidelity is high (for example, greater than or equal to 0.9), exclusion conditions were examined in detail to exclude aberrant results.

Exclusion Condition 1

Principal component analysis was performed for the parameters (1)~(5) above on the SNPs (3,196 in total) that were obtained by analyzing the nucleic acid mix sample, for the SNPs that are homozygous and the genotype is nonidentical in each of the parents (the genotype of the fetus is heterozygous).

On the other hand, the fidelity was calculated based on the parameters (1)~(5), using the model function f(x1, x2, x3) above.

Figure 5:
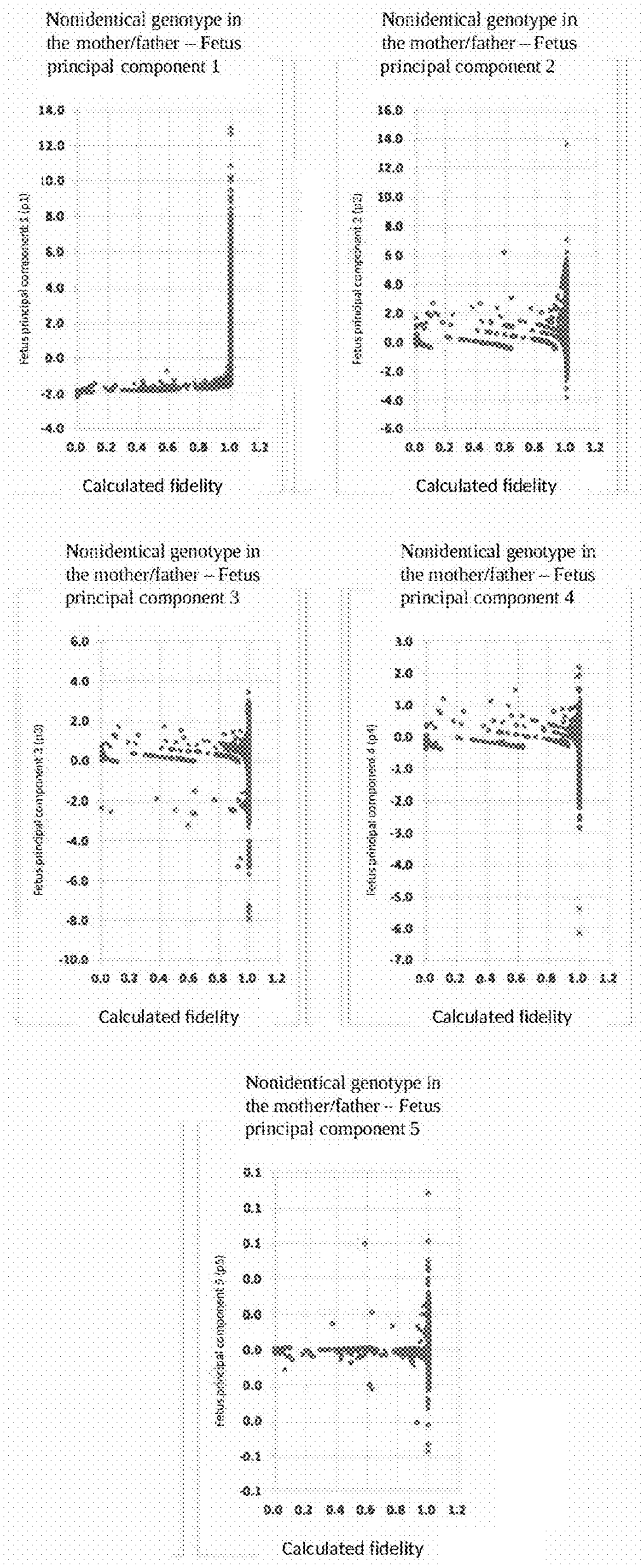
FIG. 5 The scatter plot on which each principal component obtained by the principal component analysis created to examine Exclusion Condition 1 is plotted on the y-axis, and the fidelity is plotted on the x-axis. From left to right are the scatter plots with the first, second, third, fourth, and fifth principal components on the y-axis.

Next, a scatter plot was created with each principal component obtained from the principal component analysis plotted on the y-axis, and the fidelity plotted on the x-axis (FIG. 5). As shown in the scatter plot of the first principal component where the variance of the data was the largest, two sets of data points, one extending in the x-axis direction and the other in the y-axis direction, were observed. The set of data points extending in the x-axis direction were considered to be outliers to be excluded, and the threshold was set at −1.9 for each first principal component. Based on this threshold, the following exclusion condition 1 was set.

(Exclusion Condition 1)

For the SNPs that are homozygous and the genotype is nonidentical in each of the parents, data with the first principal component of the (1)~(5) above that are less than −1.9 are excluded from the data sets.

Exclusion Condition 2

Whether appropriate exclusion conditions can be set for that SNPs that are homozygous and the genotype is identical in each of the parents, was examined.

Principal component analysis was performed for the aforementioned parameters (1)~(5) above on the SNPs (4,952 in total) that were obtained by analyzing the nucleic acid mix sample, for the SNPs that are homozygous and the genotype is identical in each of the parents (the genotype of the fetus is homozygous).

On the other hand, the fidelity was calculated based on the parameters (1)~(5), using the model function f(x1, x2, x3) above.

Figure 6:
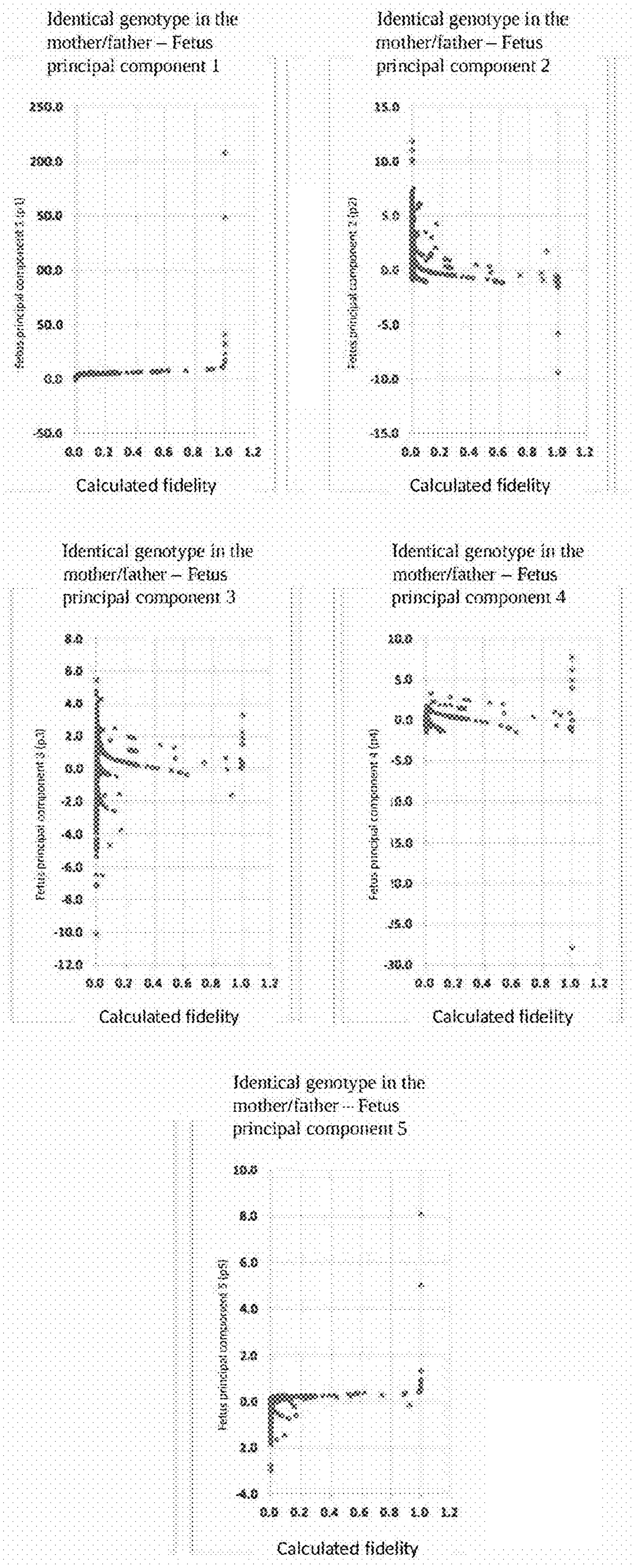
FIG. 6 The scatter plot on which each principal component obtained by the principal component analysis created to examine Exclusion Condition 2 is plotted on the y-axis, and the fidelity is plotted on the x-axis. From left to right are the scatter plots with the first, second, third, fourth, and fifth principal components on the y-axis.

Next, a scatter plot in which each principal component obtained from the principal component analysis are plotted on the y-axis and the fidelity on the x-axis, was created (FIG. 6).

As shown in the scatter plot of the first principal component with the largest data variance, two sets of data points, one extending in the x-axis direction and the other extending in the y-axis direction were observed. The set of data points extending in the y-axis direction were considered to be outliers to be excluded, and a threshold value was set at 6 for the first principal component. Based on this threshold, the following exclusion condition 2 was set.

(Exclusion Condition 2)

For the SNPs that are homozygous and the genotype is identical in each of the parents, data with the first principal component of the (1)~(5) above that are less than 6 are excluded from the data sets.

<Example Test 4> Re-Calculating Fidelity

After excluding data related to SNPs corresponding to Exclusion Condition 1 and Exclusion Condition 2 that were set at Example Test 3, in which 200 test data sets were prepared, the fidelity was calculated using the same order of procedure as Example Test 1 (number of remaining SNPs after the exclusion: 8,081).

FIG. 7 shows the distribution of the calculated fidelity.

The left panel shows the fidelity for SNPs homozygous and the genotype is nonidentical in each of the parents (the genotype of the fetus is heterozygous).

The right panel shows the fidelity of SNPs homozygous and the genotype is identical in each of the parents (the genotype of the fetus is homozygous).

The left panel of FIG. 7 shows the scatter plot of the fidelity for the data remaining after applying Exclusion Condition 1. The right panel of FIG. 7 shows the scatter plot of the fidelity for the data remaining after applying Exclusion Condition 2. As shown in FIG. 7, as a result of applying Exclusion Condition 1 or Exclusion Condition 2, the number of aberrant cases was significantly excluded and the validity of the data was improved.

<Example Test 5> Evaluation of Validity of Different NGS Target Panels

The following evaluation was performed using the 16 data sets that were separately prepared to verify the validity of the present intention. This is the result from the analysis of the target panel of 132 SNPs, which is different from the target panel of 184 SNPs in Example Test 1.

With the genetic sequencing data from the NGS analysis of the oral mucosa sample from the mother, the oral mucosa sample from the father, the plasma sample from the mother, and the oral mucosa sample from the newborn baby as one set of data, 16 sets of data were prepared separately from the Example Test 1~3. NGS was executed with the polymorphic genetic loci consisting 132 known SNPs as the target sequence. The data set contains data for 2,112 SNPs (16 pairs×132 SNPs).

The 132 SNPs analyzed in the present example test do not completely overlap with the 184 SNPs analyzed in Example Test 1~3. 71 SNPs are different from the SNPs analyzed in Example Test 1~3.

From this data set, SNPs homozygous in both the mother and the father were extracted, and the fidelity for the extracted 531 SNPs were calculated.

Figure 8:
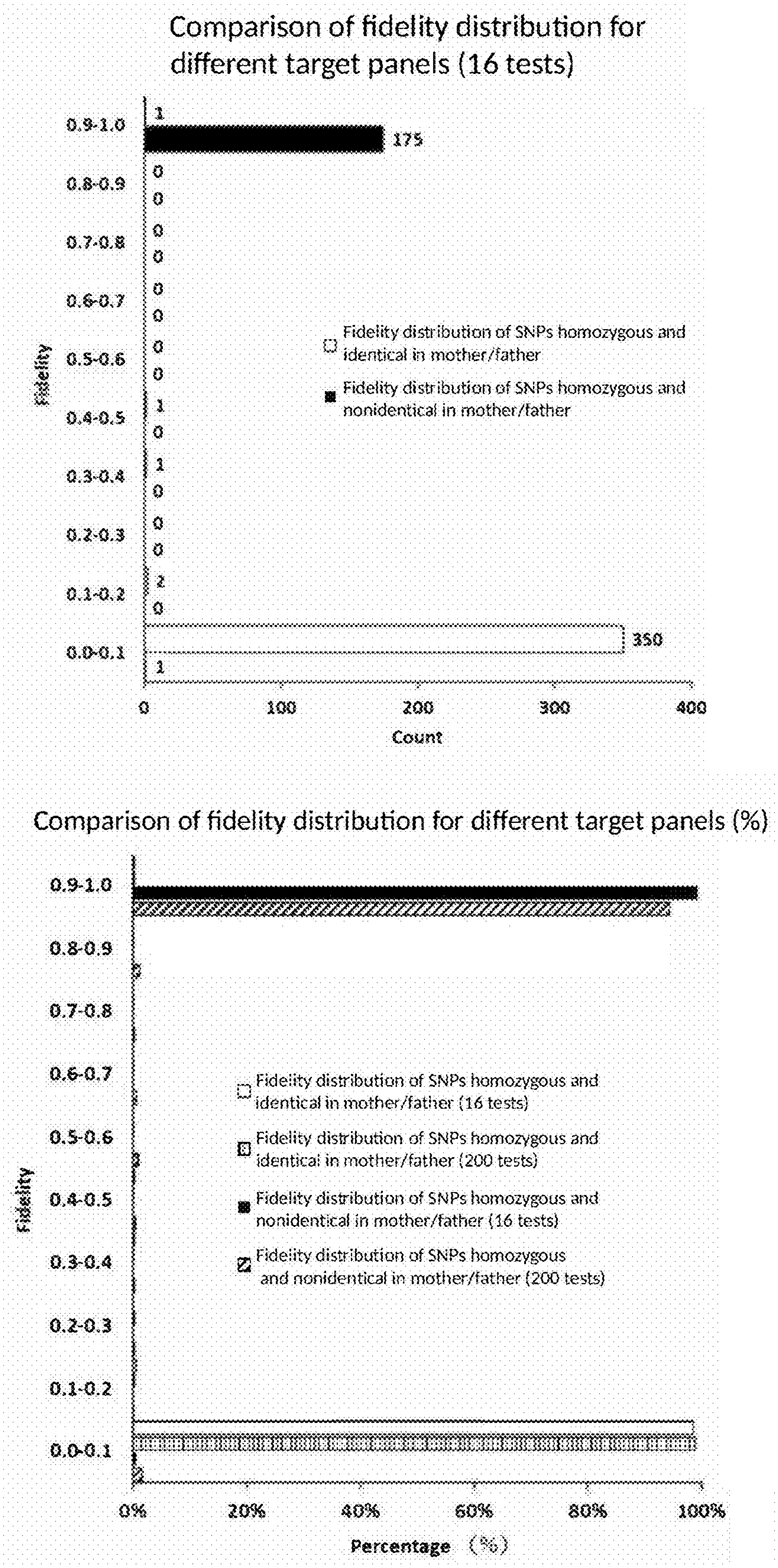
FIG. 8 The distribution diagram of fidelity calculated in Test Example 5. The left panel shows the aggregated fidelity for SNPs of mutually nonidentical and identical genotypes that are homozygous for each parent. The right panel shows the ratio of fidelity calculated from Test Example 2 and Test Example 5, which are NGS target panel analyses different from each other.

FIG. 8 shows the scatter plot on the fidelity calculated from the 16 data sets.

The left panel shows the fidelity for SNPs homozygous and the genotype is nonidentical in each of the parents (the genotype of the fetus is heterozygous), the for SNPs homozygous and the genotype is identical in each of the parents (the genotype of the fetus is homozygous).

For SNPs homozygous and the genotype is nonidentical in each of the parents, 175 out of 176 SNPs have fidelity greater than or equal to 0.9. Also, for SNPs homozygous and the genotype is identical in each of the parents, only 1 out of 355 SNPs has the fidelity greater than or equal to 0.5.

The right panel shows the scatter plot of fidelity for a target panel different from Example Test 1.

Although the model function obtained from 200 data sets (target panel of 184 SNPs) was used for analyzing 16 data sets (132 target panels), a similar scatter plot of fidelity was obtained.

These results confirm that if the same test system is used as the method for calculating fidelity in the present invention, correct answer will be obtained regardless of the type of the target panel.

<Example Test 6> Evaluation of Validity of SNPs with Unclear Authenticity

Figure 9:
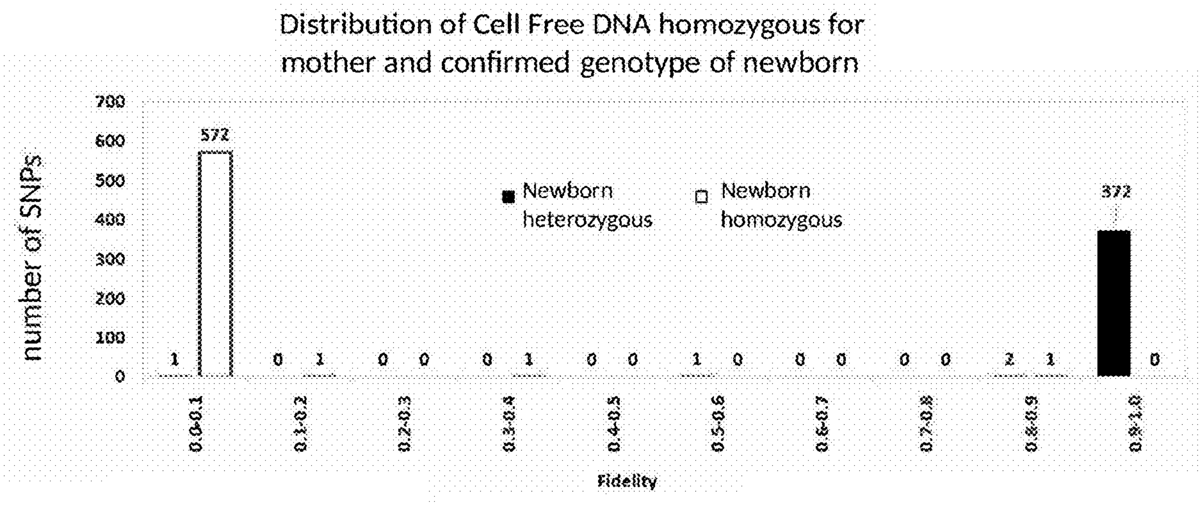
FIG. 9 The graph showing the aggregated fidelity corresponding to the genotype of SNPs identified from the analyses of a newborn in Test Example 6.

Of the 16 data sets used in Example Test 5, the distribution of the fidelity of 951 SNPs homozygous in the mother was tabulated with the genotype of newborn baby, and shown in FIG. 9.

All SNPs shown in FIG. 9 have the sum of Fetus Count Major and Fetus Count minor greater than or equal to 300.

As FIG. 9 shows, the genotype of the fetus predicted from the genotype of the parents was equivalent to the genotype confirmed after birth. In total, 99.6% (573 SNPs of 575 SNPs) of the heterozygous SNPs of the newborn baby have low fidelity less than or equal to 0.2, and 99.4% (374 SNPs of 376 SNPs) of the heterozygous SNPs of the newborn baby have high fidelity greater than or equal to 0.8.

Therefore, according to the method for calculating fidelity using the model function in Example Test 1, fidelity can be accurately calculated even when the genotype of the father, which determines the authenticity of the secondary contributor component signal, is unknown.

From this result, the versatility of the present invention was confirmed.

<Example Test 7> Creating a Model Function (2)

For the same data set used in Example Test 1, only the data for polymorphic loci homozygous in the mother and the father was extracted. Then, principal component analysis was performed on the 13 factors shown in Table 1 below, which are included in the extracted data set. Table 1 shows the eigenvectors for the first principal component obtained from the principal component analysis.

TABLE 1

| | Variable | First principal component |
|---|---|---|
| (1) | Fetus Count_Major | 0.008710919 |
| (2) | Fetus Count_minor | 0.37133704 |
| (3) | Fetus Freq_Major | −0.397335595 |
| (4) | Fetus Freq_minor | 0.397377539 |
| (5) | Fetus Error | 0.011977182 |
| (6) | Count_Major/Ave.Error | 0.012044526 |
| (7) | Count_minor/Ave.Error | 0.375885418 |
| (8) | Frequency_Major/Ave.Error | 0.001745322 |
| (9) | Frequency_minor/Ave.Error | 0.329854084 |
| (10) | Forward read count_Major | 0.007477871 |
| (11) | Reverse read count_Major | 0.009211129 |
| (12) | MFAA count_Major | 0.371226399 |
| (13) | MFAA frequency_Major | 0.397383319 |

The (1)~(5) of the 13 factors shown in Table 1 are as explained in Example Test 1. As for the notation of variables listed in Table 1, those containing “major” are data related to the primary contributor component signal, and those containing “minor” are data related to the secondary contributor component signal. Also, as for the notation of variables in Table 1, those containing “count” are data related to signal intensity, and those containing “freq” or “frequency” are data related to ratio of signal intensity.

In other words, the numerical values that include both “minor” and “count” in the notation of the variables listed in Table 1, correspond to the “secondary contributor component signal intensity” in the present invention.

In addition, the numerical values that include both “minor” and “freq” or “frequency” in the notation of the variables listed in Table 1, correspond to the “secondary contributor component mix rate” in the present invention.

(7) in Table 1 corresponds to the numerical value obtained by dividing the secondary contributor component signal intensity indicating the presence of the alleles at the aforementioned specific polymorphic genetic loci, by the average value of the noise at multiple polymorphic genetic loci.

(9) in Table 1 corresponds to numerical value obtained by diving the secondary contributor component mix rate, which is the ratio of the signal intensity of the aforementioned secondary contributor component signal intensity to the total signal intensity derived from the alleles at the aforementioned specific polymorphic genetic loci.

Based on the first principal component obtained from the principal component analysis, the model function f1(x1), with the first principal component x1 as the predictor variable and the fidelity as the objective variable, was created using the same procedures as Example Test 1. The contribution rate of the regression analysis ($R^2$) was very good, more than 0.99.

This f1(x1) was multiplied by f2(x2) and f3(x3) described above to create the model function f(x1, x2, x3) expressed in Equation 4 above.

<Example Test 8> Calculating Fidelity (2)

Principal component analysis was performed on the 13 factors shown in Table 1, which comprises the same data set as that used in Example Test 1. The first principal component, the absolute value of the secondary contributor component signal intensity, and the secondary contributor component mix rate obtained by principal component analysis, were input into the model function f(x1, x2, x3) created in Example Test 7, to calculate the fidelity. FIG. 10 is the scatter plot on the fidelity calculated by performing principal component analysis on the 5 or 13 factors.

As shown in FIG. 10, extremely accurate results were obtained with almost no outliers in the present example test. This result proves the validity and accuracy of the model function created in Example Test 7.

<Example Test 9> Verifying Validity (2)

Principal component analysis was performed on the 13 factors shown in Table 1, which comprises the same data set as that used in Example Test 6. The first principal component, the absolute value of the secondary contributor component signal intensity, and the secondary contributor component mix rate obtained by principal component analysis were input into the model function f(x1, x2, x3) created in Example Test 7, to calculate the fidelity. FIG. 11 is the scatter plot on the fidelity calculated by performing principal component analysis on the 5 or 13 factors.

As shown in FIG. 11, even when the genotype of the father that shows the authenticity of the secondary contributor component signal is unknown, extremely accurate results were obtained with almost no outliers. This result proves the validity and accuracy of the model function created in Example Test 7.

POSSIBLE INDUSTRIAL APPLICATIONS

The present invention can be applied to prenatal genetic testing, cancer screening tests, transplant organ engraftment monitoring, infectious disease tests, forensic science, and etc.

The invention claimed is:

1. A method of calculating fidelity of a secondary contributor component signal in cell-free DNA analysis, the method comprising:

preparing, as a predictor variable, one or more numerical values selected from the group consisting of: (B1), (B2), and one or more composite variables obtained in step B-2 from a second data set prepared in step B-1; and obtaining the fidelity of the secondary contributor component signal by inputting the predictor variable into a model function, wherein the model function is:

(i) a model function created by a method comprising step S-1, step S-2, step S-3-1, and step S-4-1, (ii) a model function of any one of Equations 1 to 3, or (iii) a multiplication model function obtained by multiplying two or more model functions selected from the group consisting of the model functions of Equations 1 to 3;

wherein step S-1 comprises preparing a first data set obtained by measuring a nucleic acid mix sample, wherein the nucleic acid mix sample contains primary contributor nucleic acids and secondary contributor nucleic acids having genetic information from the primary contributor and the secondary contributor, respectively, and wherein the first data set contains signals indicating presence of each allele at multiple polymorphic genetic loci in the primary contributor nucleic acids and the secondary contributor nucleic acids, authenticity of the signals included in the first data set being known in advance;

wherein step S-2 comprises producing one or more composite variables by linearly combining a numerical group that includes at least (F1) and (F2), for polymorphic genetic loci, among the multiple polymorphic genetic loci, at which signals indicating the presence of alleles derived from the primary contributor nucleic acids and signals indicating the presence of alleles derived from the secondary contributor nucleic acids are separately detected from data of the first data set, wherein (F1) is a secondary contributor component signal intensity indicating the presence of alleles at specific polymorphic genetic loci derived from the secondary contributor nucleic acids, and wherein (F2) is a secondary contributor component mix rate indicating a ratio of the secondary contributor component signal intensity to a total signal intensity derived from alleles at the specific polymorphic genetic loci;

wherein step S-3-1 comprises dividing the one or more composite variables produced in step S-2 into multiple categories, and assigning, as a probability corresponding to the composite variables in each category, a ratio of true secondary contributor component signal intensities corresponding to the composite variables in that category;

wherein step S-4-1 comprises performing regression analysis on the one or more composite variables in each category and the probability corresponding to the one or more composite variables in each category, to obtain a model function for calculating fidelity, wherein the one or more composite variables are predictor variables and the fidelity is an objective variable;

wherein step B-1 comprises:

preparing the second data set by measuring a second nucleic acid mix sample, wherein the second nucleic acid mix sample contains primary contributor nucleic acids having genetic information from the primary contributor, and contains secondary contributor nucleic acids having genetic information from the secondary contributor, and the second data set contains signals indicating the presence of each allele at multiple polymorphic genetic loci in the primary contributor nucleic acids and the secondary contributor nucleic acids;

wherein step B-2 comprises:

producing one or more composite variables by linearly combining a numerical group that includes at least the following (B1) and (B2), for polymorphic genetic loci, among the multiple polymorphic genetic loci at which signals indicating the presence of alleles derived from the primary contributor nucleic acids and signals indicating the presence of alleles derived from the secondary contributor nucleic acids are each detected from data of the second data set, wherein (B1) is a secondary contributor component signal intensity indicating the presence of alleles at the specific polymorphic genetic loci derived from the secondary contributor nucleic acids, and wherein (B2) is a secondary contributor component mix rate indicating a ratio of the secondary contributor component signal intensity to a total signal intensity derived from alleles at the specific polymorphic genetic loci, wherein Equation 1 is:

$$f1(x1) = \frac{1}{1 + e^{-A1(x1 - x01)}}$$

(x1: the first principal component, A1: gradient of transition region, x01: half point);

wherein in Equation 1, A1 is in a range from 15.4 to 15.6, and x01 is in a range from −0.8 to −0.6, wherein Equation 2 is:

$$f2(x2) = \frac{1}{1 + e^{-A2(x2 - x02)}}$$

(x2: secondary contributor component signal intensity, A2: gradient of transition region, x02: half point);

wherein in Equation 2, A2 is in a range from 1.8 to 2.0, and x02 is in a range from 2.5 to 2.7, wherein Equation 3 is:

$$f3(x3) = \frac{1}{1 + e^{-A3(x3 - x03)}}$$

(x3: secondary contributor component mix rate, A3: gradient of transition region, x03: half point);

wherein in Equation 3, A3 is in a range from 9.3 to 9.5, and x03 is in a range from 0.5 to 0.7.

2. The method according to claim 1, wherein the primary contributor is a mother, the secondary contributor is a fetus in a womb of the mother, the second nucleic acid mix sample comprises a circulating cell-free nucleic acid sample collected from the mother, and wherein, step B-1 further comprises step B1-1 and step B-2 further comprises step $B_1$-2, wherein Step $B_1$-1 comprises:

preparing a third data set obtained by measuring a circulating cell-free nucleic acid sample, wherein the circulating cell-free nucleic acid sample contains a primary contributor nucleic acid with genetic information from the mother and a secondary contributor nucleic acid with genetic information from the fetus, and the third data set contains signals indicating the presence of each allele at multiple polymorphic genetic loci in the primary and secondary contributor nucleic acids; and wherein Step $B_1$-2 comprises:

producing the one or more composite variables by linearly combining a numerical group that includes at least (B1) and (B2) for polymorphic genetic loci that are homozygous in the mother, and having signals indicating the presence of alleles derived from each of the primary and secondary contributor nucleic acids among the multiple polymorphic genetic loci.

3. The method according to claim 1, wherein the primary contributor is a cancer test subject, the secondary contributor is cancer cells, the second nucleic acid mix sample is a circulating cell-free nucleic acid sample collected from the cancer test subject, and wherein step B-1 further comprises step B2-1, and step B-2 further comprises step $B_2$-2, wherein Step B2-1 comprises:

preparing a third data set obtained by measuring a circulating cell-free nucleic acid sample, wherein the circulating cell-free nucleic acid sample contains a primary contributor nucleic acid with genetic information from the cancer test subject and a secondary contributor nucleic acid with genetic information from the cancer cells, and the third data set contains signals indicating the presence of each allele at multiple polymorphic genetic loci associated with cancer in the primary and secondary contributor nucleic acids;

wherein Step $B_2$-2 comprises:

producing the one or more composite variables by linearly combining a numerical group that includes at least (B1) and (B2), for polymorphic genetic loci at which each of signals indicating presence of normal type alleles and signals indicating presence of a mutant type allele among the multiple polymorphic genetic loci from the data of the third data set are detected.

4. The method according to claim 1, wherein the primary contributor is a recipient of an organ transplant, the secondary contributor is a transplanted organ, wherein the nucleic acid mix sample comprises a circulating cell-free nucleic acid sample collected from the recipient, and wherein step B-1 further comprises step B3-1 and step B-2 further comprises step $B_3$-2, wherein Step B3-1 comprises:

preparing a third data set obtained by measuring a circulating cell-free nucleic acid samples, wherein the circulating cell-free nucleic acid sample contains primary contributor nucleic acid with genetic information from the recipient, and contains secondary contributor nucleic acid with genetic information from the transplanted organ, and the third data set contains signals indicating the presence of each allele at the multiple polymorphic genetic loci in the primary and secondary contributor nucleic acids; and wherein Step $B_3$-2 comprises:

producing the one or more composite variables by linearly combining a numerical group that includes at least (B1) and (B2) for polymorphic genetic loci at which each of the signals indicating the presence of alleles derived from the primary contributor nucleic acid and the secondary contributor nucleic acid among the multiple polymorphic genetic loci from the data of the third data set are detected.

5. The method of claim 1, further comprising setting an exclusion condition C1, wherein the exclusion condition C1 is a numerical condition including a threshold for at least one of the one or more composite variables, the numerical condition produced by linearly combining a numerical group including one or more of (F1), (F2), and (F3), wherein (F3) is a primary contributor component noise signal intensity indicating noise of the signal indicating the presence of alleles derived from the primary contributor nucleic acids at the specific polymorphic genetic loci;

removing, from the second data set, data for polymorphic genetic loci that satisfy the exclusion condition C1 to obtain a remaining data set; and calculating the fidelity based on the remaining data set.

6. The method of claim 1, further comprising setting exclusion condition C2, wherein the nucleic acid mix sample contains primary contributor nucleic acid with genetic information from a mother and secondary contributor nucleic acid with genetic information from a fetus, or the nucleic acid mix sample contains primary contributor nucleic acid with genetic information from a recipient, and secondary contributor nucleic acid with genetic information from a transplanted organ, and the exclusion condition C2 is the composite variable with the highest or the second highest contribution rate that is obtained by linearly combining a numerical group that includes at least (F1), (F2), and (F3), wherein (F3) is noise obtained by subtracting the primary and secondary contributor component signal intensities from the total signal intensity derived from alleles at polymorphic genetic loci with alleles that are homozygous in the mother and homozygous in a father of the fetus, and the genotype is identical in the mother and the father, or at alleles that are homozygous in the recipient and homozygous in a donor of the transplanted organ, and the genotype is identical in the recipient and the donor removing, from the second data set, data for polymorphic genetic loci that satisfy the exclusion condition C2 to obtain a remaining data set; and calculating the fidelity based on the remaining data set.

7. The method of claim 1, wherein the second nucleic acid mix sample is a circulating cell-free nucleic acid sample, wherein the circulating cell-free nucleic acid sample contains primary contributor nucleic acids the primary contributor is genetic information from a mother, the secondary contributor is genetic information from a fetus in a womb of the the method further comprising removing data related to polymorphic genetic loci with a mutant allele heterozygous in the mother from the data in the data set.

8. A method of calculating fidelity of a secondary contributor component signal in cell-free DNA analysis, the method comprising:

preparing, as a predictor variable, one or more numerical values selected from the group consisting of (B1), (B2), and one or more composite variables obtained in step B-2 from a second data set prepared in step B-1; and inputting the predictor variable into a model function, wherein the model function is a model function created by a method comprising step A-1, step A-2, step A-3-1, and step A-4-1, wherein step A-1 comprises preparing a first data set obtained by measuring a nucleic acid mix sample, wherein the nucleic acid mix sample contains primary contributor nucleic acids and secondary contributor nucleic acids having genetic information from the primary contributor and the secondary contributor, respectively, and wherein the first data set contains signals indicating presence of each allele at multiple polymorphic genetic loci in the primary contributor nucleic acids and the secondary contributor nucleic acids, authenticity of the signals included in the first data set being known in advance;

wherein step A-2 comprises producing one or more composite variables by linearly combining a numerical group that includes at least (F1) and (F2), for polymorphic genetic loci, among the multiple polymorphic genetic loci, at which signals indicating the presence of alleles derived from the primary contributor nucleic acids and signals indicating the presence of alleles derived from the secondary contributor nucleic acids are separately detected from data of the first data set, wherein (F1) is a secondary contributor component signal intensity indicating the presence of alleles at specific polymorphic genetic loci derived from the secondary contributor nucleic acids, and wherein (F2) is a secondary contributor component mix rate indicating a ratio of the secondary contributor component signal intensity to a total signal intensity derived from alleles at the specific polymorphic genetic loci;

wherein step A-3-1 comprises dividing the one or more composite variables produced in step A-2 into multiple categories, and assigning, as a probability corresponding to the composite variables in each category, a ratio of true secondary contributor component signal intensities corresponding to the composite variables in that category;

wherein step A-4-1 comprises performing regression analysis on the one or more composite variables in each category and the probability corresponding to the one or more composite variables in each category, to obtain a model function for calculating fidelity, wherein the one or more composite variables are predictor variables and the fidelity is an objective variable;

wherein step B-1 comprises:

preparing the second data set by measuring a second nucleic acid mix sample, wherein the second nucleic acid mix sample contains primary contributor nucleic acids having genetic information from the primary contributor, and contains secondary contributor nucleic acids having genetic information from the secondary contributor, and the second data set contains signals indicating the presence of each allele at multiple polymorphic genetic loci in the primary contributor nucleic acids and the secondary contributor nucleic acids;

wherein step B-2 comprises:

producing one or more composite variables by linearly combining a numerical group that includes at least the following (B1) and (B2), for polymorphic genetic loci, among the multiple polymorphic genetic loci at which signals indicating the presence of alleles derived from the primary contributor nucleic acids and signals indicating the presence of alleles derived from the secondary contributor nucleic acids are each detected from data of the second data set;

wherein (B1) is a secondary contributor component signal intensity indicating the presence of alleles at the specific polymorphic genetic loci derived from the secondary contributor nucleic acids, and wherein (B2) is a secondary contributor component mix rate indicating a ratio of the secondary contributor component signal intensity to a total signal intensity derived from alleles at the specific polymorphic genetic loci.

9. The method according to claim 8, wherein two or more first composite variables are produced in step A-2, wherein a probability is assigned to each of the two or more first composite variables in step A-3-1, wherein two or more mutually independent model functions are created in step A-4-1, each of the two or more first composite variables being used as a corresponding predictor variable; and further comprising creating a multiplication model function by multiplying the two or more mutually independent model functions.

10. The method according to claim 8, further comprising creating a multiplication model function by multiplying two or more model functions created by the method according to claim 8.

11. The method according to claim 8, wherein:

the primary contributor is a mother, the secondary contributor is a fetus in a womb of the mother, the nucleic acid mix sample comprises a circulating cell-free nucleic acid sample collected from the mother, wherein the circulating cell-free nucleic acid sample contains primary contributor nucleic acid with genetic information from the mother and secondary contributor nucleic acid with genetic information from the fetus, the second nucleic acid mix sample is a circulating cell-free nucleic acid sample collected from a test mother, and the polymorphic genetic loci are homozygous in the mother and homozygous in a father.

12. The method according to claim 8, wherein:

the primary contributor is a test subject with a healthy body, the secondary contributor is cancer cells, the nucleic acid mix sample is prepared by adding secondary contributor nucleic acid consisting of multiple nucleic acid fragments with sequence information of polymorphic genetic loci where cancer-associated mutations have been introduced to a nucleic acid sample collected from the test subject that contains primary contributor nucleic acid containing genetic information of the test subject, the second nucleic acid mix sample collected from the test subject suspected of carrying cancer cells, and the first data set contains signals indicating the presence of normal type alleles in the primary contributor nucleic acid, and signals indicating the presence of alleles containing the mutations in the secondary contributor nucleic acid.

13. The method according to claim 8, wherein:

the primary contributor is a recipient of an organ transplant, the secondary contributor is a transplanted organ, the nucleic acid mix sample contains primary contributor nucleic acid with genetic information from the recipient of the organ transplant and secondary contributor nucleic acid with genetic information from the transplanted organ, and the second nucleic acid mix sample is a nucleic acid sample collected from the recipient of the organ transplant.

* * * * *